(12) United States Patent
Kiapour et al.

(10) Patent No.: US 12,220,337 B2
(45) Date of Patent: Feb. 11, 2025

(54) SOFT BRACES TO PREVENT INJURY TO A JOINT OR BODY SEGMENT

(71) Applicants: PRESIDENT AND FELLOWS OF HARVARD COLLEGE, Cambridge, MA (US); CHILDREN'S MEDICAL CENTER CORPORATION, Boston, MA (US)

(72) Inventors: Ata Kiapour, Wayland, MA (US); Dmitry Popov, Somerville, MA (US); Rachel M. Granberry, Saint Paul, MN (US); Danielle L. Nathanson, Chicago, IL (US); Asa M. Eckert-Erdheim, Cambridge, MA (US); Conor James Walsh, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 16/621,501

(22) PCT Filed: Jun. 13, 2018

(86) PCT No.: PCT/US2018/037397
§ 371 (c)(1),
(2) Date: Dec. 11, 2019

(87) PCT Pub. No.: WO2018/232029
PCT Pub. Date: Dec. 20, 2018

(65) Prior Publication Data
US 2020/0214869 A1    Jul. 9, 2020

Related U.S. Application Data

(60) Provisional application No. 62/519,079, filed on Jun. 13, 2017.

(51) Int. Cl.
*A61F 5/01* (2006.01)
*A63B 71/08* (2006.01)

(52) U.S. Cl.
CPC .......... *A61F 5/0106* (2013.01); *A61F 5/0111* (2013.01); *A61F 5/0118* (2013.01);
(Continued)

(58) Field of Classification Search
CPC .............. A63B 71/081; A63B 69/0062; A63B 71/1225; A63B 2071/125; A61F 5/0125;
(Continued)

(56) References Cited

U.S. PATENT DOCUMENTS

| 4,753,229 A | 6/1988 | Sutherland |
| 4,805,606 A * | 2/1989 | McDavid, III ........ A61F 5/0125 2/22 |

(Continued)

FOREIGN PATENT DOCUMENTS

WO    2015171012 A1    11/2015

OTHER PUBLICATIONS

"Generate." Merriam-Webster.com Dictionary, Merriam-Webster, https://www.merriam-webster.com/dictionary/generate. Accessed Mar. 24, 2023. (Year: 2023).*

(Continued)

*Primary Examiner* — Keri J Nelson
*Assistant Examiner* — Seth R. Brown
(74) *Attorney, Agent, or Firm* — Greenberg Traurig, LLP; Melissa Hunter-Ensor; Joshua I. Rudawitz

(57) ABSTRACT

A soft brace to prevent injury to one or more target joints or body segments is disclosed. The soft brace includes one or more tensile elements configured to limit motion of one or more target joints based on placement of the one or more tensile elements relative to the one or more target joints such that the placement and tension of each of the one or more
(Continued)

tensile elements provides resistance against motion of the one or more target joints; one or more soft tissue anchors positioned on a body around the one or more target joints, the one or more anchors being configured to anchor one or more of the one or more tensile elements to the body to provide force distribution relative to the one or more target joints; and wherein at least one of the one or more tensile elements is routed in parallel with the approximate center of rotation of at least one of the one or more target joints.

16 Claims, 44 Drawing Sheets

(52) U.S. Cl.
CPC .......... *A61F 5/0123* (2013.01); *A63B 71/081* (2013.01); *A61F 2005/0183* (2013.01)

(58) Field of Classification Search
CPC .... A61F 5/0102; A61F 5/0106; A61F 5/0109; A61F 5/0111; A61F 5/0123; A61F 5/0127; A61F 5/0193; A61F 5/012; A61F 5/013; A61F 2005/0183; A61F 2005/0188; A61F 5/0118; A61H 1/0237; A61H 1/024
USPC ............................................................ 602/6
See application file for complete search history.

(56) References Cited

U.S. PATENT DOCUMENTS

| | | | |
|---|---|---|---|
| 5,103,811 A * | 4/1992 | Crupi, Jr. .............. | A61F 5/0125 602/26 |
| 7,473,235 B2 * | 1/2009 | Schwenn ................ | A61F 5/028 2/311 |
| 2003/0092545 A1 * | 5/2003 | Koscielny .......... | A63B 21/0004 482/124 |
| 2006/0200057 A1 | 9/2006 | Sterling | |
| 2007/0027419 A1 * | 2/2007 | Drennan ............ | A63B 21/4011 602/19 |
| 2011/0009790 A1 | 1/2011 | Brown | |
| 2013/0053743 A1 | 2/2013 | Reinhardt et al. | |
| 2013/0324899 A1 | 12/2013 | Lance | |
| 2013/0345612 A1 | 12/2013 | Bannister et al. | |
| 2014/0207040 A1 * | 7/2014 | Ingimundarson ..... | A61F 5/0193 602/23 |
| 2015/0272764 A1 * | 10/2015 | Kim .................... | A61H 1/0244 74/479.01 |
| 2017/0202724 A1 * | 7/2017 | De Rossi .............. | A61F 5/0102 |

OTHER PUBLICATIONS

International Search Report and Written Opinion in corresponding PCT Patent Application No. PCT/US18/37397, mailed Sep. 20, 2018 (12 pages).

* cited by examiner

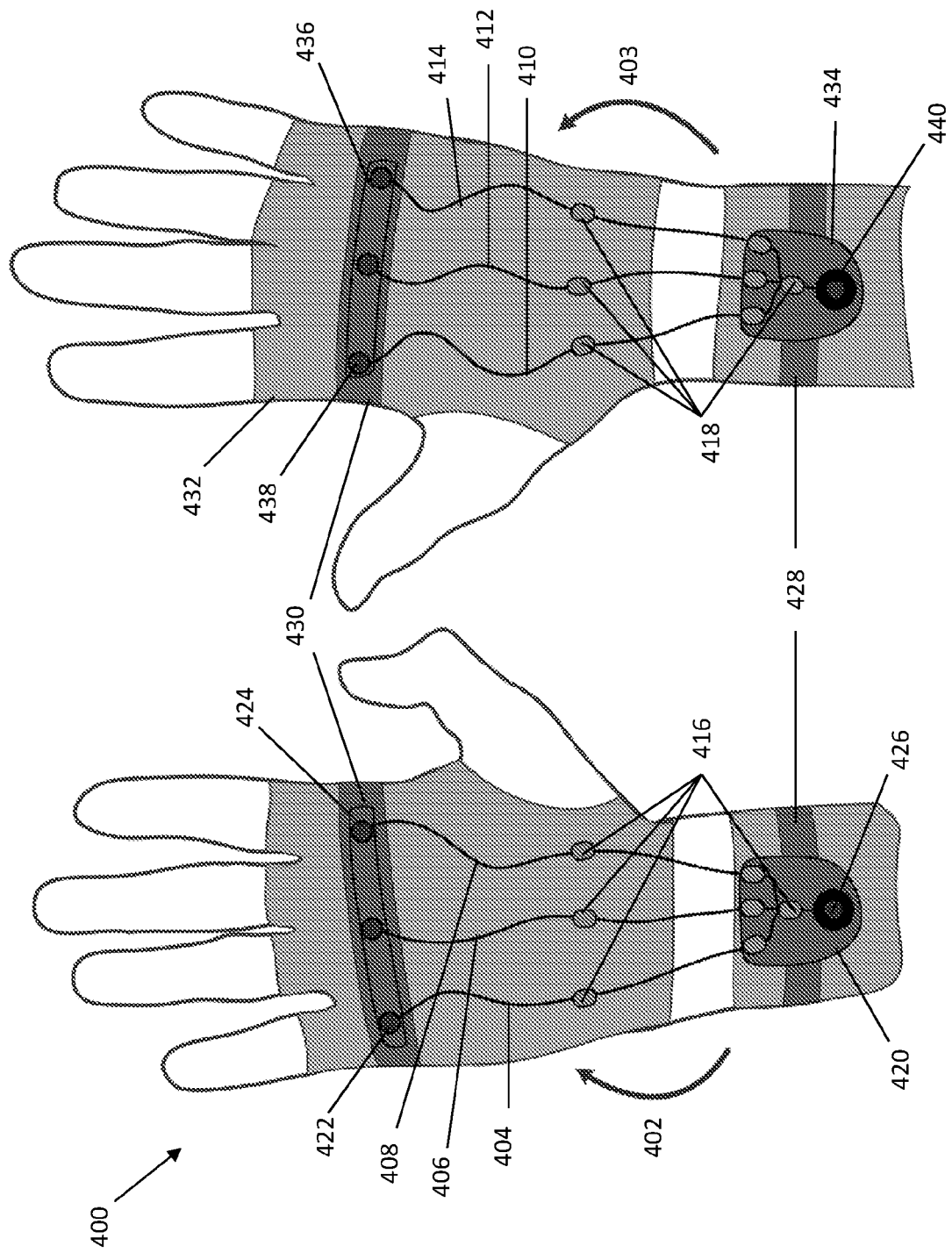

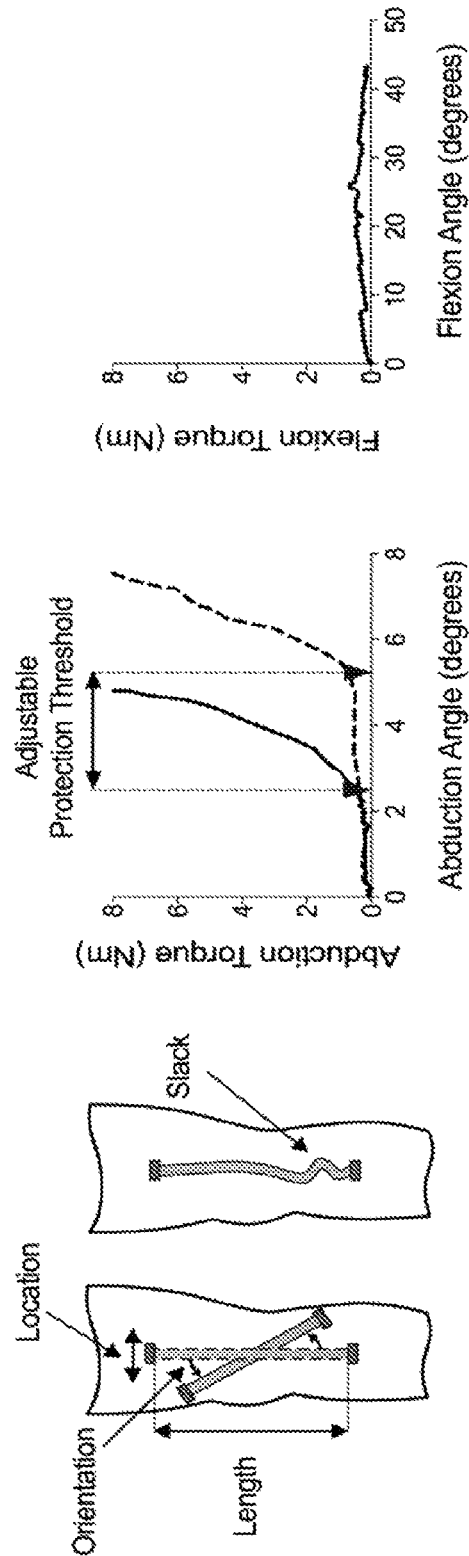

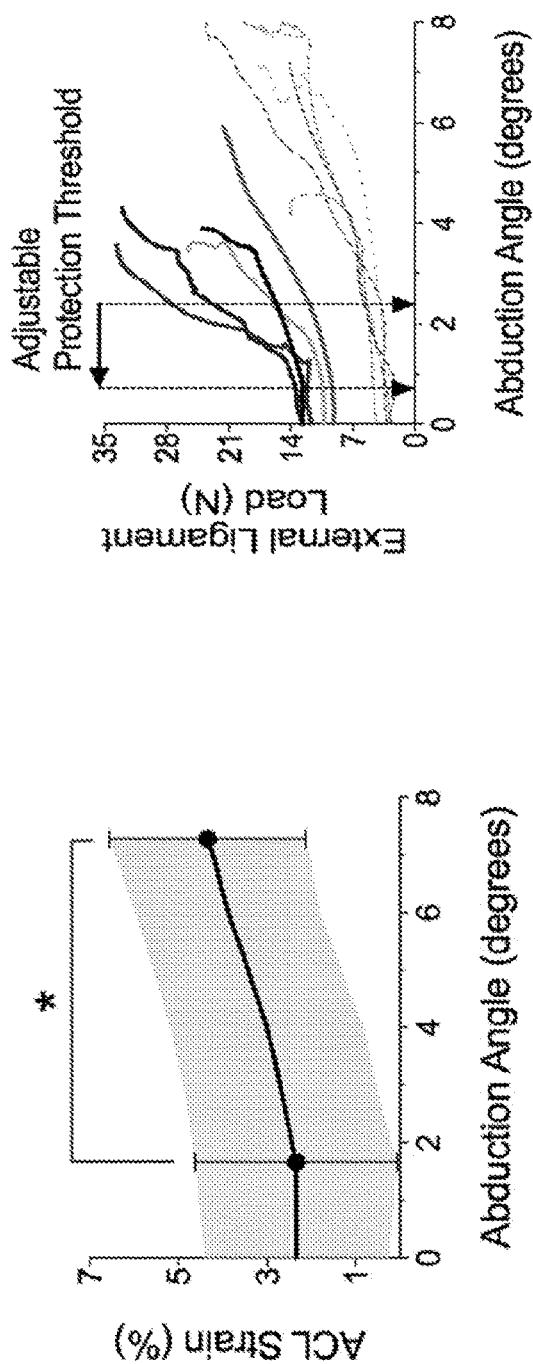
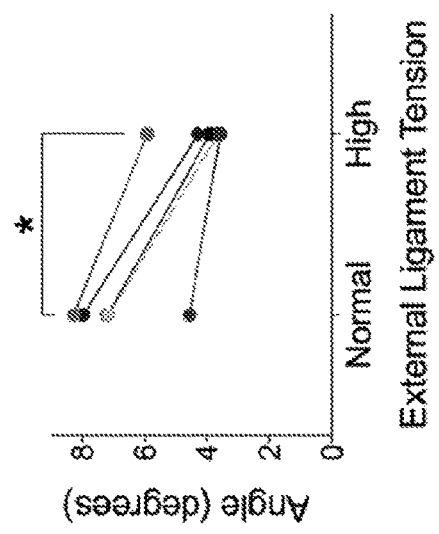
FIG. 37D
FIG. 37E
FIG. 37C

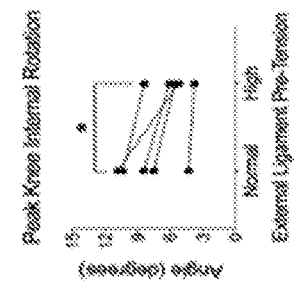
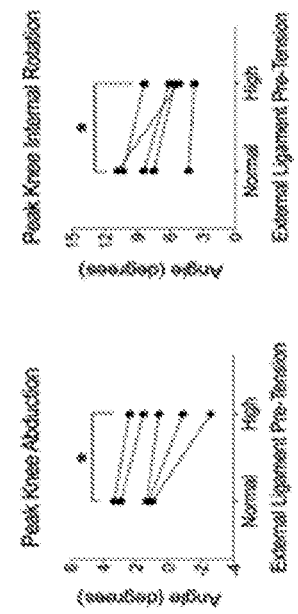
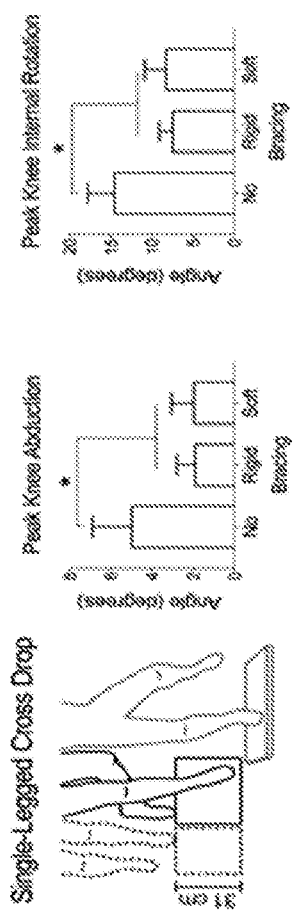
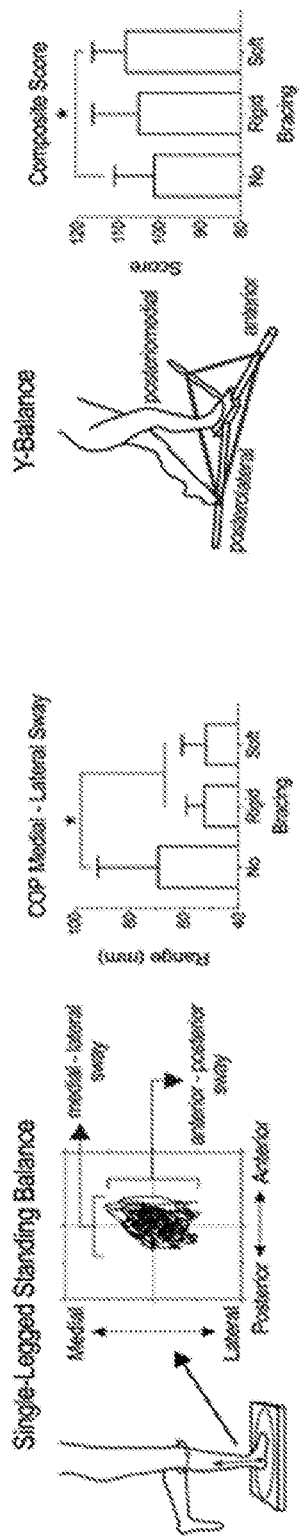
FIG. 38A  FIG. 38B  FIG. 38C  FIG. 38D  FIG. 38E  FIG. 38F

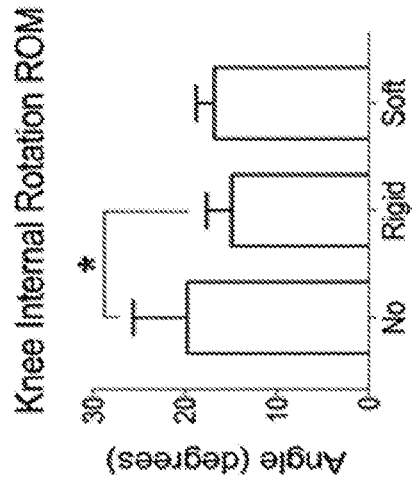
FIG. 39A
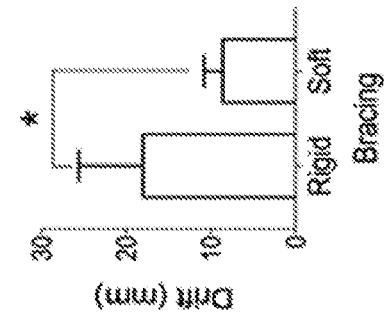
FIG. 39B
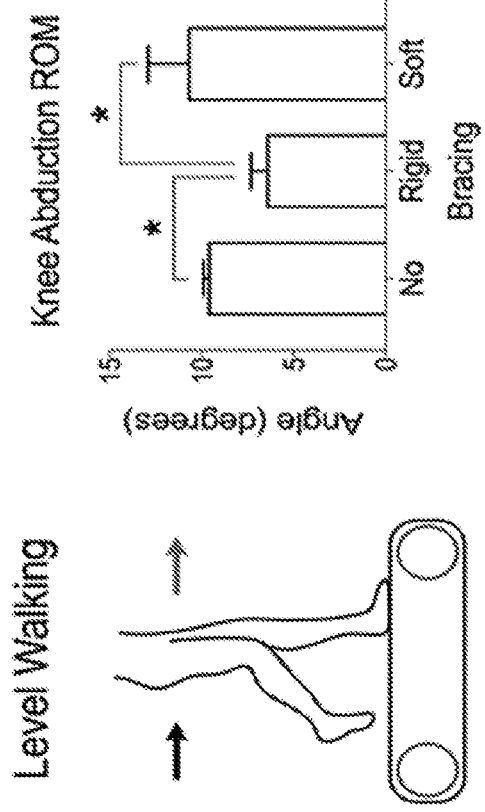
FIG. 39C
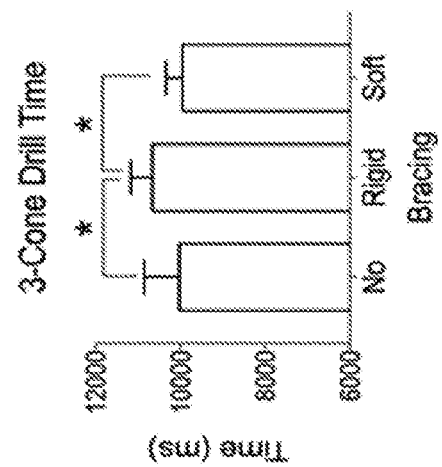
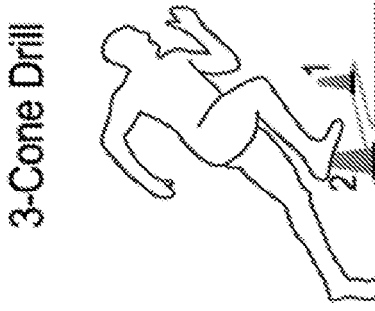
FIG. 39D

SOFT BRACES TO PREVENT INJURY TO A JOINT OR BODY SEGMENT

RELATED APPLICATIONS

This application is the U.S. national phase application, pursuant to 35 U.S.C. § 371, of PCT International Application No.: PCT/US2018/037397, filed Jun. 13, 2018, designating the United States and published in English, which claims the benefit of and priority to U.S. Provisional Application No. 62/519,079 filed Jun. 13, 2017, which is incorporated herein by reference in its entirety.

FIELD

The present disclosure relates to a soft bracing approach to protect joints against ligamentous injuries, and more particularly to a soft brace to prevent injury to one or more target joints or body segment.

BACKGROUND

Traumatic injuries of joint connective tissues (e.g. ligaments) are among the most common musculoskeletal conditions in adolescents and young adults participating in physically demanding activities such as sports and military operations. These injuries are often immediately disabling, expensive to treat and associated with lowered activity levels. They mostly occur due to poor mechanical control that leads to an excessive joint motion or loading. Prevention strategies focused on altering these high-risk kinematic and kinetic factors can effectively reduce the injury risk, and are an appealing option to avoid short- and long-term consequences of such injuries. One such approach is prophylactic bracing to limit the joint motion within the physiologic range.

As the largest joint in the body, the knee is essential for competing in almost every sport, but is also the most common site for injury in young athletes. Overall, knee injuries make up about 55% of all sports injuries. Every year, over 5 million people visit orthopedic surgeons for knee-related injuries and problems in the U.S. alone. In 2010, there were roughly 10.4 million patient visits to doctors' offices because of activity-related knee injuries including ligament tears and cartilage damage. Knee injuries are common in most sports including football, soccer, hockey, basketball, volleyball gymnastics, lacrosse, skiing and snowboarding.

The anterior cruciate ligament (ACL), a major contributor to knee stability and function, is one of the major ligaments located in the middle of the knee and runs from the femur (thigh bone) to the tibia (shin bone). The ACL is among the primary contributors to knee joint stability in all three anatomical planes. Injuries to the ACL are one of the most common and devastating knee injuries with approximately 400,000 ACL surgeries being performed each year in U.S. These injuries primarily target young, active individuals (15-25 years old). More than 70% of ACL injuries are non-contact (without a direct blow to the knee joint) and occur when an athlete changes direction quickly, stops suddenly, or lands from a jump. An injured ACL has poor healing capacity and frequently requires surgery to replace the torn ligament with a tendon graft (ACL reconstruction, the current standard of care). Physical therapy is also necessary to rehabilitate the knee. It is usually at least six to nine months before athletes can return to their normal activity level.

ACL injuries have both short- and long-term clinical sequelae including joint effusion, altered movement, muscle weakness, reduced functional performance, increased risk of re-injury, and prolonged loss of sports participation among young athletes. ACL injuries are among the leading causes of posttraumatic knee osteoarthristis (OA) and have been associated with earlier need for knee replacement, even after ACL surgery. Using a conservative cost estimate of USD 17,000-USD 25,000 per patient for surgery and rehabilitation, the estimated cost for treatment in ACL-injured patients in the United States is over USD 1.7 billion annually. This estimate does not consider the resources necessary for non-surgical treatment, or to treat the long-term complication of post-traumatic OA associated with both the ACL-injured and ACL-reconstructed knee. Moreover, the long-term arthrosis associated with ACL injury can result in lowered activity levels, and long-term disability, which can result in significant socio-economic burden.

Knee injuries are one of the most common (20% of all injuries) and devastating injuries suffered in football. A recent survey of 293 NFL players shows that 46% of players are concerned about injuries to their knees and lower extremities, while only 24% are concerned about injuries to other parts of the body. Injuries to the ACL comprise the majority of knee injuries among NFL players with an average of 43 ACL tears each season. 65 ACL injuries were in 2013 season alone. These injuries are associated with lower activity levels and potential loss of the entire season, low rate of return to play (by 40%), shortened athletic career (by 2 years) and substantial short-term financial loss. Most importantly, athletes that have experienced these injuries are at significantly greater risk of knee osteoarthritis (by as much as 78%), a disease 3 times more prevalent in former NFL players than the general population, even after surgical treatment. Recent studies have shown arthritis to be the most prevalent (67%) health complication (predominantly in the knee joint) and also the most striking determinant of decreased SF-36 physical health score (by 21%) among retired NFL players.

Injury prevention (for example, prophylactic bracing) is currently the only effective intervention to avoid short- and long-term complications linked to ACL injuries. Prophylactic knee bracing was introduced almost three decades ago to reduce the risk of ligamentous injuries during athletic activities. The design principal of these braces includes metal-hinged single or dual uprights embedded in a rigid frame to provide resistance against valgus stress. Despite evidence of reduced ACL injury risk, the efficacy and popularity of prophylactic knee bracing has not become mainstream among athletes. This lack of interest and low acceptance rate can be related to substantial discomfort, lowered athletic performance and increased fatigue often caused by existing bracing technologies.

More than 5 million knee braces and supports were sold in the US in 2011, many of which were for knee-related sports injury. The report by Marketstrat Inc. highlights the following key trends and characteristics of the U.S. market for orthopedic braces and supports: knee bracing accounts for the largest share of revenue. The US market for knee braces and supports is expected to exceed USD 1.2 billion in revenue by 2018. Consumers are willing to pay out-of-pocket for many products; off-the-shelf soft braces and supports for pain relief and protection offer good alternatives to prescription products.

Valued at USD 2.3 billion in 2013, the global orthopedic braces and supports market is expected to continue growing as physician and patient adoption increases, according to GlobalData. The global orthopedic braces and support market was valued at USD 3.2 billion in 2014 and is expected to reach USD 4.3 Billion by 2020, at a compound annual growth rate (CAGR) of 5.0% from 2015 to 2020. Based on end users, the global orthopedic braces market has been segmented into orthopedic clinics, over-the-counter (OTC), hospitals, and other end users. In 2014, the orthopedic clinics segment accounted for the largest market share, followed by the OTC segment. It is expected to grow at CAGR of 4.3% from 2015 to 2020. The OTC segment is projected to grow at the highest CAGR of 6.1% from 2015 to 2020. The large growth of the orthopedic clinics segment can be attributed to the fact that patients with painful conditions prefer consulting orthopedicians rather than directly visiting hospitals. There is a growing demand from clinicians for braces and supports that are injury- or surgery-specific, especially for knees, ankles, and shoulders.

The global orthopedic brace market has been categorized into major geographical regions: North America, Europe, Asia, and rest of the world. North America is the most dominant region in the global orthopedic braces market, contributing a share of 47.4% in 2014; the market in the North America region was valued at USD 1.5 billion in the same year.

Various bracing techniques have been used to stabilize the knee joint and reduce the injury risk (sleeves and prophylactic rigid braces), support injured unstable joint (functional rigid braces), and help injured knees to heal after surgery (rehabilitative braces). Among these, only sleeves and prophylactic braces are designed to protect the knee against injuries. Sleeves are mainly used during daily low-risk activities (i.e. walking and running) and prophylactic braces are mainly used during more intense, high-risk sport activities like football (Table 1, showing brace types used to prevent knee injuries). Despite the proven role of bracing in protecting the knee against excessive joint motion/loading, the efficacy and popularity of these devices has not become mainstream in sports like football. This is because current protective knee braces are associated with poor resistance of the impulsive and multi-planar loading that leads to knee injuries, substantial discomfort, lowered athletic performance, and increased fatigue.

anchor one or more of the one or more tensile elements to the body to provide force distribution relative to the one or more target joints.

In some embodiments, the one or more tensile elements can provide customizable protection to the one or more target joints by providing customizable resistance against motion of the target joint. The one or more tensile elements have a length at rest and a length in motion such that the one or more tensile elements provide tension during motion. In some embodiments, at least one of the one or more tensile elements is routed in parallel with the approximate center of rotation of at least one of the one or more target joints.

In some embodiments, the soft brace can include an adjustment mechanism configured to customize the amount of resistance against motion imposed on the one or more target joints. In some embodiments, the adjustment mechanism can customize the amount of resistance manually such that the length of the one or more tensile elements is configured to be adjusted to customize the amount or resistance against motion. In some embodiments, the adjustment mechanism can customize the amount of resistance automatically using at least one of motors, sensors, and actuators such that the length of the one or more tensile elements is configured to be adjusted to customize the amount or resistance against motion. For example, a tension level of the one or more tensile elements can be gradually and continuously controlled using a passive mechanical system. In some embodiments, a tension level in at least one of the one or more tensile elements can be adjusted to provide a predefined resistance against a motion of the target joint.

In some embodiments, the soft brace can include a guiding system configured to route the one or more tensile elements across the brace to maintain the orientation of the one or more tensile elements during a range of motion of the one or more target joints. In some embodiments, the guiding system can be configured to route at least one of the one or more tensile elements through the approximate center of rotation of at least one of the one or more target joints.

In some embodiments, the brace can be configured to provide dynamic joint protection such that the brace is configured to protect the one or more target joints during

TABLE 1

| Brace Type | Protection Level | **Reported Benefits | **Limitations |
|---|---|---|---|
| Sleeve | Low | Lowered injury risk/severity during low risk activities | Limited support during high-risk activities and thus ineffective at preventing knee injuries |
| Prophylactic or functional rigid braces | High | Preventing MCL injuries or supporting week joints | Restrictive, uncomfortable and heavy and thus not commonly used during high-risk activities due to on player performance |

SUMMARY

Soft braces to prevent or reduce injury to one or more target joints or a body segment are disclosed. In some aspects, a soft brace for a target joint or a body segment is provided that can include one or more tensile elements configured to limit motion of one or more target joints based on placement of the one or more tensile elements relative to the one or more target joints such that the placement of the one or more tensile elements and a tension of each of the one or more tensile elements provides resistance against motion of the one or more target joints. One or more soft tissue anchors can be positioned on a body around the one or more target joints. The one or more anchors are configured to excessive movement without affecting the motion of the one or more target joints during normal movement. In some embodiments, the brace can be configured to provide targeted joint protection such that the brace is configured to protect against an excessive range of motion in one or more degrees of freedom.

In some embodiments, at least a portion of the one or more soft tissue anchors include semi-rigid non-textile components. In some embodiments, the one or more soft tissue anchors are in the form of compression mechanisms.

In some embodiments, the brace can include one or more sensors to provide feedback on the tension of the one or more tensile elements. In some embodiments, the brace can include dynamic control in the form of one or more sensors configured to measure activity of the one or more target joints to provide feedback in real time regarding at least one of the load and motions of the one or more target joints. In some embodiments, one or more motors can be configured to control tension in the one or more tensile elements based on feedback information from the one or more sensors.

In some embodiments, the soft brace can include one or more remote joint anchors positioned remote from the one or more target joints. The one or more remote joint anchors can be configured to couple one or more of the one or more tensile elements to a remote joint to provide force distribution relative to the one or more target joints. In some embodiments, the soft brace can include one or more flexible hinges that are configured to bend to provides resistance against motion of the one or more target joints.

In some embodiments, the one or more target joints can include a knee joint. The one or more tensile elements can be configured to extend from a positioned proximal the knee joint to a position distal the knee joint such that the one or more tensile elements extend around at least one of medial and lateral aspects of the knee joint to provide resistance against knee rotation in at least one of frontal and transverse planes.

In some embodiments, the one or more target joints can include an ankle joint. The one or more tensile elements can be configured to extend from a positioned proximal the ankle joint to a position distal the ankle joint such that the one or more tensile elements extend around at least one of medial and lateral aspects of the ankle joint to provide resistance against at least one of ankle inversion and eversion of the ankle joint.

In some embodiment, the one or more target joints can include a shoulder joint. The one or more tensile elements can be configured to extend from a positioned proximal the shoulder joint to a position distal the shoulder joint such that the one or more tensile elements are configured to provide resistance against targeted motion of the shoulder joint.

In some embodiments, the one or more target joints can include a back joint. The one or more tensile elements can be configured to extend from around a torso from a position on the front of the torso to a position on the back of the torso such that the one or more tensile elements are configured to provide resistance against at least one of thoracic spine motion and lumbar spine motion.

In some aspects, a soft brace for a target joint or a body segment is provided that can include one or more tensile elements configured to limit motion of a body segment based on placement of the one or more tensile elements relative to the body segment such that the placement of the one or more tensile elements and a tension of each of the one or more tensile elements provides resistance against motion of the body segment. One or more soft tissue anchors can be positioned on a body around the body segment. The one or more anchors are configured to anchor one or more of the one or more tensile elements to the body to provide force distribution relative to the body segment. One or more remote joint anchors can be positioned remote from the body segment. The one or more remote joint anchors are configured to couple one or more of the one or more tensile elements to a remote joint to provide force distribution relative to the body segment.

In some aspects, a soft brace for a target joint or a body segment is provided that can include one or more tensile elements and one or more flexible hinges configured to limit motion of one or more target joints based on placement of the one or more tensile elements and one or more flexible hinges relative to the one or more target joints such that the placement of the one or more tensile elements and one or more flexible hinges and a tension of each of the one or more tensile elements and the bending of each of the one or more flexible hinges provides resistance against motion of the one or more target joints. One or more body anchors can be positioned on a body around the one or more target joints. The one or more anchors are configured to anchor one or more of the one or more tensile elements and one or more flexible hinges to the body to provide force distribution relative to the one or more target joints.

In some embodiments, an adjustment mechanism can customize the amount of resistance manually and/or automatically using motors, sensors, and actuators such that the number, design or structural properties of the one or more flexible hinge and/or the length of the one or more tensile elements is configured to be adjusted to customize the amount or resistance against motion.

In some aspects, a soft brace for a target joint is provided that can include a first tensile element positioned along a limb and routed through an inner medial aspect of the limb. The first tensile element is configured to allow for flexion motion of the target joint while limiting abduction motion of the target joint, the target joint being a knee joint. A first soft tissue anchor can be positioned proximal of the target joint, and a second soft tissue anchor can be positioned distal of the target joint such that a proximal end of the first tensile element is coupled to the first soft tissue anchor and a distal end of the first tensile element is coupled to the second soft tissue anchor. A first remote joint anchor can be positioned proximal of the first soft tissue anchor and configured to couple to the first soft tissue anchor through a second tensile element to provide distribution of force external to the target joint, with the first remote joint anchor being positioned at a joint adjacent the target joint. A tension in the first tensile element is adjustable to customize the amount of motion restriction imposed on the target joint.

In some aspects, a soft brace for a target joint or a body segment is provided that can include one or more tensile elements configured to limit motion of one or more target joints based on placement of the one or more tensile elements relative to the one or more target joints. The placement of the one or more tensile elements and a tension of each of the one or more tensile elements provide resistance against motion of the one or more target joints. The brace can also include one or more soft tissue anchors positioned on a body around the one or more target joints. The one or more anchors is configured to anchor one or more of the one or more tensile elements to the body to provide force distribution relative to the one or more target joints. One or more sensors can be configured to provide feedback on the tension of the one or more tensile elements.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 28A and FIG. 28B illustrate front and back views of an exemplary embodiment of a soft joint brace for protecting a hand and/or wrist;

FIGS. 34A, 34B, 34C, and 34D illustrate an embodiment of a mechanical assessment of a soft bracing approach relating to ACL injuries;

FIGS. 37A, 37B, 37C, 37D, and 37E illustrate soft brace function of a knee under various conditions;

FIGS. 38A, 38B, 38C, 38D, 38E, and 38F illustrate relative biomechanical efficacy of soft bracing;

FIGS. 39A, 39B, 39C, and 39D illustrate relative effect of soft bracing on normal joint function and joint function during athletic activity.

Figure 1:
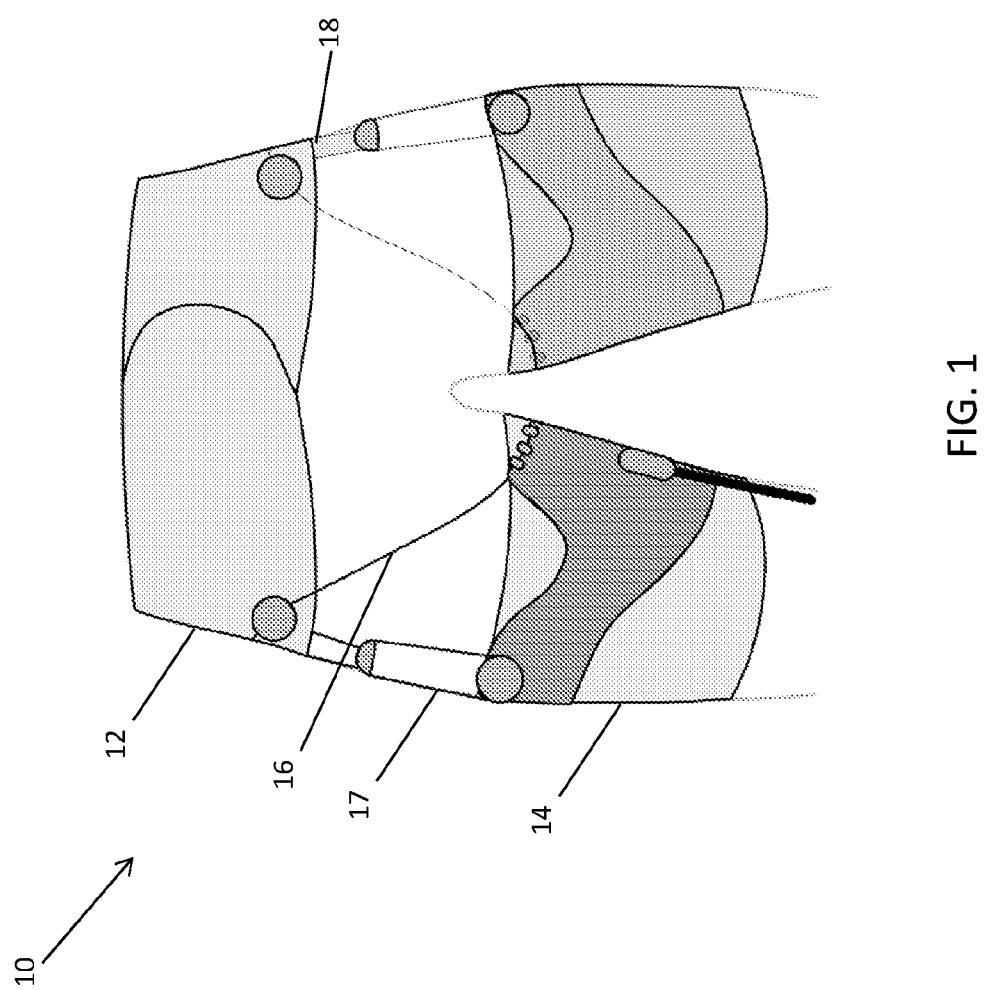
FIG. 1 illustrates an embodiment of a soft joint brace.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments.

Specific details are given in the following description to provide a thorough understanding of the embodiments. However, it will be understood by one of ordinary skill in the art that the embodiments may be practiced without these specific details. For example, systems, processes, and other elements in the presently disclosed embodiments may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure relates to a soft joint brace that provides protection to one or more joints, or a body segment, against injuries, including soft tissue injuries during activity. In some embodiments, certain motions are limited but other motion is not restricted. One or more tensile elements can span a joint in specific positions and orientations to protect the joint against excessive rotations in some directions without affecting motion in other directions. These tensile elements are triggered by excessive rotation after a certain threshold, and then dissipate resistive forces among anchor points on the body. Tensile elements can be made of a variety of types of materials, including high-stiffness inextensible materials (e.g. cables, similar to what has been used in the current prototype) or more advanced alternatives including but not limited to multi-stiffness materials (e.g. composites) with varying stiffness (protection level) depending on the amount of rotation/tension (e.g. increase stiffness under higher tensions) and/or loading rate (e.g. low stiffness under low-rate loading but turning rigid under high-rate loads). Such alternatives also include the tensile elements filled with magnetorheological fluid that offers varying stiffness levels by changing the fluid viscosity using actively controlled magnetic fields. In some embodiments, one or more flexible hinges can be used with or without one or more tensile elements to resist motion of a joint or body segment.

Distribution of the force among several components can be achieved. In some embodiments, a soft brace can distribute force over multiple components, located remotely from the targeted joint.

Figure 6:
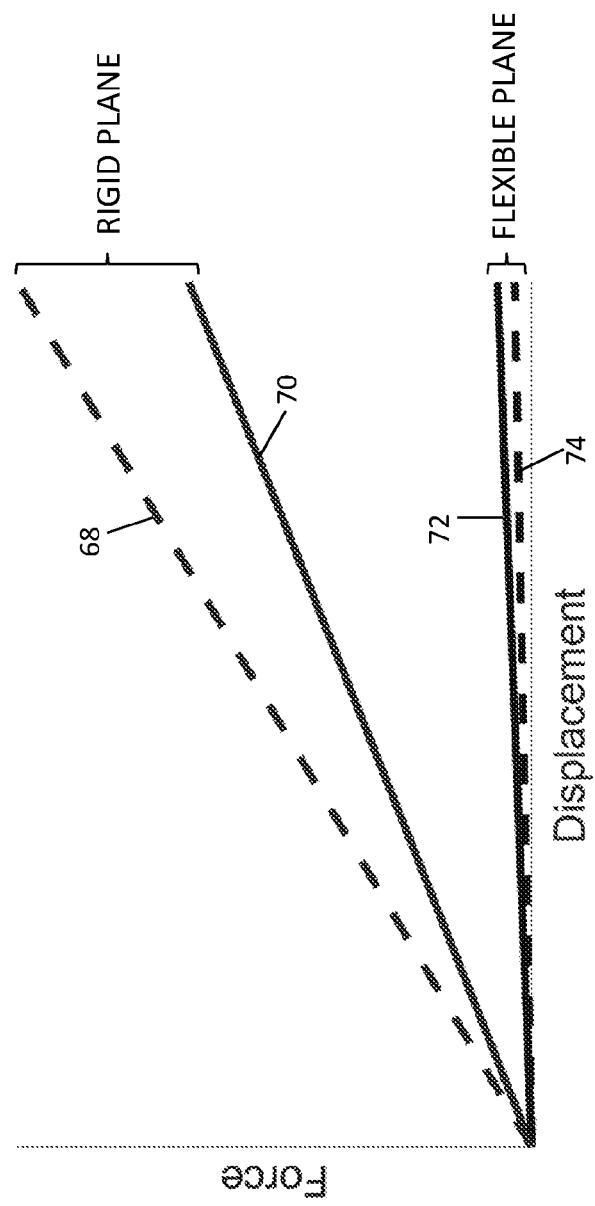
FIG. 6 illustrates an exemplary graph of displacement versus force relating to hinge stiffness.

In some embodiments, guiding systems (e.g. tubes, channels, pulleys, etc.) can be used to rout the tensile element(s) through specific orientations to limit desired range of motion. It can be important to maintain the orientation of the tensile element(s) during range of joint motion. In some embodiments, a guiding system can run a tensile element through the approximate joint center of rotation. It can be important to keep constant tension of the protective cable during full range of rotation (for example, knee flexion). A mechanical guiding system can be used to rout cable through the approximate center of the joint (FIG. 6). The guiding system can be attached to the brace anchors above and/or below the joint.

Figures 7A, 7B:
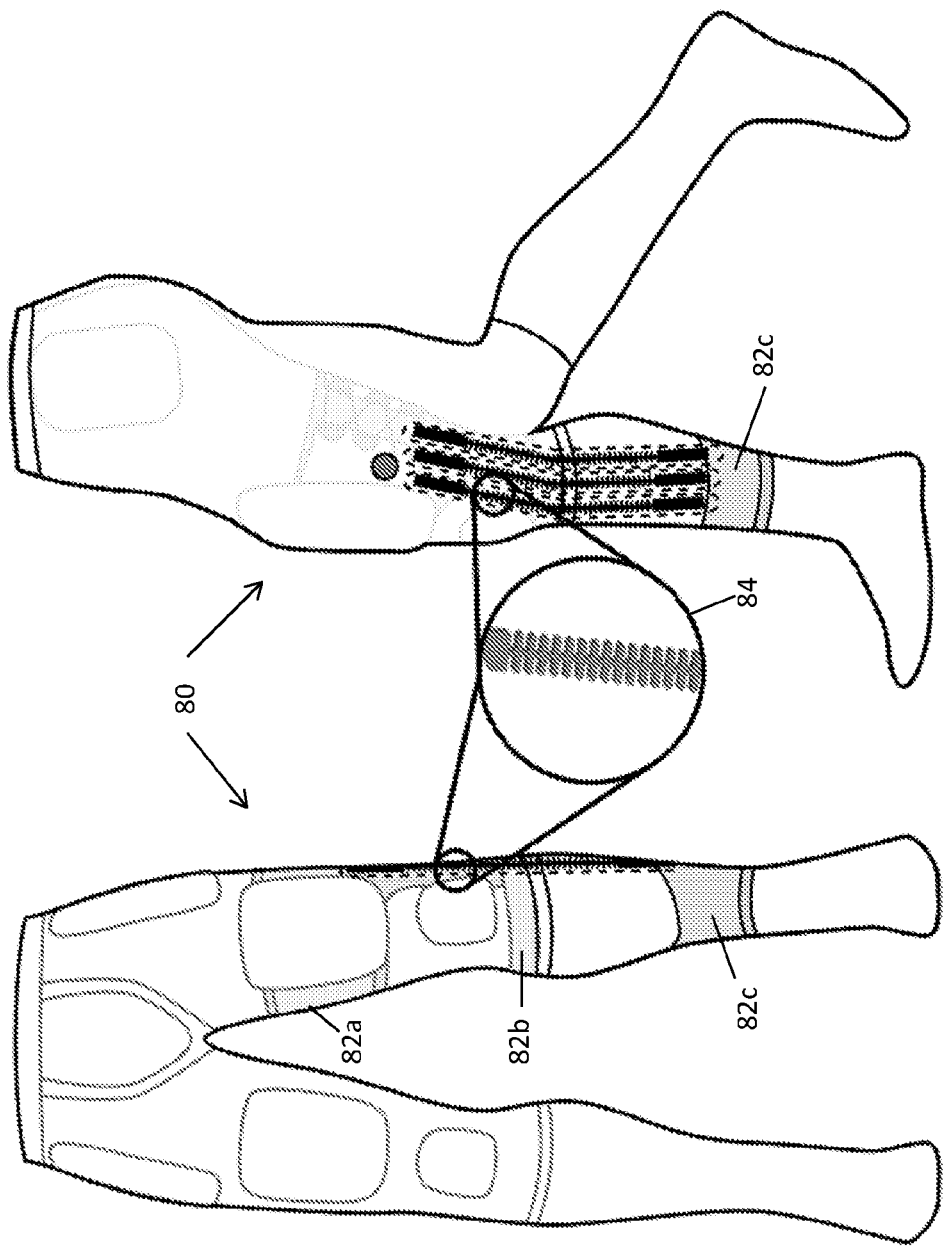
FIG. 7A and FIG. 7B illustrate embodiments of a soft joint brace with one or more flexible hinges.

In some embodiments, one or more semi-rigid non-textile components (for example, plates, plastic plates) can be used to increase stability for anchoring the tensile elements and improving force distribution. Integration of semi-rigid components into the fabric with a strategic placement can enable stability/base for cable anchoring to the soft structure (FIGS. 7A-7B).

In some embodiments, a soft brace can provide protection of multiple degrees of freedom. By increasing a number of tensile elements and/or flexible hinges or changing the placement and/or orientation of tensile elements and/or flexible hinges, it can determined which and how many degrees of freedom (joint motions) can be affected.

Soft bracing and targeted protection can be used for a variety of purposes. The platform can be used to design protective gears (e.g. braces) to lower a risk of musculoskeletal injuries that occur due to excessive motion (i.e. joint rotation or translation) during variety of activities/events (i.e. walking, sports, etc.). Some of these applications include but not limited to the protection of frequently injured joints, such as shoulder, elbow, hip, ankle and neck, the protection against muscle injuries, such as hamstring tears, and multi joint (for example, whole body) protection. In some embodiments, a suit can be provided that includes several tensile elements run in specific orientation across specific parts of the body, protecting multiple joints against excessive movements.

A soft joint brace can be used to provide support and/or protection to various parts of the body, including but not limited to the knee, shoulder, hip, hand/wrist, ankle, spine, and whole body support. For example, in the case of a knee joint, the soft brace can protect against various injuries, including but not limited to ACL tears, meniscus injuries, injuries to the medial collateral ligament (MCL) and injuries to the posterior cruciate ligament (PCL). In some embodiments, a soft brace can be achieved through functional apparel with integrated force transmitting elements that can offer targeted and customizable joint (for example, knee) protection without disrupting athletic performance.

The soft joint brace can include a variety of features to provide injury protection and/or prevention. In some embodiments, the brace can include one or more soft conformable anchors (for example, wraps) that can be secured to the body by means of compression though a variety of techniques, including but not limited to Velcro, pre-tensioning cables, or any similar approach. One or more high strength flexible materials, or tensile elements, can be attached to the soft anchors in a variety of specific configurations to resist body (joint) motion in a pre-specified direction without affecting other degrees of freedom. These high strength flexible load bearing components of the brace (for example, tensile elements or external ligaments) can be made of single-stiffness or varying stiffness (for example, rate-dependent) cables or ropes, ribbons, springs, and composite structures including but not limited to those made of plastics and polymers, metals, fabrics and fluids (for example, shear thinning and magnetorheological fluids). It will be understood that the tensile element can also be referred to as an external ligament, a cable, an external cable, an external ligament module, a protective cable, or a protective fiber.

One or more tensile elements (for example, made from high strength flexible materials) can be attached to the soft anchors in a variety of specific configurations to distribute the loads generated across the external ligaments along multiple brace parts. They also help to keep the brace soft anchors (wraps) in place and improves brace stability (for example, the infinite loop for anchoring the thigh wrap to the waist belt as shown in FIG. 1). These loadbearing components can be made of single-stiffness or varying stiffness (e.g. rate-dependent) cables or ropes, ribbons, springs, and composite structures including but not limited to those made of plastics and polymers, metals and fabrics.

Figures 16A, 16B:
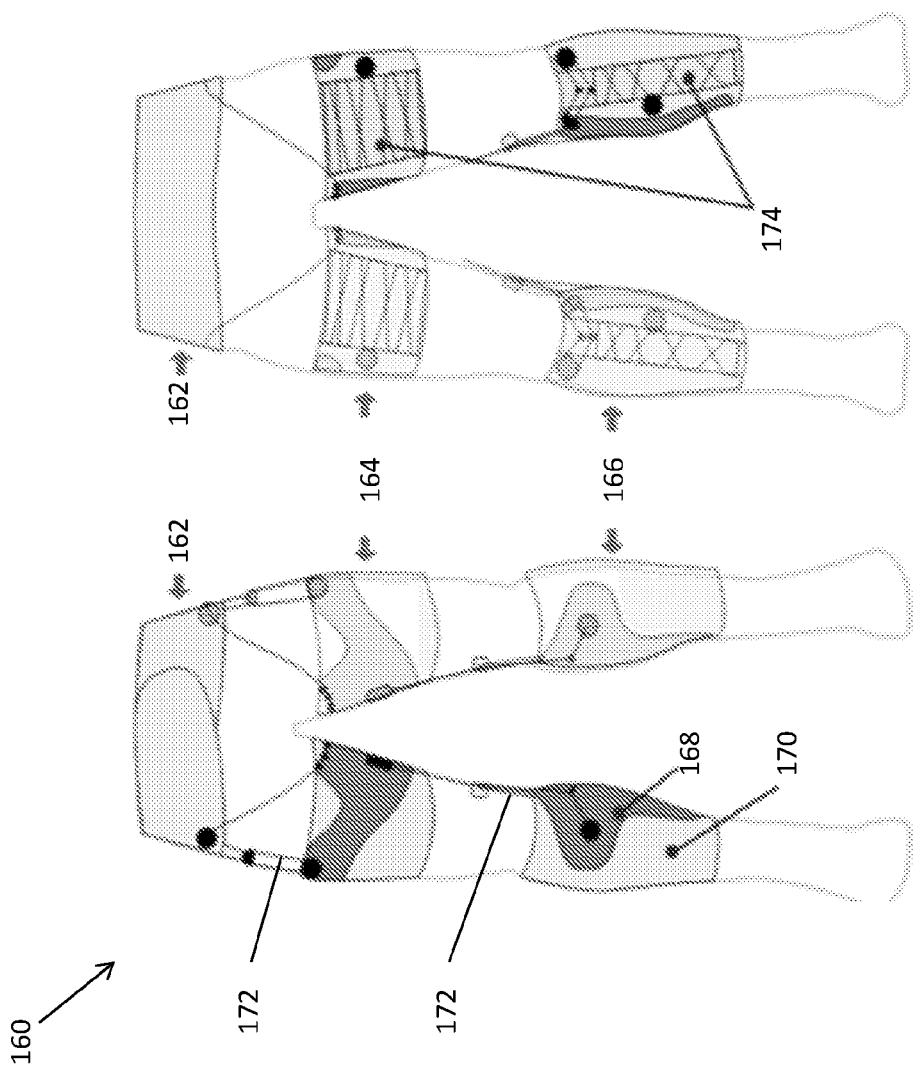
FIG. 16A and FIG. 16B illustrate front and back views of an embodiment of a knee soft joint brace.

In some embodiments, tensile (or cable) element based force transmission system can remain constant tension through the full range of joint motion, such as hip motion. Forces triggered by excessive joint motion can distribute between multiple soft anchors, such as a thigh anchor and a hip anchor, by the means of a plurality of tensile elements. FIG. 1 shows an example of distributing the forces generated by excessive knee motion between thigh and waist anchors in a soft knee brace. The device shown in FIG. 1, is a soft joint brace 10 in the form of a continuous or infinite loop (as indicated by an arrow), that can be used to attach a waist anchor 12 to a thigh anchor 14. In order to distribute forces evenly and avoid tilting/migration, tensile elements 16, 17, 18 anchor on the inner and outer sides of the thigh component for counter action. While an outer tensile element can remain a constant length to keep constant tension through the full hip motion, an inner cable has to change its length somehow to keep constant tension due to the body kinematics. A dynamic loop (infinite loop) can be implemented going around the thigh and anchor it to the hip outer side and thigh inner side by means of a Bowden sheath (as shown in FIGS. 1 and 16A-16B). The sheath itself remains fixed permanently, while tensile cable runs through the sheath around the thigh and changes length on front and back dynamically so the tension remains constant. In some embodiments, the device can include a vertical support strap to represent force distribution between thigh and waist anchors, as shown in FIG. 1.

Figure 2:
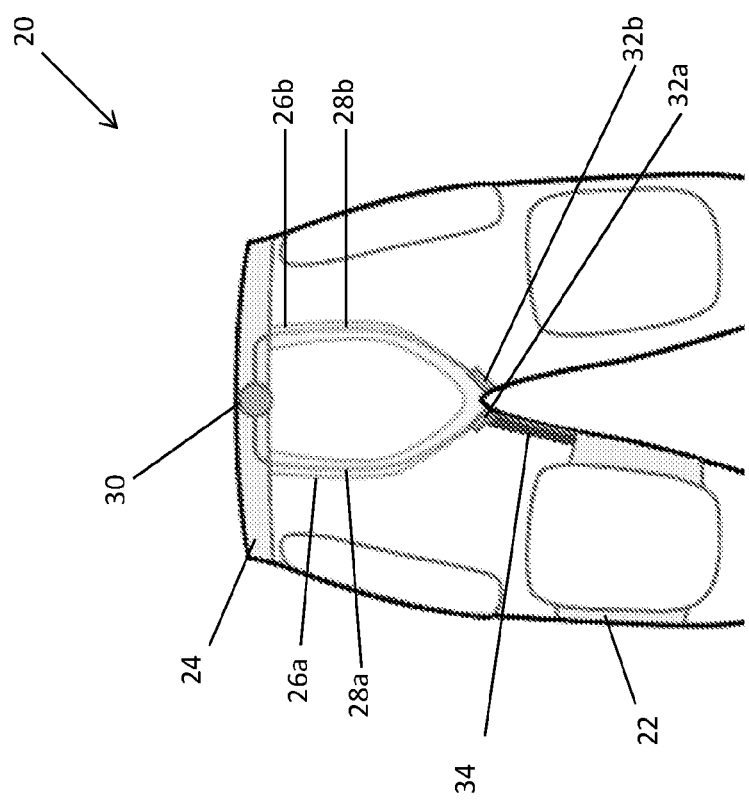
FIG. 2 illustrates an embodiment of a soft joint brace.

In some embodiments, as shown in FIG. 2, the length of the anchor support cables can remain constant to provide a constant force distribution between the thigh and waist anchors throughout a full range of hip motion. As shown in FIG. 2, a soft joint brace 20 can include inextensible textiles including a thigh anchor 22, a waist anchor 24, and channels 26a, 26b, through which anchor support cables 28a, 28b can run. An adjustable dial 30 can be used to adjust the tension in the cables 28a, 28b, and cable guides 32a, 32b can be used to assist with the placement of the cables 28a, 28b. The brace 20 can also include an anchor support cable 34 that run between the cable guide 32a and the thigh anchor 22. This can have a similar function as the infinite loop.

In some embodiments, a brace can also include a guiding system (for example, tubing, channelling) to rout the load-bearing components of the brace (for example, tensile elements) in various pre-determined configurations to resist a pre-specified range of motion without affecting other motions (degrees of freedom) in the joint. The guiding system can include, but is not limited to, plastic, fabric or metal tubes (channels), pulleys or any other position adjusting devices (for example, the centering piece can be used in a brace, for example a knee brace, to keep the tensile element passing through the approximate knee center of rotation) that can be embedded in or connected to the soft anchors (also referred to as wraps, soft tissue anchors, or body anchors) using a variety of techniques, including sewing, gluing, or any other method that can couple the guiding system to the soft anchors.

The soft anchors can also include features to increase stability provided to the body. In some embodiments, one or more flexible, semi-rigid or rigid non-textile components (i.e. metal, plastic or polymer plates) can be attached to or embedded in the brace soft anchors (wraps) to locally increase the apparel stiffness and to provide a stable area for anchoring the loadbearing components of the brace (for example, tensile elements). They can conform to the body curvature and contribute to brace stability, function and comfort by improving brace-body load transfer. It will be understood that the soft anchors can also be referred to as anchors, body anchors, or soft tissue anchors.

The soft anchors, or semi-rigid non-textile components, can enable lower levels of compression to be used to anchor securely to the body and resist forces applied by one or more tensile elements, or cables. The use of the semi-rigid non-textile components can impact wearer comfort, since the brace doesn't have to be tightened extremely and therefore does not restrict muscles functions. The semi-rigid non-textile components, or plates, can also provide a stable area/base for anchoring of the primary loadbearing modules (for example, tensile elements). The semi-rigid non-textile components can have a variety of configurations, and they can be flexible and/or shaped so as to conform to the body curvature to ensure a comfortable brace-body interface that can effectively transfer the loads generated across the loadbearing components of the brace to the body. For example, the semi-rigid non-textile components do not have to be flexible if they fit the anatomy of the body well. The semi-rigid non-textile components can be attached to the apparel via a variety of means, including but not limited to sewing, bonding, forming, heat pressing, or seating in a pocket. Additionally, the semi-rigid non-textile components can also help to distribute pressure applied over larger areas of the body. These components (whether flexible or rigid) directly influence the brace function in resisting unwanted motion, brace stability and drift, and brace comfort by providing a stable anchoring area to distribute the loads generated in the brace across the body, stabilizing loadbearing components of the brace, and/or improving brace to body load interface.

The shape of the semi-rigid non-textile components can be determined by a variety of factors, including a minimum size required to provide stability, area of placement (for example, soft tissues or bone), number of tensile elements or cables being anchored, and/or direction of force applied. In some embodiments, each component can be cut to shape and heat-formed around a portion of the body, for example the thigh or calf, to improve the brace-body interface (for example, allowing better conformity around the leg muscles). The semi-rigid non-textile components can be shaped in a way to provide a stable anchoring without compromising the ability of the soft anchors to conform around the body. In some embodiments, specific considerations for shaping these plates were to cover the areas under each length adjustment mechanism (for example, ratchet dials) and to possibly avoid interfering with muscles contraction. Other considerations and approaches can be used to shape the semi-rigid non-textile components.

In some embodiments, the anchors can be constructed such that it can distribute pre-compression and/or applied forces to minimize pressure points on underlying body tissues, thus reducing risk of injury and enhancing comfort, and/or it can improve an interface between the anchor and the wearer's body, in terms of frictionally engaging the body part for preventing migration of the anchor, and also in terms of sweat wicking or breathability. The shape of the anchor can also effect migration of the anchors. In some embodiments, conical-shaped anchor can be used, as the tapered shape can resist slippage of the anchor relative to the body in the direction of the larger end by mechanically locking with the underlying musculature and/or skeletal structure.

Figure 3:
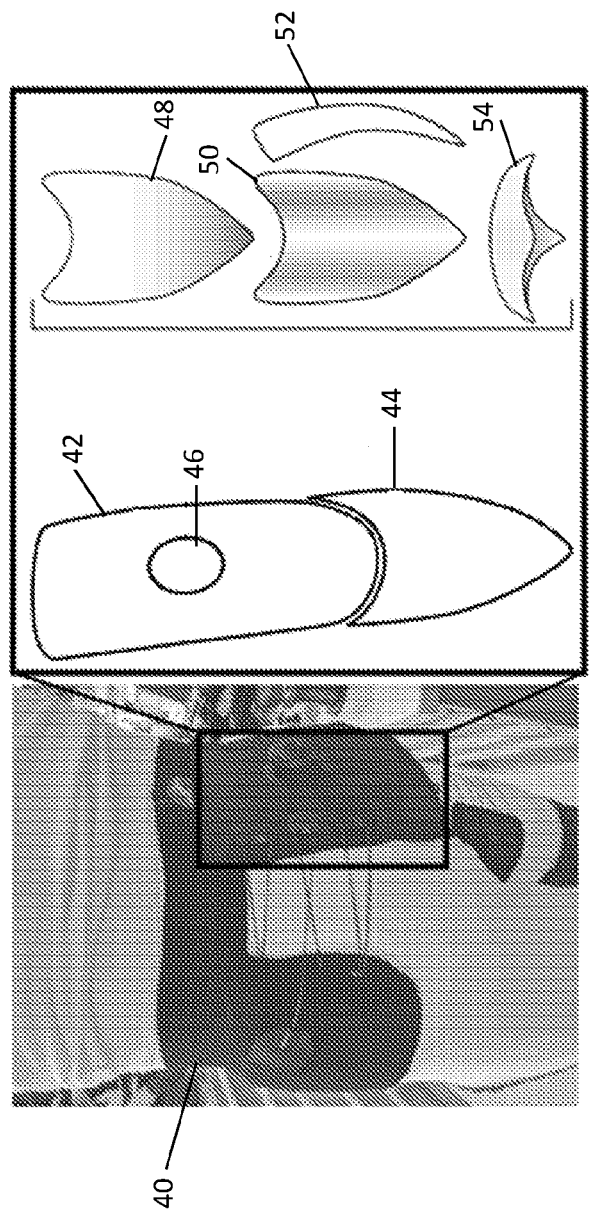
FIG. 3 illustrates an embodiment of a soft joint brace having foam segments.

The material forming portions of the anchor can also vary. In some embodiments, portions of the anchor can be made from any textile or similar material having sufficient flexibility for accommodating flexing and other movements associated with the tissue, underlying muscles, joints, etc. of the body part, while still having sufficient shear strength to resist significant deformation under applied loads. Example materials include, without limitation, neoprene, open or closed cell foam, or mesh spacers, amongst other suitable materials or combinations thereof. Sweat and temperature management may be of concern when dealing with long term wear of various components of a soft brace. In some embodiments, a portion of an anchor can include a breathable mesh or mesh spacer to reduce incidence of sweating. A portion of the anchor can additionally or alternatively include other breathable, perforated, or sweat-wicking materials and constructions for this purpose as well. In some embodiments, in place of or in addition to sheets of foam or padded textiles, molded contour foam segments can be used to work within the negative space, or contours, of the human body to provide better force distribution. For example, in an embodiment shown in FIG. 3 where the implementation of the architecture of an exemplary soft joint brace 40 is similar to a jock strap, one or more molded foam segments can be positioned under a tailbone pad to provide comfort and protection. As shown in FIG. 3, the brace 40 includes various foam segments positioned on the body, including a girdle tailbone pad 42 and a conformal pad 44 that can be integrated into the girdle. The girdle tailbone pad 42 can include an adjustment mechanism such as a waistbelt tightening ratchet 46 for adjusting the tension on the waistband portion of the brace 40. The pad 44 can be used to fill the negative space when positioned with the girdle tailbone pad 42. The pad 44 is shown in various views in FIG. 3, including a view 48 showing the pad 44 positioned away from the body, and a view 50 showing the pad 44 positioned against the body and having a curvature that conforms to the shape of the body against which it is positioned (a side view and top view of the pad 44 are shown in views 52, 54).

The soft anchor can also be fabricated with variations in elastic modulus and/or thicknesses throughout its profile. A thickness a portion of the anchor can vary to better interface with the geometry of the underlying musculature. The varying thicknesses can be tailored such that the inner surface of anchor can conformably engage the geometry of the underlying musculature, while the outer geometry of the anchor can be presented with a more generalized shape. The anchor can also be designed with thickness variations configured to complement a geometry of the underlying body part for promoting a secure anchor interface. For example, on a typical calf muscle, the wider circumference of the muscle belly compared to the region just below the knee creates an opportunity for the anchor member to mechanically lock around the top of the calf. When presented with an atrophied calf, or other presentation which does not provide this geometry, the anchor can be designed to increase in thickness at the location where a muscle belly is expected.

In some embodiments, the brace can include features for adjustment of the tensile elements and/or adjustment of the compression of the soft anchors. For example, the brace can include one or more length adjusting or pre-tensioning mechanisms (for example, ratchets dials and gears) to adjust the slack length or pre-tension levels of the load bearing components of the brace (for example, tensile elements). They also help to adjust the compression of the soft brace anchors (wraps) to comfortable secure the brace to the body. These include but are not limited to plastic or metallic ratchet dials, gears and pulleys, as well as motors and sensors, which are attached to or embedded in the brace by means of sewing, gluing etc. Thus, the tensile elements can be adjusted manually, using the ratchet dials (for example, formed from plastic or metal), gears, pulleys, or similar devices, or automatically through the use of sensors, color-coded or analog indicators, motors, and/or actuators. These sensors/indicators can be attached or embedded into the brace using a variety of techniques, including but not limited to sewing, gluing, or other attachment mechanisms.

A soft brace joint can also optionally include a hinge, such as a flexible hinge, that allows for motion in one plane while preventing motion in another plane. It will be understood that the flexible hinge can also be referred to as a flexible multi-segment hinge, a flexible multi-part hinge, or a compliant hinge. The flexible hinge can be used alone or in combination with one or more tensile elements and allows for flexion/extension while not restricting motion of the target joint in other planes. In addition, the flexible hinge does not need to be perfectly aligned with the target joint but adds some resistance to at-risk motions to assist in the prevention of injury to the target joint. For example, a hinge can allow knee flexion/extension while preventing knee valgus/varus motion. In some embodiments, the hinge can be formed from various materials and have various geometries that allows for motion in one plane while preventing motion in another plane. In some embodiments, the hinge can be formed from singular or composite materials with continuous/infinite points of rotation. In some embodiments, the hinge can include a plurality of discreet points of rotation, spaced close enough as to mimic continuous points of rotation.

Figure 4:
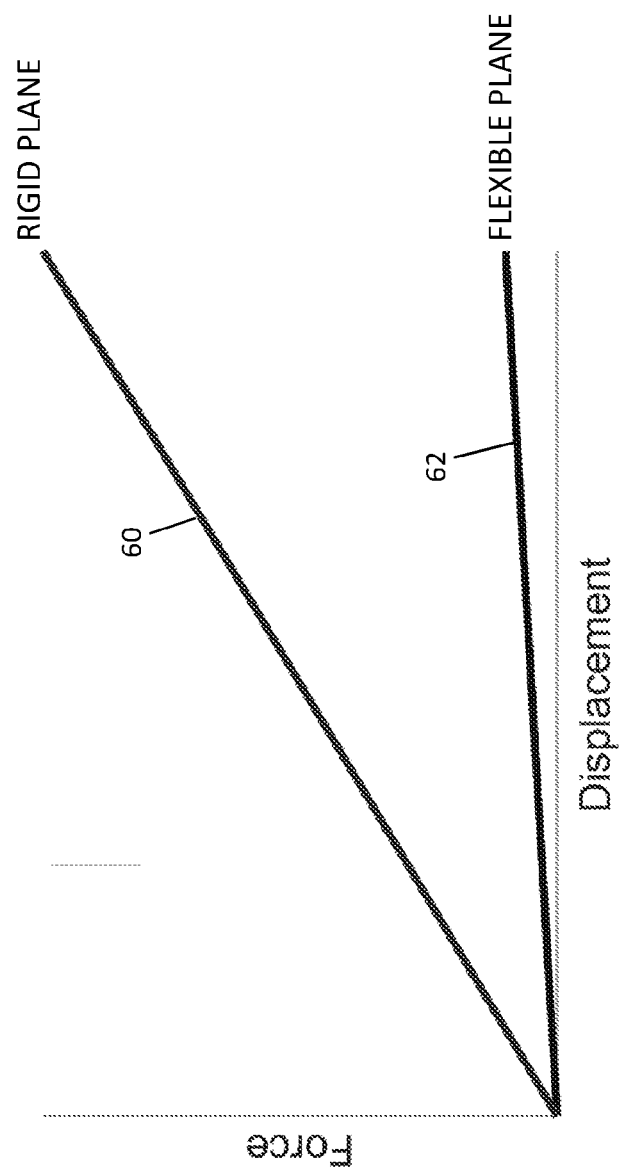
FIG. 4 illustrates an exemplary graph of displacement versus force relating to hinge embodiments.
Figure 5B:
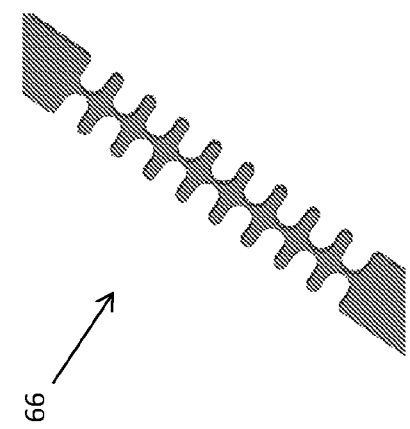
FIG. 5A and FIG. 5B illustrate embodiments of a flexible hinge for use in a soft joint brace.
Figure 5A:
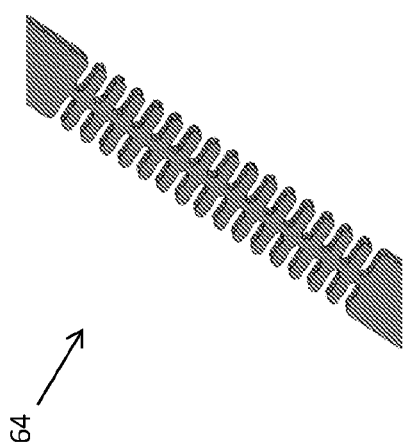

A difference in stiffness in different planes of the hinge allows for free motion in one direction and restricted motion in another, as shown in FIG. 4, which illustrates displacement versus force for a rigid plane (shown by line 60) and a flexible plane (shown by line 62). Stiffness of a hinge can be adjustable through the variation of materials and design parameters. For example, FIG. 5A illustrates an embodiment of a stiffer hinge geometry 64, and FIG. 5B illustrates an embodiment of a more flexible hinge geometry 66. Stiffness can also be adjusted to allow for more or less flexibility in all planes, as shown in FIG. 6, which illustrates displacement versus force for a plurality of stiffnesses for a rigid plane (shown by lines 68, 70) and a flexible plane (shown by lines 72, 74). A hinge can be used in conjunction with any number of the integrated tensile elements/cables, or can be used without any tensile elements, as shown in FIGS. 7A-7B, which illustrates a front view and a side view of a soft joint brace having a plurality of inextensible textiles/soft anchors 82a, 82b, 82c in conjunction with a plurality of hinges 84 for protecting and controlling the motion of a knee joint. It will be understood that any number of anchors can be used in conjunction with any number of hinges depending on the needs of the targeted joint.

A soft joint brace can provide protection to a joint by performing a variety of functions depending on the configuration of the components of the brace. In some embodiments, the brace can replicate the non-linear behaviour of biological tendons or ligaments using a combination of the soft anchors (wraps) and load bearing elements (for example, tensile elements). This approach is capable of achieving complex non-linear properties, similar to those of biologic soft tissues. This bracing approach can be used to augment the biomechanical function of joint soft tissues (i.e. ligaments) to control joint motion. By protecting the joint against excessive motion, the brace can help to lower the risk of injury. In some embodiments, an exemplary knee brace can include tensile elements (external ligaments) that can be configured to replicate the ACL loading under knee abduction rotation. The external ligament can utilize body lengthening during certain movements to provide increased tension in an external cable. In some embodiments, if a knee injury accrued with a flexed hip joint, an external ligament of the brace can provide additional tension along the knee when the hip joint is flexed.

Figures 8, 9:
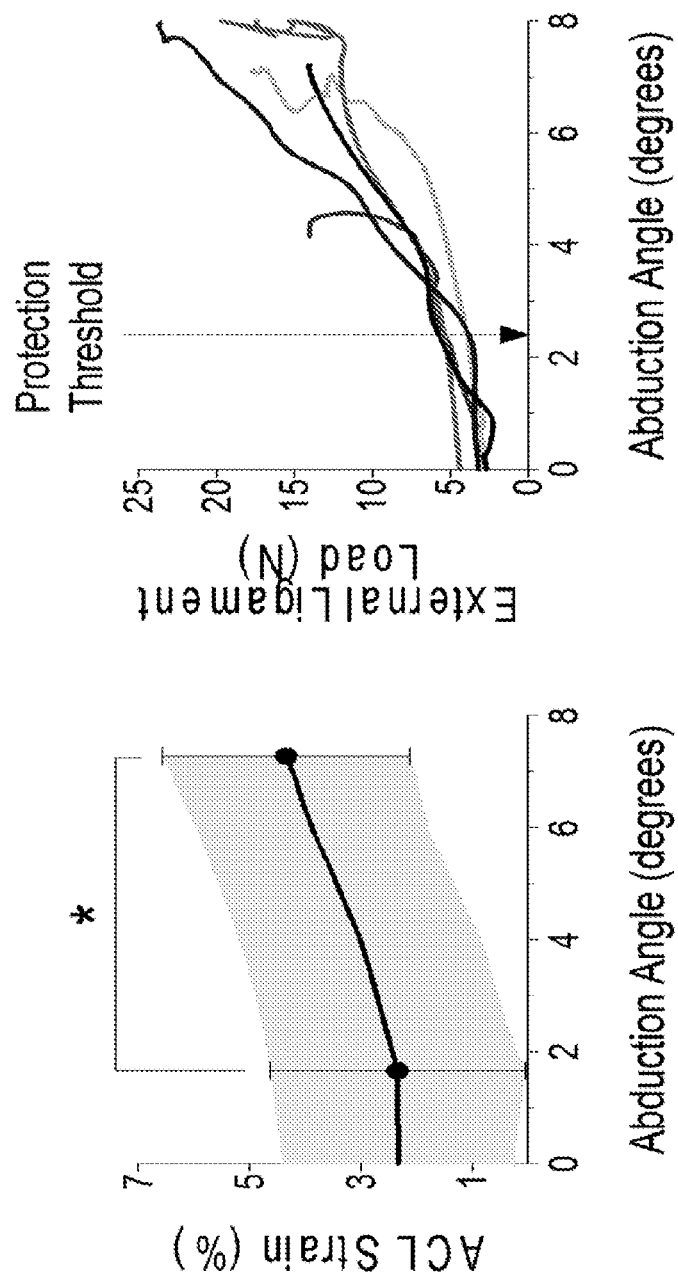
FIG. 8 illustrates an exemplary graph of changes in ACL tension.
FIG. 9 illustrates an exemplary graph showing changes in tensile element (external ligament) tension.

FIG. 8 illustrates an exemplary graph showing non-linear changes in ACL tension in response to increased knee abduction in human cadaveric knees. FIG. 9 illustrates an exemplary graph showing non-linear changes in external ligament tension in response to increased knee abduction in 5 healthy subjects.

In some embodiments, a brace can provide targeted protection to the joint using one or more tensile elements embedded in the brace in a variety of pre-determined configurations (for example, varying the number, length, angle, position, slack or pre-tension of one or more tensile elements) to further stabilize the joint and or resist joint motion in a specific direction without affecting other joint motions. For example, a brace for a knee joint can include a tensile element which resists knee abduction and internal rotation (as primary contributors to ACL loading in injury risk) without affecting knee flexion. The configuration of the tensile elements can be changed based on the type of the joint and injury (joint structure which requires protection). Depending on the application, multiple tensile elements can be used to resist different motions in the joint.

In some embodiments, a brace can protect a joint under high-risk motions/movements without affecting joint motion (function) during normal (low-risk) conditions. The tensile element(s) can be configured to remain unengaged (unloaded or loose) during normal joint range of motion but will become engaged (loaded or tensioned) after joint moved in beyond a pre-specified range of motion or above a pre-specified speed. Thus, it only resists joint motion during high-risk conditions without interfering with normal joint function.

In some embodiments, a brace can provide a customizable (adjustable) protection level to meet the preference and needs of a wearer (e.g. joint laxity, injury risk profile, type of activities). By adjusting the pre-tension (or slack length) of one or more tensile elements, the protection level (e.g. the motion (angle, speed) threshold beyond which the tensile element engages and starts to resist joint motion) can be adjusted.

In some embodiments, a brace can use a combination of loadbearing components (for example, tensile elements) and multiple soft conformable anchors (wraps) to distribute the forces across a large area of the body. In some embodiments, a brace can use multiple soft conformable anchors (wraps) and embedded loadbearing components (for example, tensile elements) to the brace to the body and minimized the brace drift without sacrificing comfort and interfering with muscle function. In some embodiments, one or more user replaceable flexible hinges can be used to provide tunable stiffness as needed for performance and needs of the wearer. For low injury risk individuals or activities, high flexible hinges can be omitted from the device. For high risk individuals or activities, an appropriate hinge can be added in parallel to the external ligament (tension element) to provide additional protection.

In some embodiments, a soft joint brace can include modular instrumentation features, such as various sensors and electronics, in order to provide measurements of patient-oriented, functional, biomechanical and/or neuromuscular ranges of outcomes. In some embodiments, a brace can include a wearer compliance sensor to monitor how often and for how long the brace has been used. In some embodiments, a brace can include one or more sensors to monitor the tension in one or more tensile elements to know how it is pretensioned and what forces are applied. In some embodiments, a brace can include a joint activity monitoring sensor (i.e. range of motion, velocity, potential impact, alignment, force applied to joint etc.) that can estimate injury risk and provides real time-feedback to the athletes/patients to inform them if they are loading their joint in a proper way. In some embodiments, a brace can include neuromuscular activity control that tracks neuromuscular performance (i.e. muscle contraction patterns). Additional probes and/or sensors can be added to the brace in order to improve the joint proprioception and muscle coordination through vibration or selective on-demand excitation of muscles. In some embodiments, the combination of sensors, motors, and/or actuators allows the brace to automatically adjust and/or customize the tension in the one or more tensile elements to control various types of motion of the joint. This combination of elements can also be used to provide and/or maintain a predefined resistance against motion. For example, in some embodiments, active adjustment of the tension in the tensile elements can be gradual over time to maintain a certain pretension to account for drift of the anchors of the brace.

Figure 10:
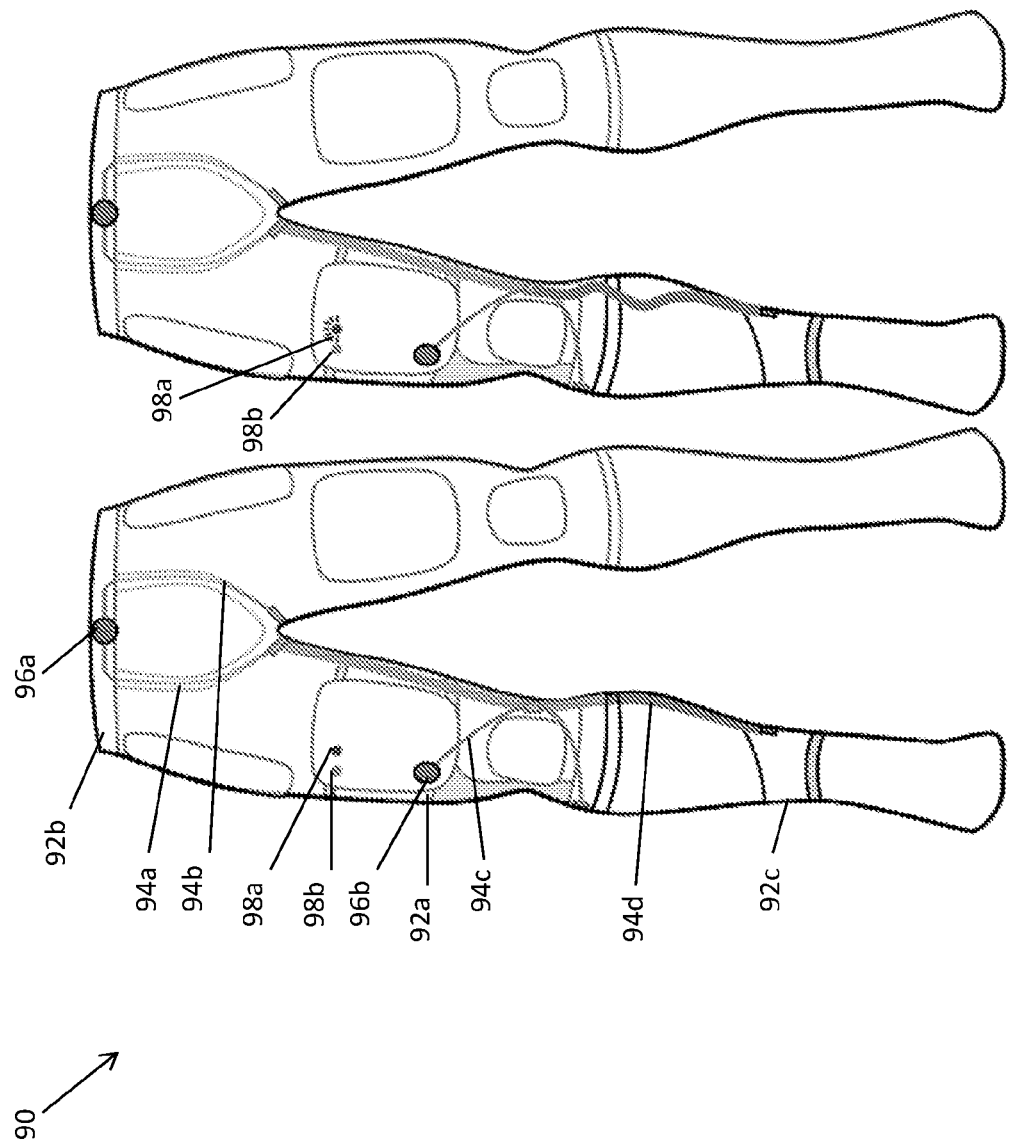
FIG. 10 illustrate embodiments of a soft joint brace having one or more sensors or indicators associated therewith.

In some embodiments, a brace can include one or more sensors/indicators to monitor the tension in one or more tensile elements to know how the tensile element is pretensioned and what forces are applied. In some embodiments shown in FIG. 10, one or more color-coded LEDs and/or analog indicators (for example, dials or cables) can be used to give feedback to the user regarding the tension level present in an external cable. This information can be used to determine when to tighten the tensile element. As shown in FIG. 10, a soft joint brace 90 can include inextensible textiles including a thigh anchor 92a, a waist anchor 92b, and an ankle anchor 92c. Channels can be formed through which anchor support cables 94a, 94b can run. An adjustable dial 96a can be used to adjust the tension in the cables 94a, 94b, and cable guides can be used to assist with the placement of the cables 94a, 94b. A cable 94c is positioned to run through the target joint (the knee, in FIG. 10) and is coupled to an adjustable dial 96b for adjusting the tension thereof. The brace 90 can also include an anchor support cable 94d that run between the cable guides and the thigh and ankle anchors 92a, 92c. The brace 90 includes indicators 98a, 98b that provide feedback regarding the tension in one or more of the cables of the brace 90. As shown in FIG. 10, the indicator 98b can become illuminated to indicate any type of feedback to the user of the brace 90. It will be understood that any type of indicator or sensor can be used to provide feedback, including LEDs, audible feedback, or another other mechanism.

For example, the soft joint brace can include various other sensors, electronics and/or actuators including but not limited to a pressure or force sensor for monitoring or controlling the interaction pressures/forces with the wearer, the sensors for monitoring the temperature, perspiration or other physiological measures of the wearer, and/or an optical or acoustic sensors that could be embedded to noninvasively measure changes in underlying tissue characteristics or blood flow either outside or inside the body. It will be understood that any type of sensor can be added to the soft joint brace to monitor the body of the wearer.

In some embodiments, a soft joint brace can provide adjustable protection levels. A combination of a soft structure with a length adjustability element (for example, ratchet dials and gears) can result in inherent variability of threshold between free motion and resistive mode of the brace. The length adjusting mechanisms can be done manually (for example, using ratchet dials) or automatically using, for example, motors. Additional sensors can be incorporated into the system to continuously measure the length and pretension levels of each tensile element. Those measurements can be used to provide a real-time feedback on the brace protection levels, and to readjust/realign the tensile elements, or any other brace components, manually or automatically using actuators. Additional sensors and/or indicators can be incorporated into the device to measure the length and pretension of each tensile element. In some embodiments, the measurements can be taken continuously, or the measurements can be taken at specified time intervals. The sensors and/or indicators can include but are not limited to LED indicators and color-coded or analog dials and cables.

Figure 11A:
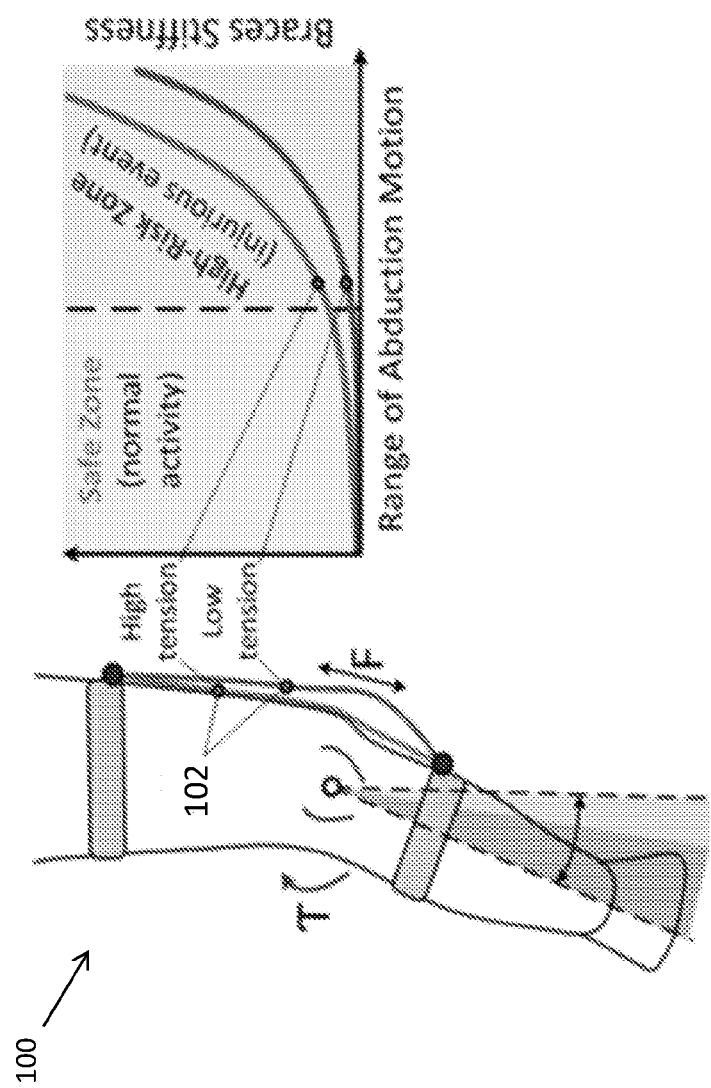
FIG. 11A and FIG. 11B illustrate an embodiment of a soft joint brace for use with a knee joint.
Figure 11B:
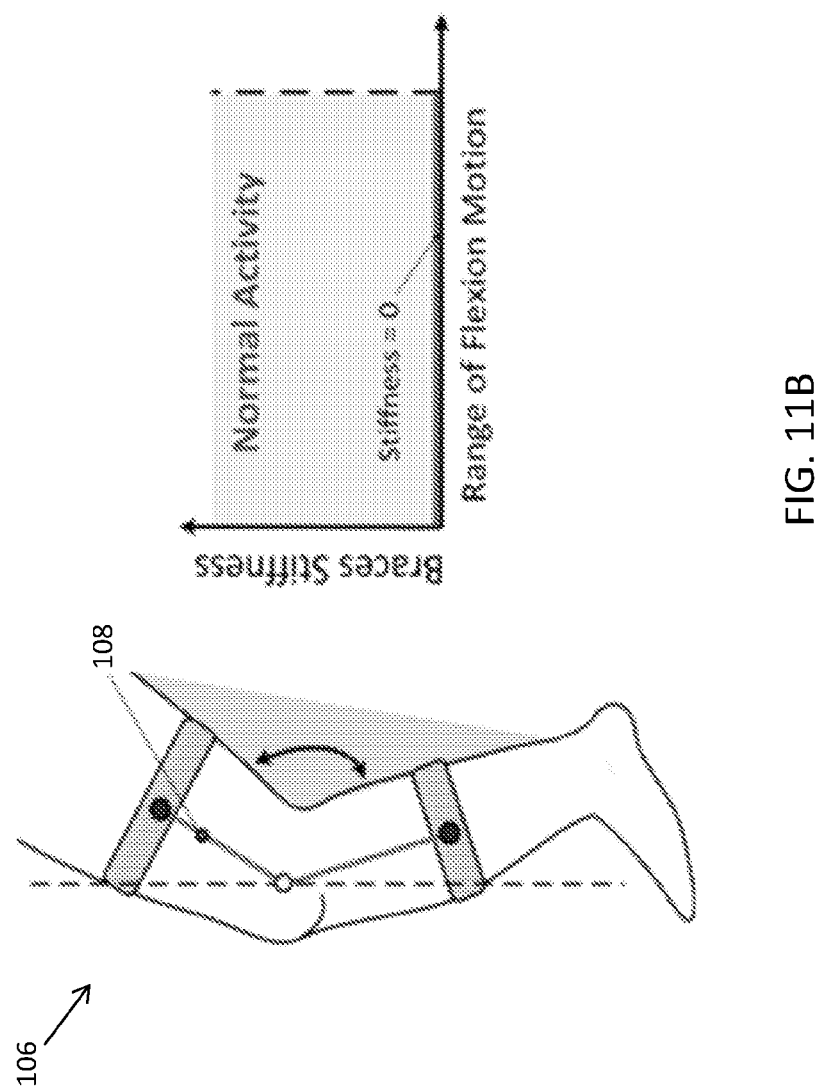

A soft joint brace as described herein can be used with a single body joint, various body joints, or a body segment. For example, a soft joint brace can be used for protection of a knee. To provide protection, one or more tensile elements can span the joint in specific positions and orientations to protect the knee against excessive rotations in some directions without affecting knee motion in other directions. These tensile elements (also referred to as a "protective cable" or "cable" or "external ligament" or "protective fiber") are triggered by excessive rotation after a certain threshold, and then dissipate resistive forces among anchor points on the body. FIGS. 11A-11B illustrate an embodiment of a soft joint brace 100 for use with a knee that includes adjustable levels of protection for the joint. For example, to prevent excessive amplitude of knee abduction motion during landing, a protective cable 102 can be anchored to the points on the thigh and calf of the wearer as shown in FIG. 11A. Assuming that anchor points are rigidly fixed to the body, stiffness of the brace 100 can depend on the stiffness of the protective cable and its slack length. By adjusting the pre-tension levels, or slack length, of the cable, the threshold can be adjusted after which the protective cable will engage and resist knee rotation. This enables adjustment of the brace protection level based on multiple factors including but not limited to personal preference, injury risk profile, type of athletic activity, and sport requirements.

During knee protection, it is important to not disturb normal patterns of the knee flexion. Therefore, the protective cable can be positioned such that it does not provide any tension during knee flexion. In some embodiments, this can be achieved by guiding one or more protective cables 108 of a brace 106 through the approximate center of rotation of the knee, as shown in FIG. 11B, which kinetically ensures the same cable tension throughout full range of flexion. In the exemplary embodiment shown in FIG. 11B, there is no tension on the cable 108. The cable-guiding system can be anchored to the calf of the wearer. The calf is a more stable area compared to the thigh in terms of change of muscle volume during sport activities. This proposed structure has significant advantages, since multiple tensile elements can be engaged to protect multiple motions per joint.

Figure 12:
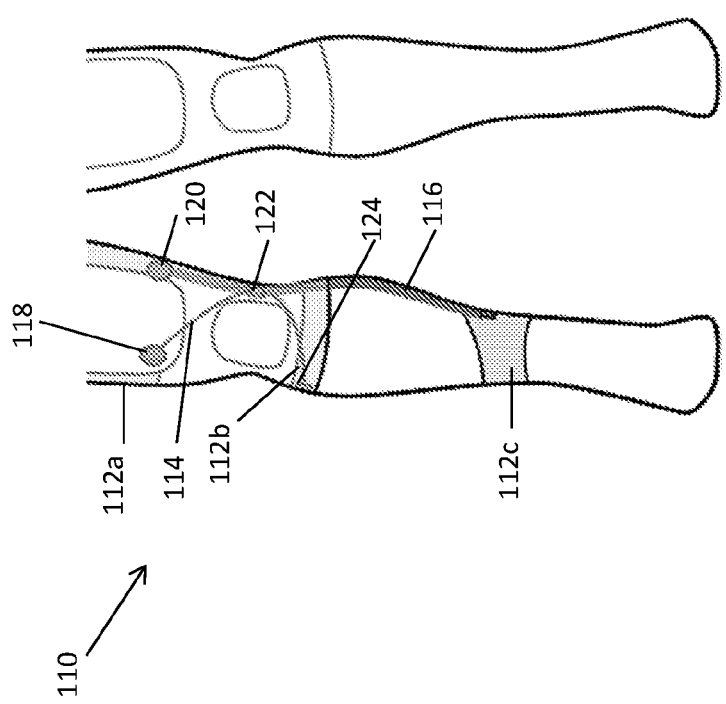
FIG. 12 illustrates an embodiment of a soft joint brace having external cables and support cables.

In some embodiments, an external cable can be guided through an approximate center of rotation of the knee. For example, an additional anchor support cable 114 can be used as part of a brace 110, as shown in FIG. 12, and the cable 114 can restrict an external ligament cable 166 from deviating away from the approximate center of rotation of the knee. The anchor support cable 114 can be integrated into an inextensible textile of the brace 110. As shown in FIG. 12, the soft joint brace 110 can also include inextensible textiles 112a, 112b, 112c. Adjustment mechanisms, such as adjustable dials 118, 120 can be used to adjust the tension in the cables 114, 116, and a cable guide 122 can be used to assist with the placement of the cables 114, 116.

Figure 13:
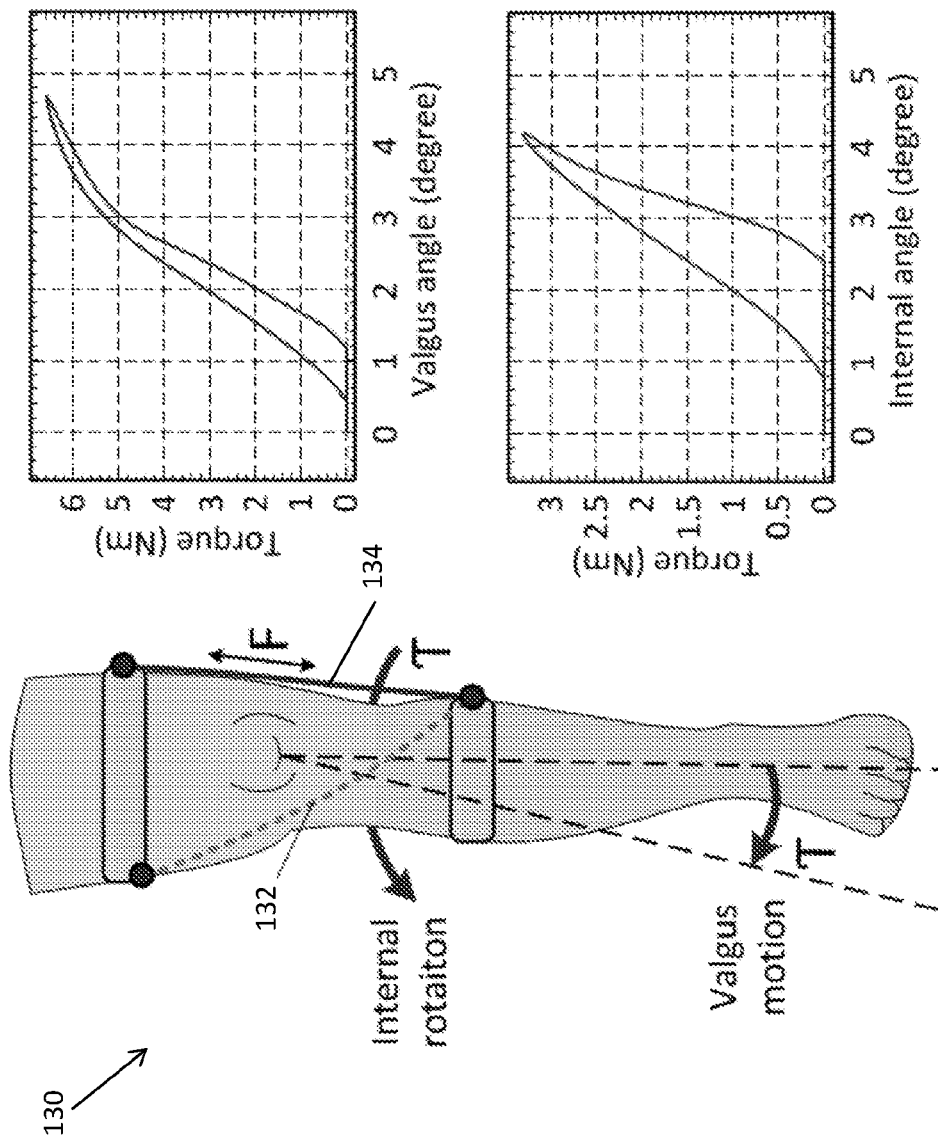
FIG. 13 illustrates an embodiment of a soft joint brace for use with a knee joint.

With soft knee bracing, it can define which degree of freedom to affect. Multiple degrees of freedom can be affected simultaneously by spanning more than one cable around the joint. For example, additional protective cables, such as a cable 132, can be applied around the knee joint to prevent internal rotation motion and provide multi-planar joint protection, as shown in FIG. 13, which illustrates a soft joint brace 130 having a protective cable in the form of an external ligament cable 134 and protective cable 132.

The routing of the cables can determine a direction of resistive force vector that will eventually transform into resistive moment in certain motion planes. For example, two protective cables can be fixed to the same anchor points on the body to restrict knee abduction (valgus) and internal rotation motions (as shown in FIG. 13). Exemplary results are shown in the figure graphs below. Both motions generated sufficient amounts of resistance.

Figures 14A, 14B, 14C:
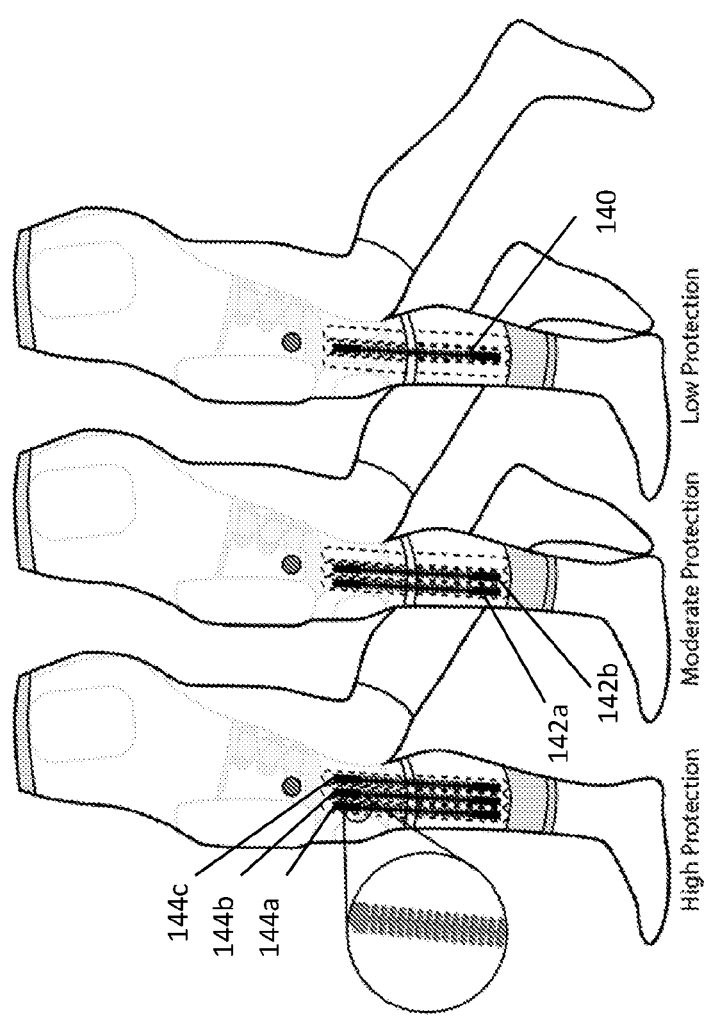
FIGS. 14A, 14B, and 14C illustrate embodiments of soft joint braces with various flexible hinge configurations.

Additionally, an effect from a single protective cable on two motions planes can be seen. This platform can be used to protect different joints (for example, knee, shoulder, hip, and ankle) and many degrees of freedom. Hinge size and orientation can be adjusted to provide appropriate levels of protection to different joints. For example, as shown in FIGS. 14A, 14B, and 14C, the number of hinges can also be adjusted to provide different levels of protection to a joint. As shown in FIGS. 14A, 14B, and 14C, increasing the number of hinges used to span a target joint can increase the amount of protection provided to the target joint by the one or more hinges (for example, a single hinge 140 shown in FIG. 14C provides less protection than a brace with first and second hinges 142a, 142b, shown in FIG. 14B, which in turn provides less protection that a brace with first, second, and third hinges 144a, 144b, 144c as shown in FIG. 14A).

Figure 15:
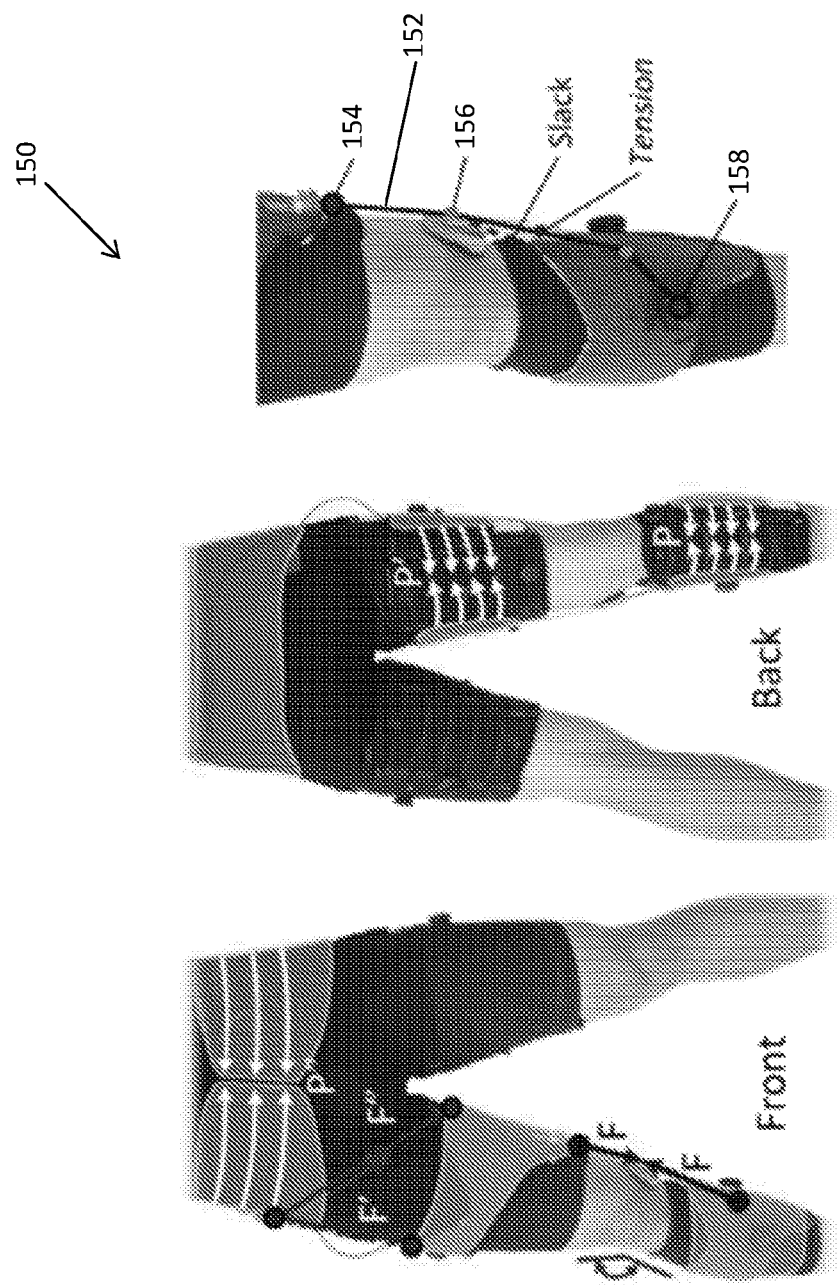
FIG. 15 illustrates front, back, and side views of a knee soft joint brace.

In some embodiments using a soft bracing technique, anchoring inextensible protective cables to the body securely is provided. Anatomical anchors, like the thigh and calf, have soft tissues (i.e. muscle, fat and skin) that easily deform, posing challenges for proper anchoring. In some embodiments, forces are distributed between components that anchor not only to dynamic areas like thighs and calves, but also to geometrically stable areas like hip bones, as shown in FIG. 15, which illustrates an exemplary embodiment of a brace 150 that utilizes force distribution and stable anchoring of the protective cables, such as a protective cable 152. The brace 150 can include, for example, an anchor point 154, cable guide 156, and an adjustment mechanism, such as a knob 158. Forces applied to the protective cables dissipate into multiple components that use compression, friction, and geometrical stability to stay in place on the body. High friction material can be applied to the internal component surfaces that interact with skin to reduce slippage on the body. A ratchet dial-activated compression system can be used to apply customizable compression on soft tissues resulting in more stable and rigid area. Finally, semi-rigid non-textile components (also referred to as "semi-rigid plate" or "flexible plate" or "semi-rigid flexible plate") can be incorporated into components to increase tensile stiffness of the garment and provide stable anchoring points for protective cables, while allowing muscles to naturally expand during activation.

Braces can play a significant role in athletic performance, not only by protecting joints, but also by reducing speed, adding uncomfortable weight, and causing painful chafing. Therefore, it is important to emphasize user-focused design of the soft brace. Each component must be comfortably located on the body, distributing forces and overall brace weight over large parts of the body. As previously described, in the exemplary knee brace, weight and other forces can be distributed among one or more anchors, such as the three components anchored to the hip bones (an anchor 162), thigh (an anchor 164) and calf (an anchor 166), as shown in FIGS. 16A-16B, which illustrate a front view (FIG. 16A) and a back view (FIG. 16B) of a soft joint brace 160 on a body. The brace also includes various semi-rigid plates 168, textile portions 170, and one or more protective cables 172 that extend across planes of the body. The brace 160 can also include various mechanisms to adjust the brace 160, such as adjustment mechanisms to adjust the tension of the cables 172, and compression mechanism 174 that allow for adjustment of the compression of the textile portions 170 on the body. To avoid added metabolic costs, additional weight of the system should be as close to the center of mass as possible. Soft bracing techniques shift some of the weight to the center of trunk, improving usability and comfort. The use of soft functional materials makes the brace more transparent and comfortable compared to rigid braces made of metal hinges and anchors and hard plastic parts. The dynamic protection level (i.e. no protection during normal range of motion and increased protection after excessive motion) and targeted protection (i.e. resisting a certain knee motion without affecting other degrees of freedom) help improve brace comfort and reduce brace-induced fatigue otherwise caused by rigid braces. The soft brace technique can provide a reduction of motion for multiple degrees of freedom of the joint at the same time without disrupting normal gait.

Figure 18:
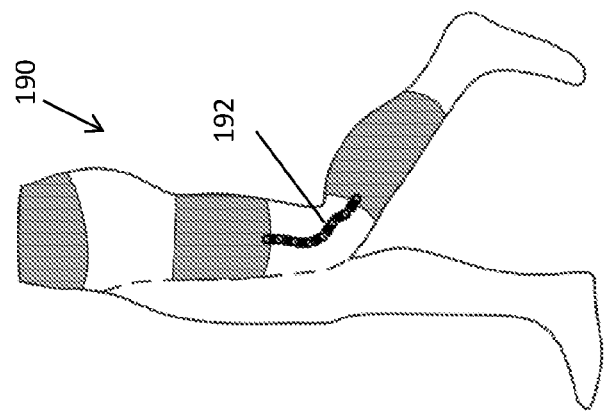
FIG. 18 illustrates a side view of an embodiment of a knee soft joint brace having a chain-like external ligament.
Figure 17B:
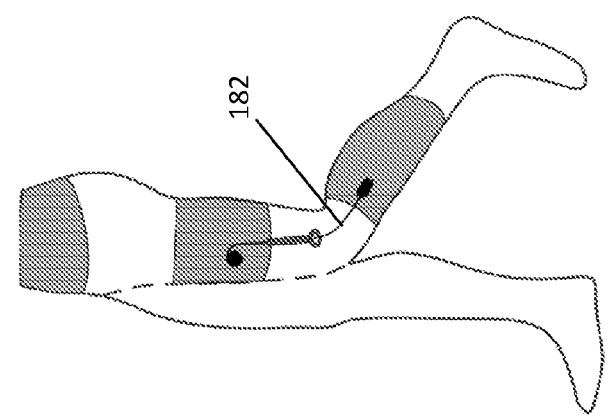
FIG. 17A and FIG. 17B illustrates side views of embodiments of a knee soft joint brace having different embodiments of a guiding system for a tensile element.
Figure 17A:
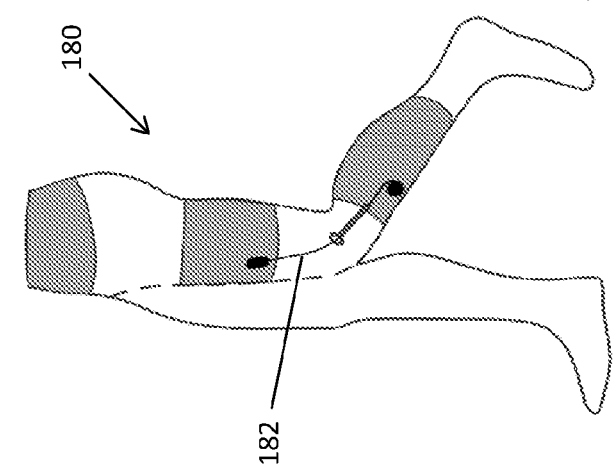
Figure 19:
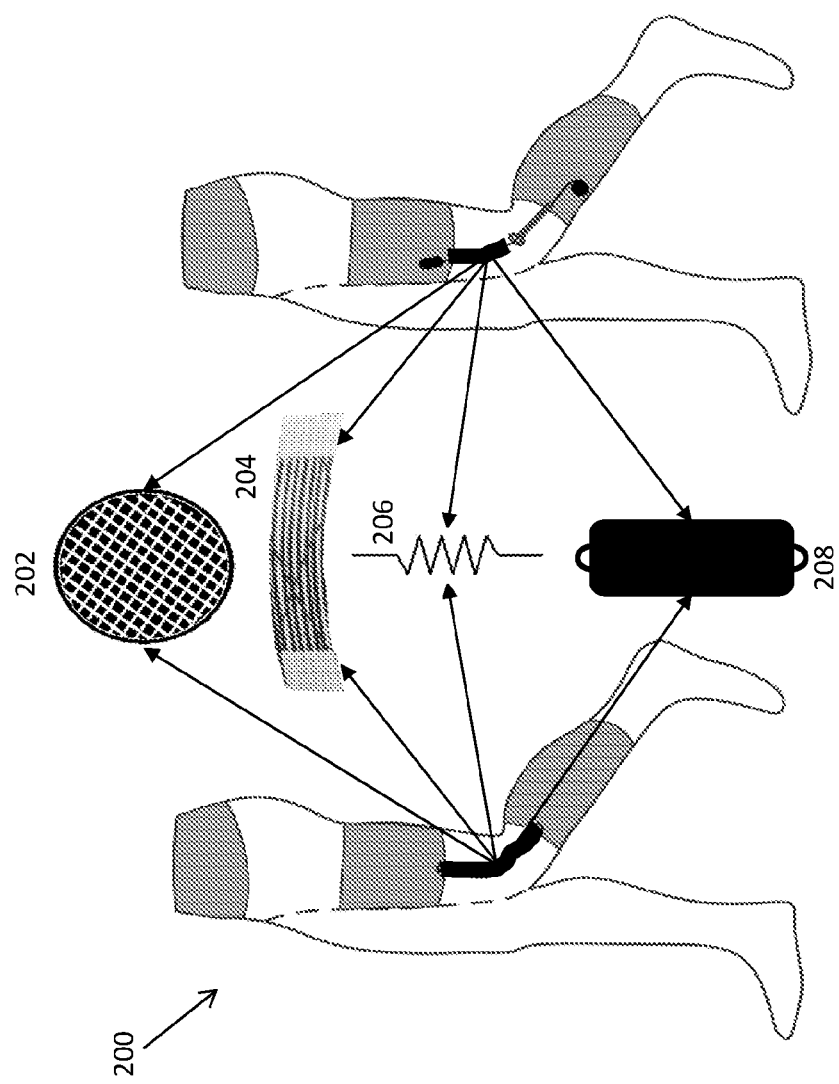
FIG. 19 illustrates a side view of an embodiment of a knee soft joint brace having an external ligament with a composite structure.

Various mechanisms can be used to form the tensile elements used for external ligaments in a soft brace. In some embodiments, a soft knee brace 180 as shown in FIGS. 17A-17B can include one or more high-strength cables or ropes 182 for the external ligament module. In some embodiments, a soft knee brace 190 as shown in FIG. 18 can include a chain type mechanism 192 with links for the external ligament module that can bend freely in one plane but restricts motion in other plans. In some embodiments, a soft knee brace 200 as shown in FIG. 19 can use a composite structure 202, ribbons 204, springs 206, or fluid (e.g. shear thinning, magnetorheological fluids) cylinders 208 alone (left) or combined with cables, ropes or chains (right) for the external ligament module.

Figures 20A, 20B, 20C:
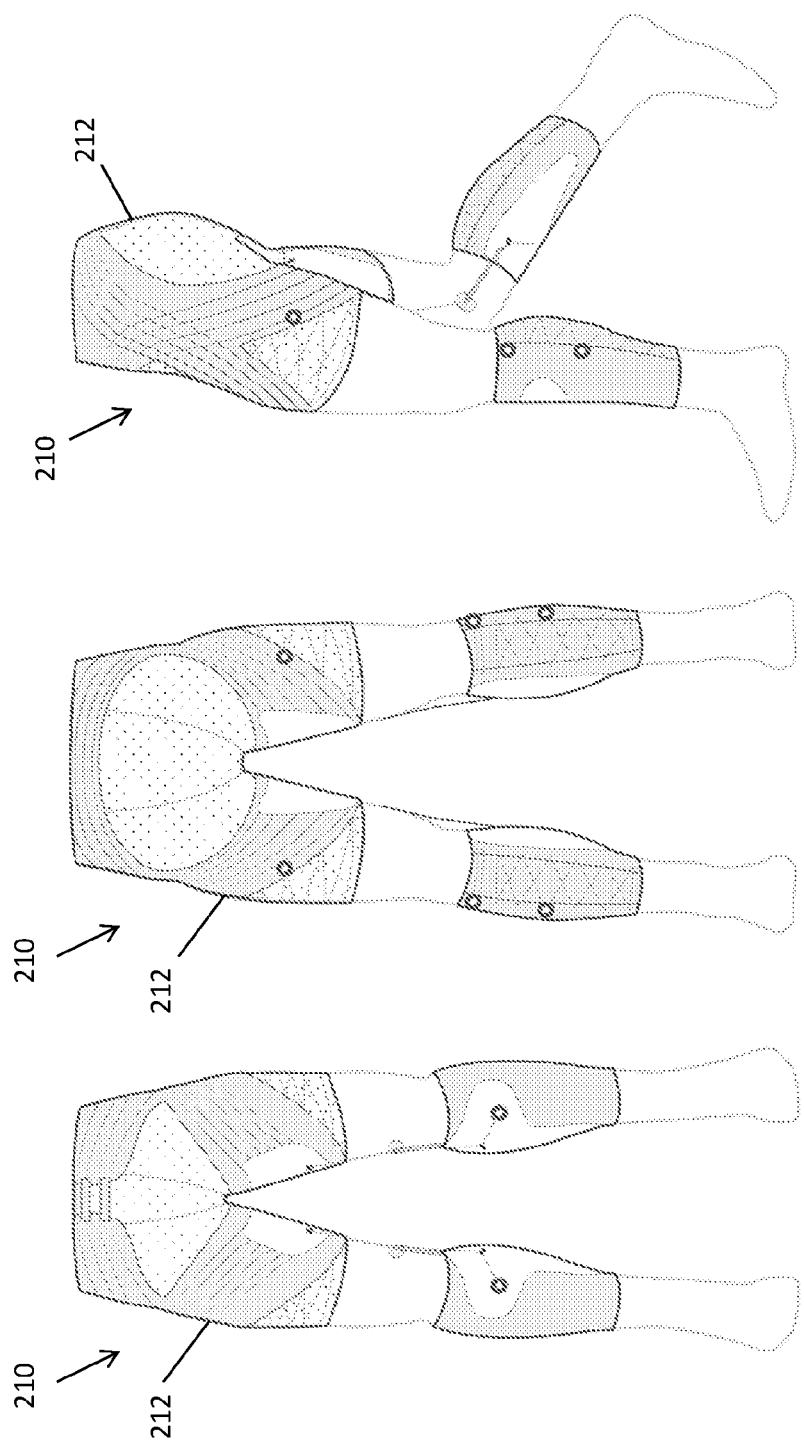
FIGS. 20A, 20B, and 20C illustrate a front, back, and side view of an embodiment of a knee soft joint brace with a hip and/or thigh anchors.

In some embodiments, a soft knee brace 210 can include integration of hip and/or thigh anchors into one component, such as an anchor 211 so it can be put on more easily and worn as one garment, as shown in front, back, and side views of the brace 210 illustrated in FIGS. 20A, 20B and 20C. It can be understood that the hip and/or thigh anchors can also be separate from the other components of the brace.

Figure 21:
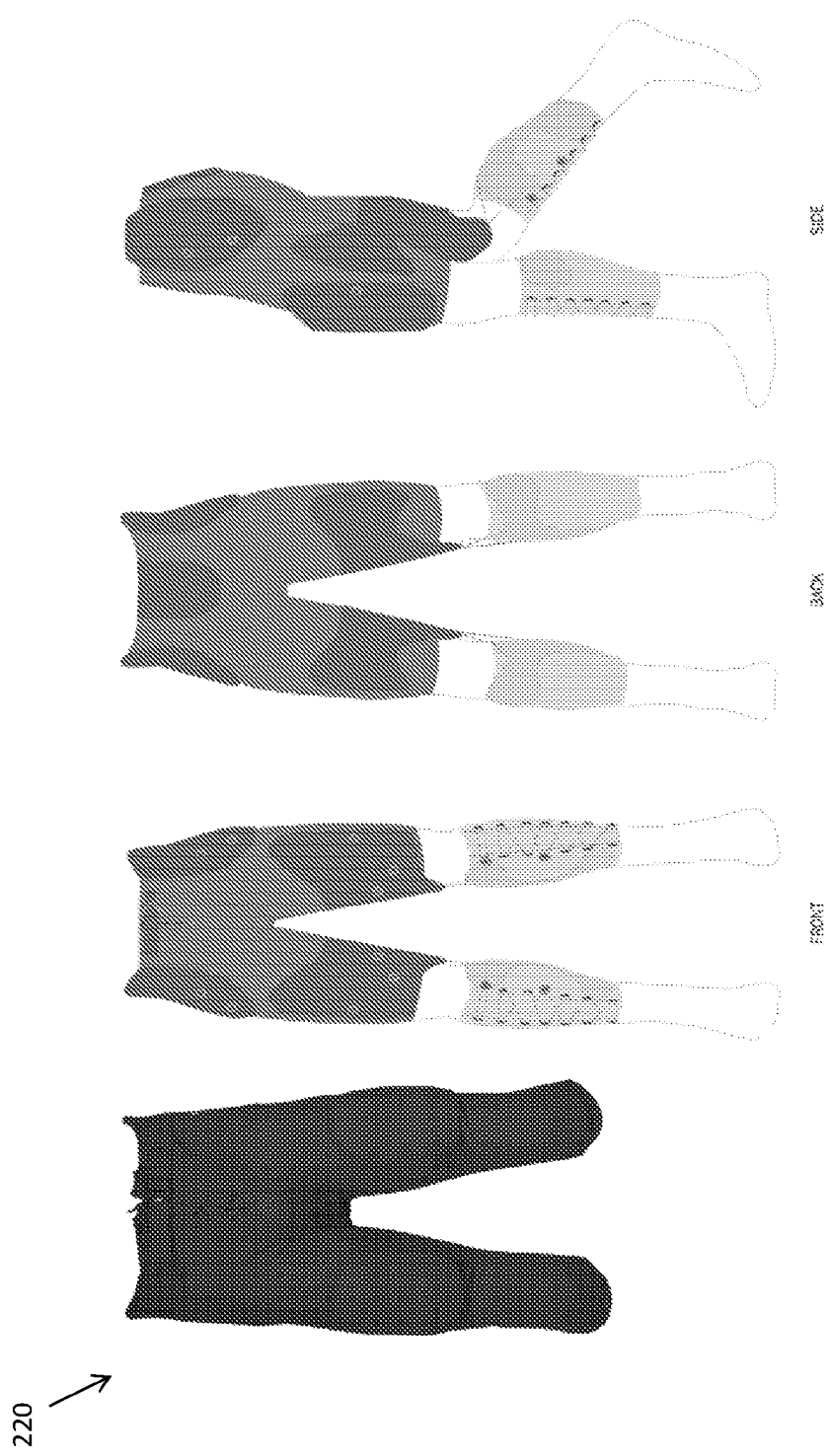
FIG. 21 illustrates various view of an embodiment of a knee soft joint brace integrated into a garment.

In some embodiments, a soft knee brace can be integrated into athletic garments 220 (for example, football gear), as shown in FIG. 21. It will be understood that a brace for any joint of the body can be integrated into various types of garments, including but not limited to socks, shirts (for example, in the sleeves), and pants.

Figures 22A, 22B:
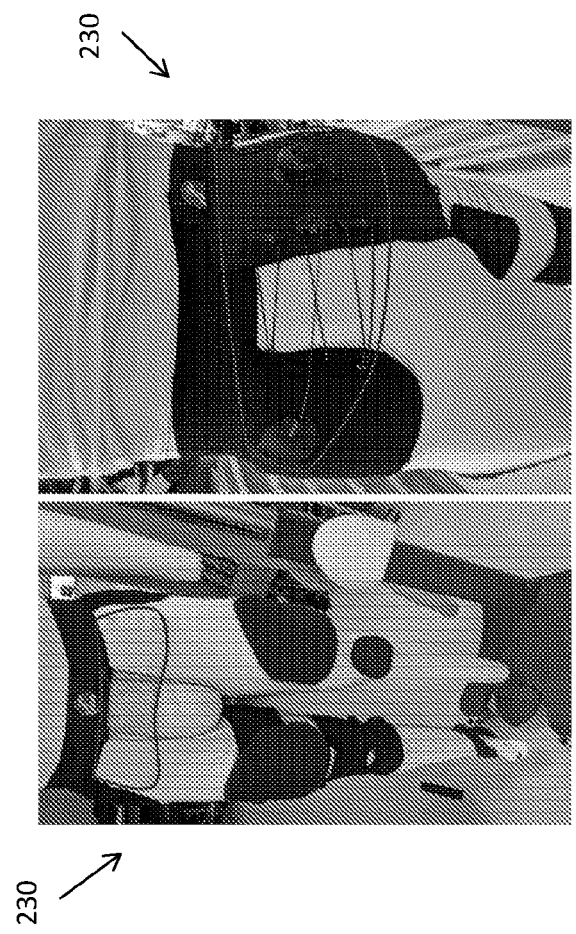
FIG. 22 illustrates an embodiment of a body anchoring component integrated within a garment for adherence to anatomical features, force distribution, and ease of donning.

In some embodiments, one or more braces can be integrated into a garment, such as a football girdle 230, as shown in FIG. 22A and FIG. 22B. A textile suit can be combined with semi-rigid padding elements for ease of donning and adjustability. As shown in FIG. 22B, a waistbelt can be hidden inside the waist of the girdle, which can include a tightening system as shown in FIG. 22A.

Figures 23A, 23B:
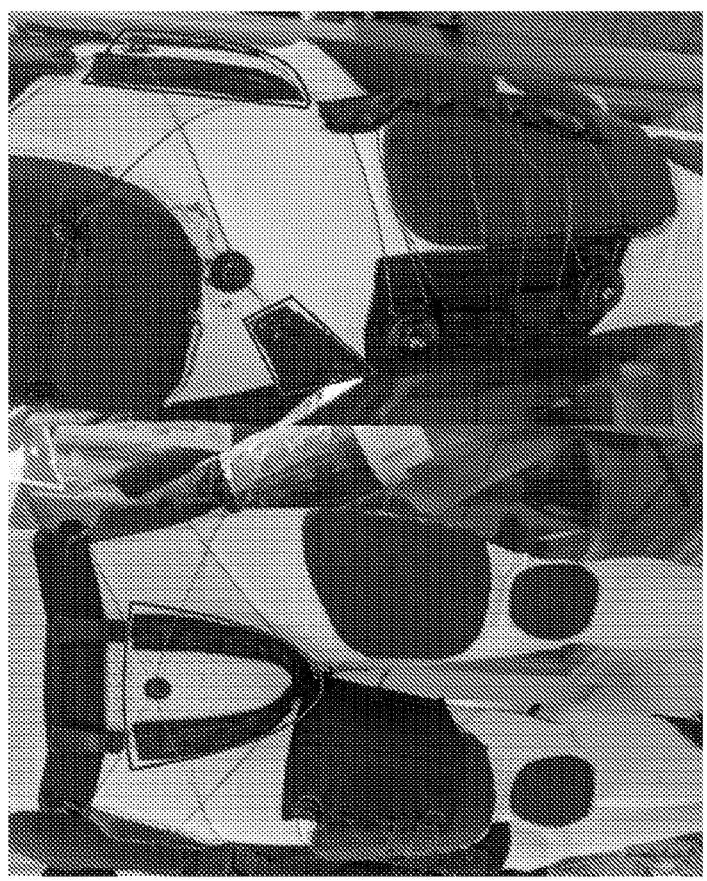
FIG. 23A and FIG. 23B illustrate an embodiment of inextensible, padded force paths integrated into a garment for providing a means of routing inextensible materials to anatomical features in a comfortable manner.

Stiff and padded tunnels can be routed internally and/or externally throughout stretch garments and accessories as force paths. For example, a multi-layered system of nylon, foam, and plastic guides can be external to a garment 240 (as shown in FIG. 23A and FIG. 23B) for ease of construction or can be placed inside the garment for a simpler look. The force paths distribute forces around the body and can provide localized pressure distribution to improve comfort and allow the user to increase anchoring tension.

Figure 24:
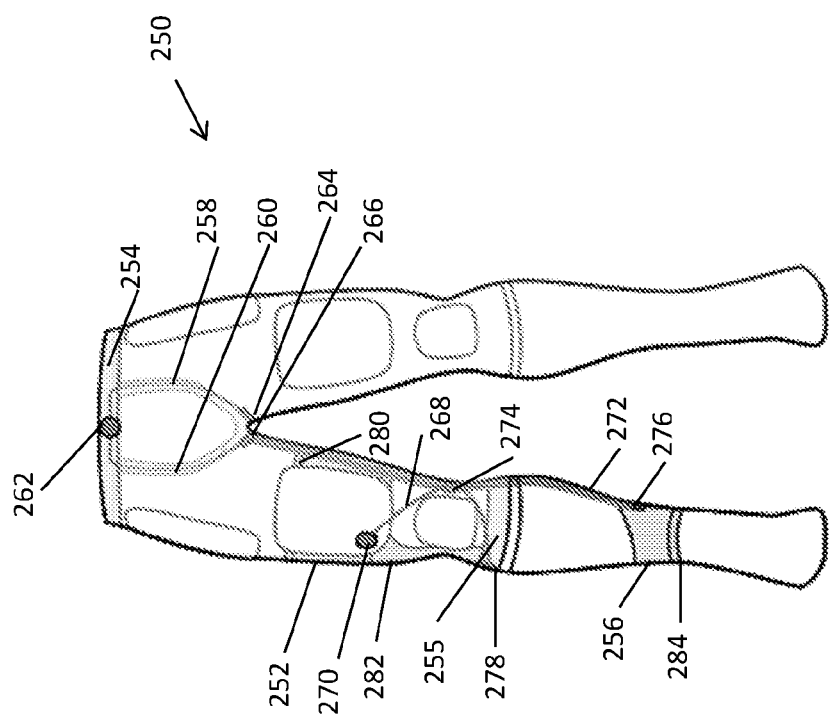
FIG. 24 illustrates a front view of an embodiment of a soft joint brace integrated into a garment.

High friction insets can also be incorporated into the design of a garment under suit components to prevent drift during use. It will be understood that the high friction inset can also be referred to as a high friction component, a high friction element, a compression plane, a plane of compression, or a compression element. Drift can hinder the efficacy of external cables to remain in tension during movement. Preventing drift can improve performance of a brace. As shown in FIG. 24, high friction insets can be used to prevent a thigh brace and a calf brace from moving towards one another, which can prevent the external cable's knee alignment guide from shifting circumferentially around the knee during movement. As shown in FIG. 24, a soft joint brace 250 can include inextensible textiles including a thigh anchor 252, a waist anchor 254, a calf anchor 255, and an ankle anchor 256. Channels can be formed through which anchor support cables 258, 260 can run. An adjustment mechanism, such as an adjustable dial 262, can be used to adjust the tension in the cables 258, 260, and cable guides 264, 266 can be used to assist with the placement of the cables 258, 260. A cable 268 is positioned to run through the target joint (the knee, in FIG. 24) and is coupled to an adjustment mechanism, such as an adjustable dial 270, for adjusting the tension thereof. The cable 268 can be positioned using cable guides 274, 278. The brace 250 can also include an anchor support cable 272 acting as an external ligament that run between the cable guide 266 and additional cable guides 274, 276 located near the thigh and ankle anchors 252, 256. High friction textiles 280, 282, 284 can be positioned at the thigh, target joint, and ankle to prevent drift of the brace 250 related to the body. It will be understood that any number of high friction components can be positioned at any location on the body as long as their number and positioned are capable of preventing drift of a soft joint brace or a garment with which a soft joint brace is associated.

As noted above, a soft joint brace can be used to protect various joints throughout the body. It will also be understood that any of the features described above relating to a soft joint brace for use with a knee can be applied to any soft joint brace that is used with any part of the body or body segment. In addition, it will be understood that the components that form a soft joint brace can be used in any number and configuration depending on the type of motion protection that the brace is being used for.

In some embodiments, a soft joint brace can be used to protect an ankle. Ankle sprains are very common injuries, in particular among active individuals including athletes and military personnel as well as factory workers. Some 25,000 people do it every day. A sprained ankle means one or more ligaments on the outer side of your ankle were stretched or torn. Typically the ankle is rolled either inward (inversion sprain), or outward (eversion sprain). Inversion sprains cause pain along the outer side of the ankle and are the most common type. Pain along the inner side of the ankle may represent a more serious injury to the tendons or to the ligaments that support the arch.

Figures 25A, 25B:
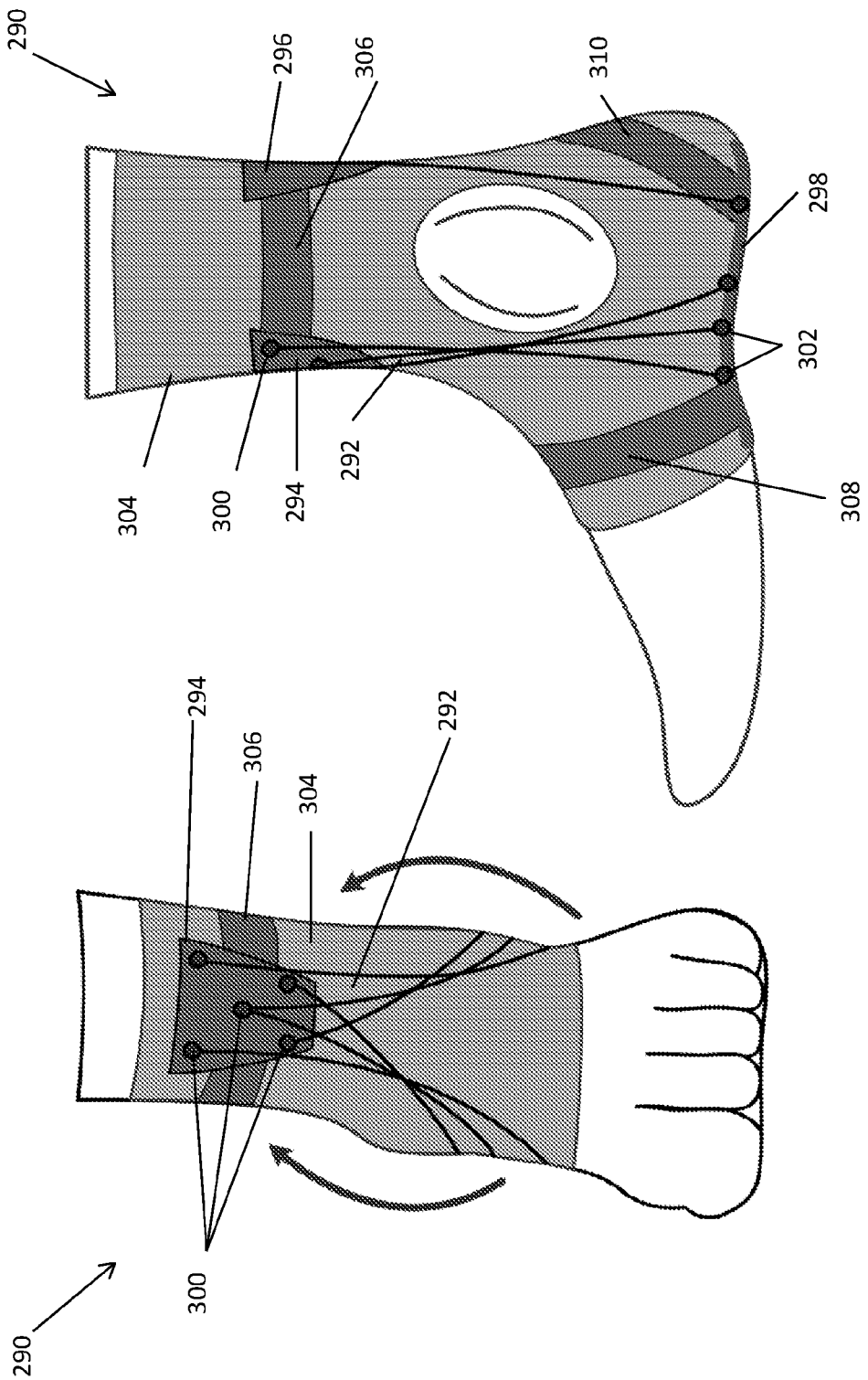
FIG. 25A and FIG. 25B illustrate front and side views of an exemplary embodiment of a soft joint brace for protecting an ankle joint.

In some embodiments, the purpose of the brace for use with the ankle is to prevent possible tear or sprain of lateral and/or medial and internal ankle ligaments. In some embodiments, a brace can be divided in two separate braces (for one side only) by removing some of the external cables. In an exemplary ankle brace 290 as shown in FIG. 25A and FIG. 25B, a plurality of external ligaments 292 can run around the medial and lateral aspects of the ankle joint to prevent excessive ankle pronation and supination and/or inversion and eversion to lower the risk of ankle injuries. In some embodiment, the external ligaments can be routed inside the brace using a guiding system, such as channels (tubes), embedded in the soft brace to keep the external ligaments in proper orientation to protect the joint in a targeted manner. In some embodiments, the external ligaments can extend along an outer portion of the soft brace. External ligaments can run close to the approximate center of joint rotation and become taut at the moment of undesired motion. The semi-rigid plates 294, 296, 298 can be used to provide stable anchoring for the external ligaments. A plurality of anchor points 300, 302 can be used to attach the external ligaments 292 to the semi-rigid plates 294, 296, 298. Compression and friction can be used to anchor apparel garment and rigid plates to the body. Length adjusting systems can be used to customize brace protection by changing the pre-tension or slack length of the external ligaments. In some embodiments, the components of the brace can be integrated into an apparel component 304. In some embodiments, the brace 290 can also include one or more compression/high friction elements to prevent drift of the apparel component and/or the brace components. For example, a shown in FIGS. 25A-25B, a compression element 306 can be positioned around a portion of the leg proximal to the target joint, a compression element 310 can be positioned around a heel of the foot, and a compression element 308 can be positioned around a portion of the foot distal to the target joint. The actual configuration and number of external ligaments can depend on the injury type. The exemplary configuration of the external cables, anchors, and other components as shown in FIGS. 25A-25B is an exemplary embodiment and it will be understood that many other configurations can be used that restrict only certain motions while leaving others free. For example, in some embodiments a soft ankle brace can also optionally include a hinge, such as a flexible hinge, that allows for motion in one plane while preventing motion in another plane.

In some embodiments, a soft joint brace for use with an ankle joint can be made as one unitary piece, for example in a shape of long sock, or the brace can include multiple pieces, for example, two separate components ("no show" sock and a calf wrap). In some embodiments, the soft joint brace for an ankle can include compression planes 306, 308, 310 applied on the foot and the calf, and a plurality of external cables 292 routed between the compression planes. As shown in the exemplary embodiment of FIG. 25B, a foot can have two compression planes, and the calf side can have a single compression plane. The compression planes are used to prevent sliding.

In some embodiments, a soft joint brace can be used to protect a shoulder. Exemplary injuries to shoulder soft tissue structures can occur, for example, during overhead activities. Shoulder injuries and dislocation are very common and can occur in both traumatic and chronic fashions. The most common injured structures of the shoulder are rotator cuff and SLAP which mainly occur as a result of excessive overhead activities (e.g. throwing) during work or sports.

To protect a shoulder, in some embodiments a brace can include one body anchor secured around the upper arm and another body anchor around the trunk. A body anchor around the trunk can require multiple planes of applied compression to avoid displacement relative to the body. Configuration of the external cables can depend on the type of motion the brace is restricting. Stretchy fabric can be used to protect the external cables from being caught onto something. An upper arm body anchor can have one or more planes of compressions applied.

Figure 26:
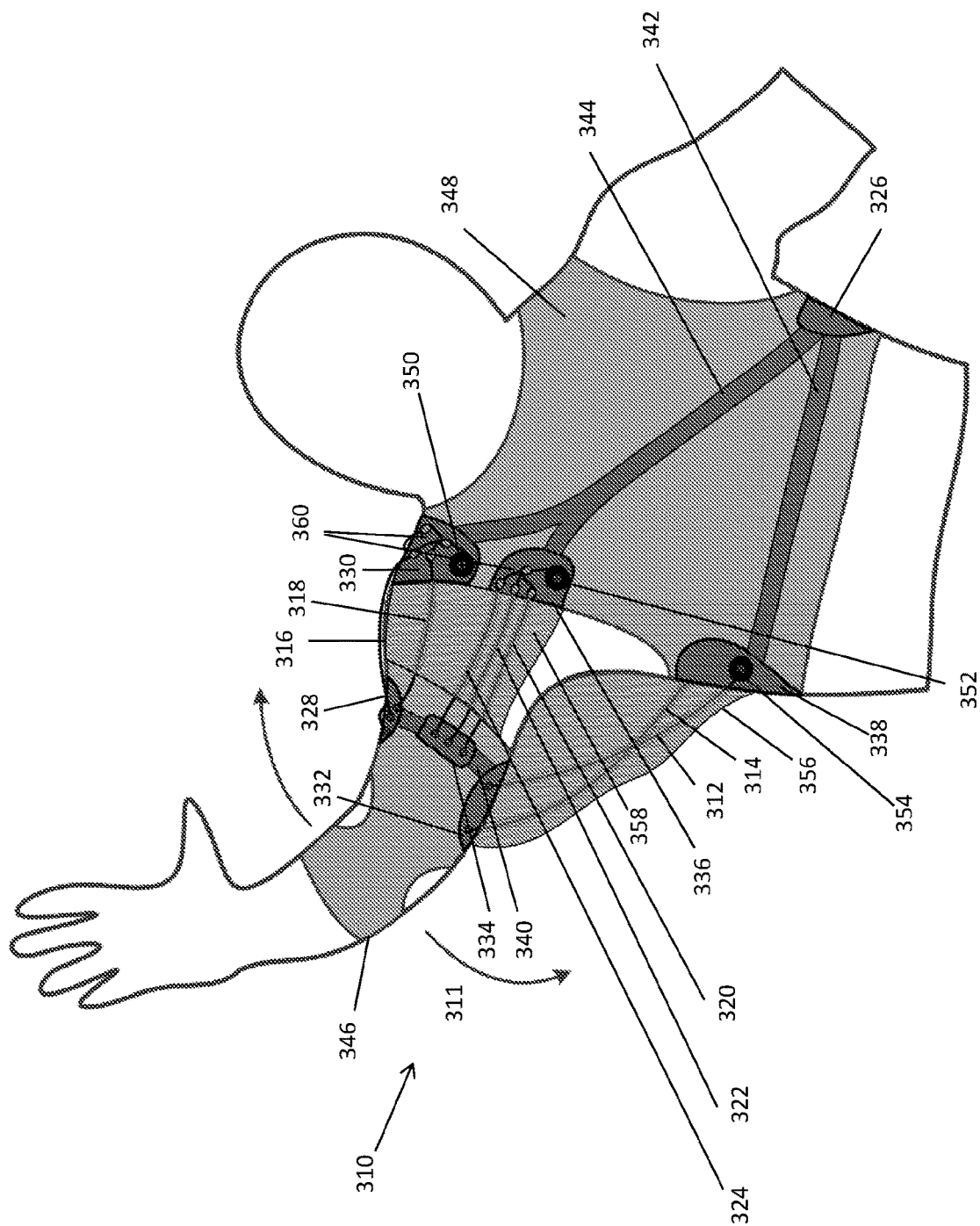
FIG. 26 illustrates an exemplary embodiment of a soft joint brace for protecting a shoulder joint.

A shoulder has a large range of motions, however a soft brace can be applied to set physical limits. In some embodiments, several external ligaments can run around the joint to stabilize the upper arm to the torso. One exemplary embodiment of the placement of the components of a soft joint brace 310 for use with a shoulder are shown in the FIG. 26, with components positioned to prevent motion in the direction shown by an arrow 311. Due to complex multi-planar mechanisms of shoulder injuries, the brace should protect the joint against multiple motions (e.g. abduction and extension). A plurality of tensile elements (external ligaments) 312, 314, 316, 318, 320, 322, 324 can be routed inside the brace using a guiding system 360, such as channels (tubes), embedded in the soft brace to keep the external ligaments in proper orientation to protect the joint in a targeted manner. External ligaments can run close to the approximate center of joint rotation and become taut at the moment of undesired motion. The brace 310 can also include adjustment mechanisms 350, 352, 354 to adjust the length of one or more of the external ligaments. Semi-rigid plates 326, 328, 330, 332, 334, 336, 338 are used to provide stable anchoring for the external ligaments at a plurality of anchor points. The semi-rigid plates are designed in a way to avoid interrupting with activity of upper are muscles (i.e. biceps). Compression and friction can be used to anchor apparel garment and rigid plates to the body using one or more compression/high friction elements. In the embodiment shown in FIG. 26, the brace 310 includes a compression element 340 around an upper portion of the arm and compression elements 342, 344 that extend laterally across the back. In some embodiments, the components can be integrated into apparel components 346, 348, which can include stretchable components 356, 358 to accommodate the types of motion associated with the shoulder joint. Length adjusting systems are used to customize brace protection by changing the pre-tension or slack length of the external ligaments. The actual configuration and number of external ligaments can depend on the biological ligament targeted for protection (for example, rotator cuff). The configuration of the external cables, anchors, and other components is an exemplary embodiment and many other configurations can be used that restrict only certain motions while leaving others free. For example, in some embodiments a soft shoulder brace can also optionally include one or more hinges, such as a flexible hinge, that allows for motion in one plane while preventing motion in another plane. The brace can be used bilaterally as well.

In some embodiments, a soft joint brace can be used to protect a hand and/or wrist. Injury to the scapholunate (S-L) ligament (near the ulna and radius) is the most common wrist injury and it typically occurs through hyperextension of the wrist from a fall on an outstretched hand or an acute twisting injury. Ulnar collateral ligament is a strong ligament between the phalanx and metacarpus at the metacarpophalangeal joint that supports the thumb when pinching or gripping. The injury to this ligament happens when you fall onto the outstretched thumb and is more likely if the thumb is gripping something at the same time. Falling when skiing while holding a ski pole is a common cause hence the name frequently given to this injury (skier's thumb).

Figures 27A, 27B:
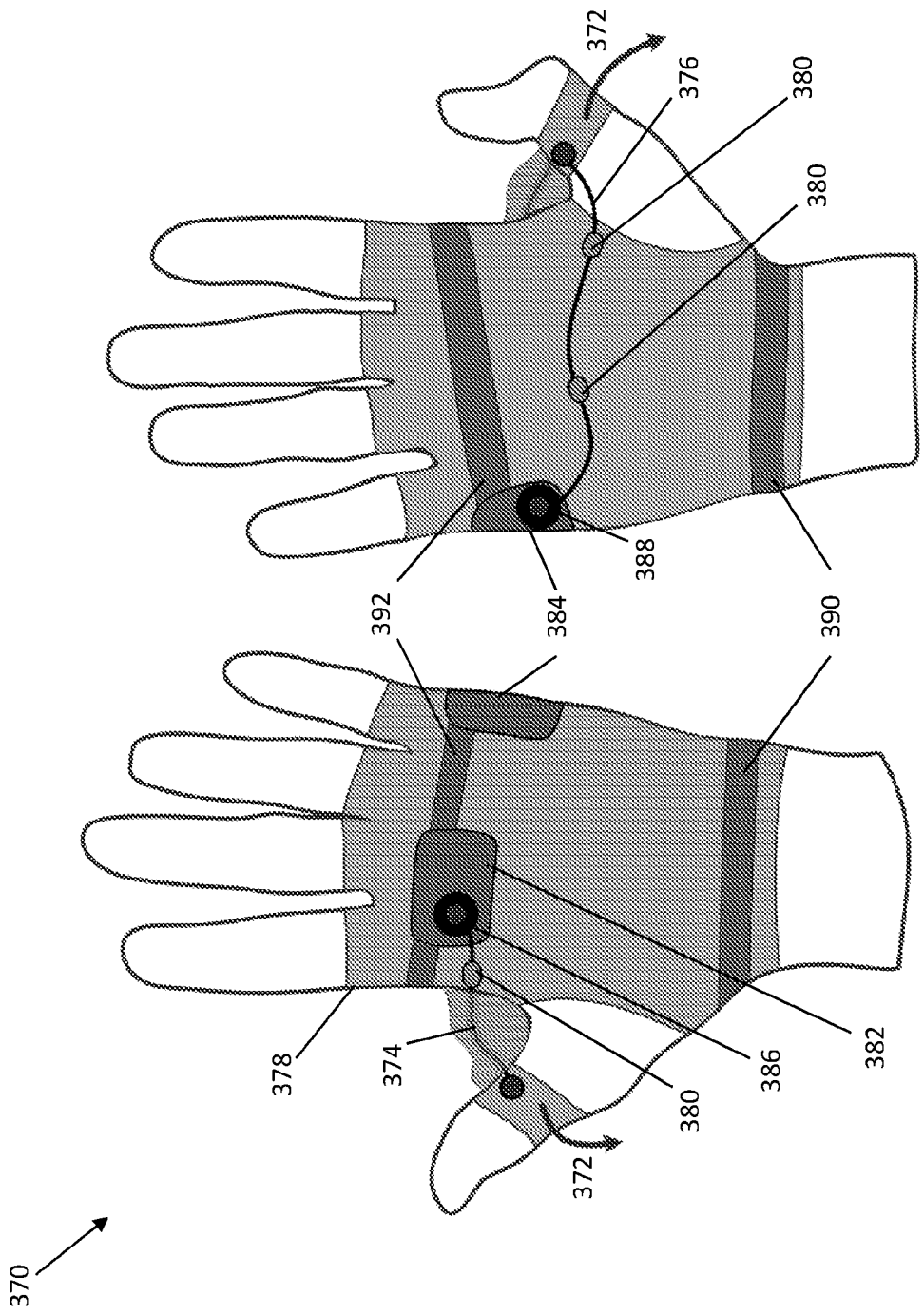
FIG. 27A and FIG. 27B illustrate back and front views of an exemplary embodiment of a soft joint brace for protecting a hand and/or wrist.

To protect against thumb injuries, in some embodiments a brace can include one body anchor placed on the palm and another body anchor on the thumb, as will be explained in more detail below. One or more external cables can be used to connect the two body anchors and prevent undesired motion of the thumb. Stretchy fabric can be used to protect an external cable from getting caught onto something. The palm body anchor can have at least two planes of compression applied to prevent slippage In some embodiments, multiple external ligament modules (tensile elements) can be routed through the soft brace to prevent wrist hyper extension, as shown in FIGS. 28A-28B, and excessive thumb outward rotation, as shown in FIGS. 27A-27B. As shown in FIGS. 27A-27B, a soft joint brace 370 can be configured to prevent motion in the direction shown by arrow 372 to prevent excessive outward motion of the thumb. In some embodiments, the external ligaments can be routed inside the brace 370 using a guiding system 380 including a plurality of guides and channels (tubes) embedded in the soft brace 370 to keep the external ligaments in proper orientation to protect the joint in a targeted manner. External ligaments 374, 376 can extend between a portion of the thumb and to a semi-rigid plate 382 on a back of the hand (shown in FIG. 27A) and to a semi-rigid plate 384 on the opposite lateral side of the hand. Each semi-rigid plate 382, 384 includes an adjustment mechanism 386, 388 to adjust the length of the external ligaments 374, 376. External ligaments can run close to the approximate center of joint rotation and become taut at the moment of undesired motion. The semi-rigid plates are used to provide stable anchoring for the external ligaments. Compression and friction can be used to anchor apparel garment and rigid plates to the body. In the embodiment shown in FIGS. 27A-27B, the brace 370 includes first and second compression elements 390, 392 that extend around the hand near the wrist and below the fingers. In some embodiments, the components can be integrated into an apparel component 378. Length adjusting systems are used to customize brace protection by changing the pre-tension or slack length of the external ligaments. The actual configuration and number of external ligaments will depend on the type of injury.

As shown in FIGS. 28A-28B, a soft joint brace 400 can be configured to prevent motion in the direction shown by arrows 402, 403 to prevent hyperextension of the wrist. In some embodiments, external ligaments 404, 406, 408, 410, 412, 414 can be routed inside the brace 400 using a guiding system 416, 418 that includes a plurality of guides and channels (tubes) embedded in the soft brace 400 to keep the external ligaments in proper orientation to protect the joint in a targeted manner. On the front of the hand as shown in FIG. 28A, external ligaments 404, 406, 408 extend between a semi-rigid plate 420 on the wrist to a semi-rigid plate 422 on a position of the hand proximal to the fingers. The external ligaments are coupled to the semi-rigid plate 422 using a plurality of anchor points 424 and to the semi-rigid plate 420 using an anchor in the form of an adjustment mechanism 426 for adjusting the tension of the external ligaments 404, 406, 408. On the back of the hand as shown in FIG. 28B, external ligaments 410, 412, 414 extend between a semi-rigid plate 434 on the wrist to a semi-rigid plate 436 on a position of the hand proximal to the fingers. The external ligaments are coupled to the semi-rigid plate 436 using a plurality of anchor points 438 and to the semi-rigid plate 434 using an anchor in the form of an adjustment mechanism 440 for adjusting the tension of the external ligaments 410, 412, 414. In the embodiment shown in FIGS. 28A-28B, the brace 400 includes first and second compression elements 428, 430 that extend around the hand near the wrist and below the fingers. In some embodiments, the components can be integrated into an apparel component 432.

FIGS. 27A-27B and FIGS. 28A-28B are exemplary embodiments of soft braces for use with a hand and wrist and illustrate exemplary positioning of the external cables and anchors. It is understood that many other configurations can be used that restrict only certain motions while leaving others free. For example, in some embodiments a soft hand/wrist brace can also optionally include one or more hinges, such as a flexible hinge, that allows for motion in one plane while preventing motion in another plane. The brace can be used bilaterally as well.

In some embodiments, a soft joint brace can be used to protect an elbow and lower the risk of elbow injuries. Injuries to the elbow joint are mainly chronic (e.g. repetitive excessive motion and overuse) but also occur in a traumatic fashion. The most common elbow injuries are the ruptures of the ulnar collateral ligament, and tennis elbow (strained and/or inflamed lateral epicondylitis) and golfers elbow (strained and/or inflamed medial epicondyle). These injuries occur primarily due to excessive elbow abduction-adduction and hyper extension. To prevent against elbow injuries, in some embodiments a brace can include one body anchor placed on the upper arm and another body anchor placed on the lower arm. One or more external cables can connect the two body anchors and prevent undesired motion of the elbow. Both upper and lower arm body anchors can use at least one plane of compression to prevent slippage.

Figure 29:
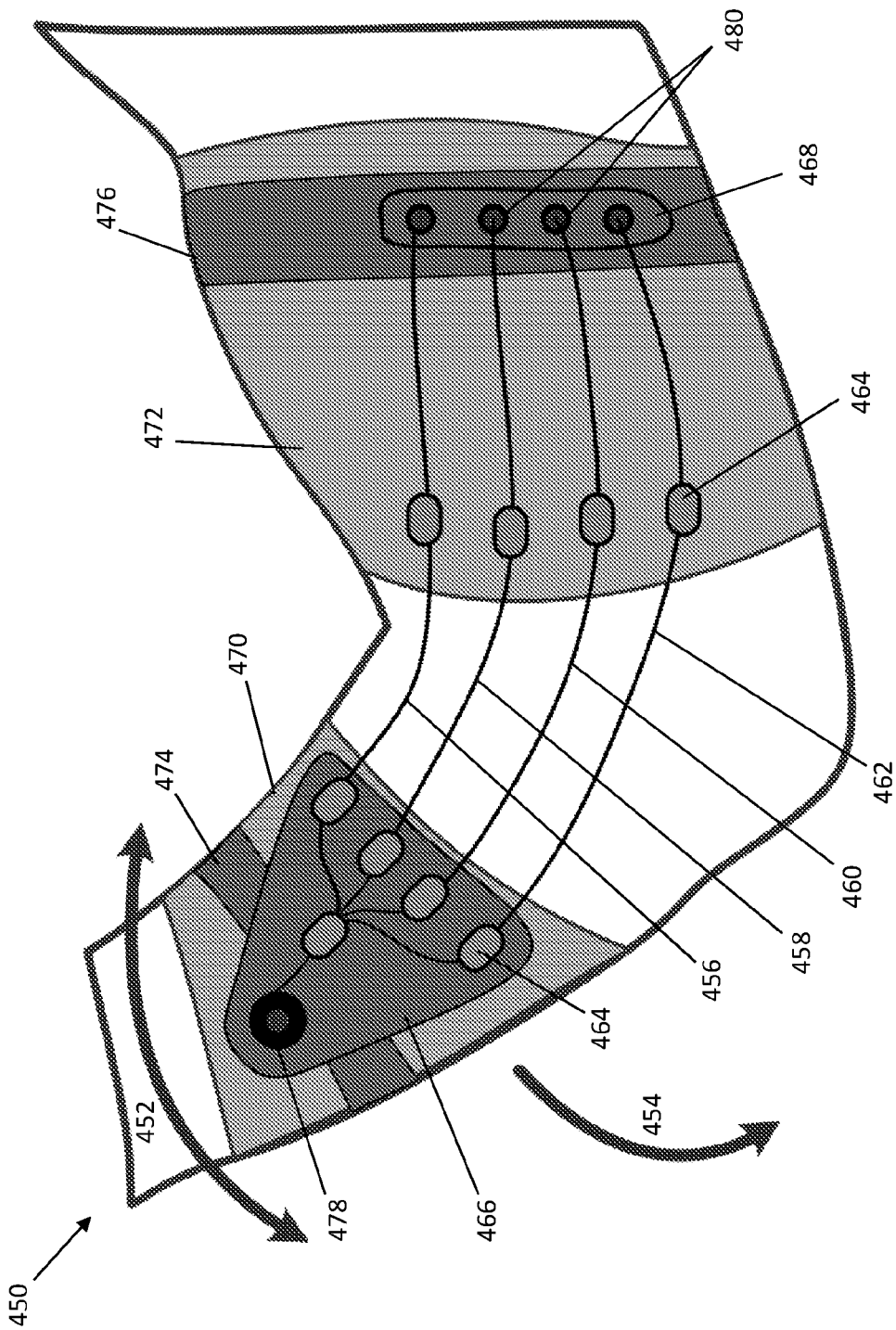
FIG. 29 illustrates an exemplary embodiment of a soft joint brace for protecting an elbow joint.

In some embodiments, a plurality of external ligaments 456, 458, 460, 462 can run around the joint to stabilize the elbow joint, as shown in the exemplary brace illustrated in FIG. 29 to prevent motion in the directions shown by arrows 452, 454. The external ligaments are routed inside the brace using a guiding system, such as channels (tubes), embedded in the soft brace to keep the external ligaments in proper orientation to protect the joint in a targeted manner. For example, the brace 450 can include one or more guides 464 to guide the position of the external ligaments. External ligaments run close to the approximate center of joint rotation and become taut at the moment of undesired motion. Semi-rigid plates 466, 468 are used to provide stable anchoring for the external ligaments. The external ligaments are coupled to the semi-rigid plate 468 using a plurality of anchor points 480. The semi-rigid plates are designed in a way to avoid interrupting with activity of upper are muscles (i.e. biceps). Compression and friction can be used by compression elements 474, 476 to anchor apparel garments 470, 472 and rigid plates to the body. Length adjusting systems, such as an adjustment mechanism 478, can be used to customize brace protection by changing the pre-tension or slack length of the external ligaments. The actual configuration and number of external ligaments will depend on the biological ligament targeted for protection (for example, UCL). An exemplary configuration of external cables, anchors, and other components is shown in FIG. 29, and many other configurations can be used that restrict only certain motions while leaving others free. For example, in some embodiments a soft elbow brace can also optionally include one or more hinges, such as a flexible hinge, that allows for motion in one plane while preventing motion in another plane. The brace can be used bilaterally as well.

In some embodiments, a soft joint brace can be used to protect a spine. Any of the ligaments in a back can be sprained. Injuries that can cause a sprain include a sudden contraction or twisting of the ligament, a hard blow to the ligament, or a fast and forceful straightening of the ligament. 8 out of 10 Americans have back problems throughout their lifetimes. 39% of back injuries affect daily tasks, 37% affects sleep and 38% affects exercises. To protect against lower back injuries, in some embodiments a brace can include one or more body anchors whose number and position on the body depends on the type of motion that is being restricted. To protect a specific segment of the spine, two compression planes can be applied above and below the segment. One or more external cables can be anchored to the compression planes and prevent undesired motion of the segment. To protect a larger segment of the lower back, two or more body anchors can be used with one placed around the trunk and one around the lower body. Placement of the compression planes and external cables can depend on what segment of the spine is being protected. The brace can prevent both incline motion and/or twisting.

Figure 30:
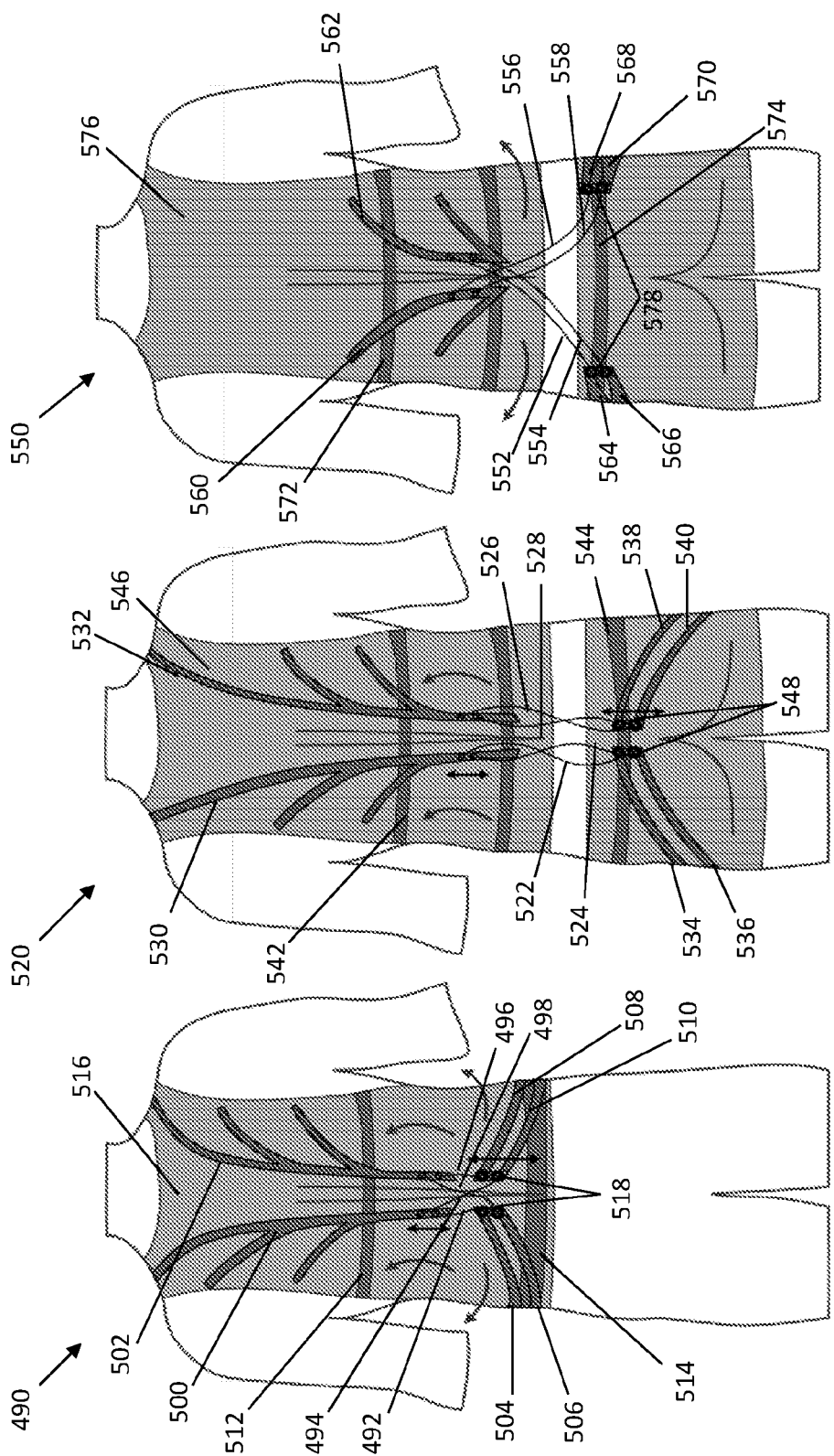
FIGS. 30A, 30B, and 30C are exemplary embodiments of a soft joint brace for protecting the upper and/or lower back.

In some embodiments, due to complex structure and high number of joints in human spine, a brace for the spine can protect the thoracic and lumbar spine as two bodies instead of protecting each spinal joint separately. A plurality of external ligaments can run around the torso in the front and back to stabilize the thorax and lumbar spine (lower back) against excessive side-to-side bending (lateral bending) and hyper extension, as illustrated in the exemplary braces shown in FIG. 30A and FIG. 30B. As shown in FIG. 30A, external ligaments 492, 494, 496, 498 are routed inside a brace 490 using a guiding system, such as channels (tubes), embedded in the soft brace to keep the external ligaments in proper orientation to protect the joint in a targeted manner by prevent motion in the directions indicated by the arrows shown in FIG. 30A, which includes excessive lateral bending and stabilization of the thoracic spine. The semi-rigid plates 500, 502, 504, 506, 508, 510 are used to provide stable anchoring for the external ligaments. The semi-rigid plates can be designed in a way to avoid interrupting with rib cage expansion during breathing. Compression and friction can be used by compression elements 512, 514 to anchor apparel garment 516 and rigid plates to the body. Length adjusting systems can be used to customize brace protection by changing the pre-tension or slack length of the external ligaments using adjustment mechanisms 518.

As shown in an exemplary embodiment of a brace in FIG. 30B, external ligaments 522, 524, 526, 528 are routed inside a brace 520 using a guiding system, such as channels (tubes), embedded in the soft brace to keep the external ligaments in proper orientation to protect the joint in a targeted manner by prevent motion in the directions indicated by the arrows shown in FIG. 30B, which includes stabilization of the thoracic and lumbar spine. The semi-rigid plates 530, 532, 534, 536, 538, 540 are used to provide stable anchoring for the external ligaments. The semi-rigid plates can be designed in a way to avoid interrupting with rib cage expansion during breathing. Compression and friction can be used by compression elements 542, 544 to anchor apparel garment 546 and rigid plates to the body. Length adjusting systems can be used to customize brace protection by changing the pre-tension or slack length of the external ligaments using adjustment mechanisms 548.

In an exemplary embodiment shown in FIG. 30C, a brace 550 can include a plurality of external ligaments 552, 554, 556, 557 to prevent motion in the directions indicated by the arrows shown in FIG. 30C to stabilize the lower back. The semi-rigid plates 560, 562, 564, 566, 568, 570 are used to provide stable anchoring for the external ligaments. Compression and friction can be used by compression elements 572, 574 to anchor apparel garment 576 and rigid plates to the body. Length adjusting systems can be used to customize brace protection by changing the pre-tension or slack length of the external ligaments using adjustment mechanisms 578. The actual configuration and number of external ligaments can depend on the injury type, and any combination of external ligaments can be used in any combination to protect different parts of the spine.

The configuration of the external cables, anchors and other components shown in FIGS. 30A, 30B, 30C are exemplary embodiments, and it is understood that many other configurations can be used that restrict only certain motions while leaving others free. For example, in some embodiments a soft back brace can also optionally include one or more hinges, such as a flexible hinge, that allows for motion in one plane while preventing motion in another plane. Improved trunk stability will also help to reduce the risk of lower extremity injuries such ACL tears.

In some embodiments, a soft joint brace can be used to protect a hip. The hip joint is very complex and there are numerous reasons for possible injury, such as groin strain, bursitis, hamstrings pull, snapping hip and etc. In some embodiments, a brace can be used for muscle strain.

There are as many as six muscles involved with flexion of the hip, and any of them can be strained. But the one that gets the most attention is the iliopsoas, a hip flexor that can be strained when it contracts forcefully, especially when the leg is fully extended or prevented from moving. Kicking and sprinting are the most common movements that cause strained hip flexors. Bending at the waist can be difficult after the injury has occurred. To protect against hip injuries, in some embodiments a brace can include one or more body anchors placed above the hips and one or more body anchors placed at the lower body below the hips. One or more external cables can connect the body anchor at the two locations and prevent undesired motion of the hips. The body anchors can use one or more planes of compression to prevent slippage. Placement of the compression planes and the external cables can depend on type of hip motion is being protected against.

Figure 31:
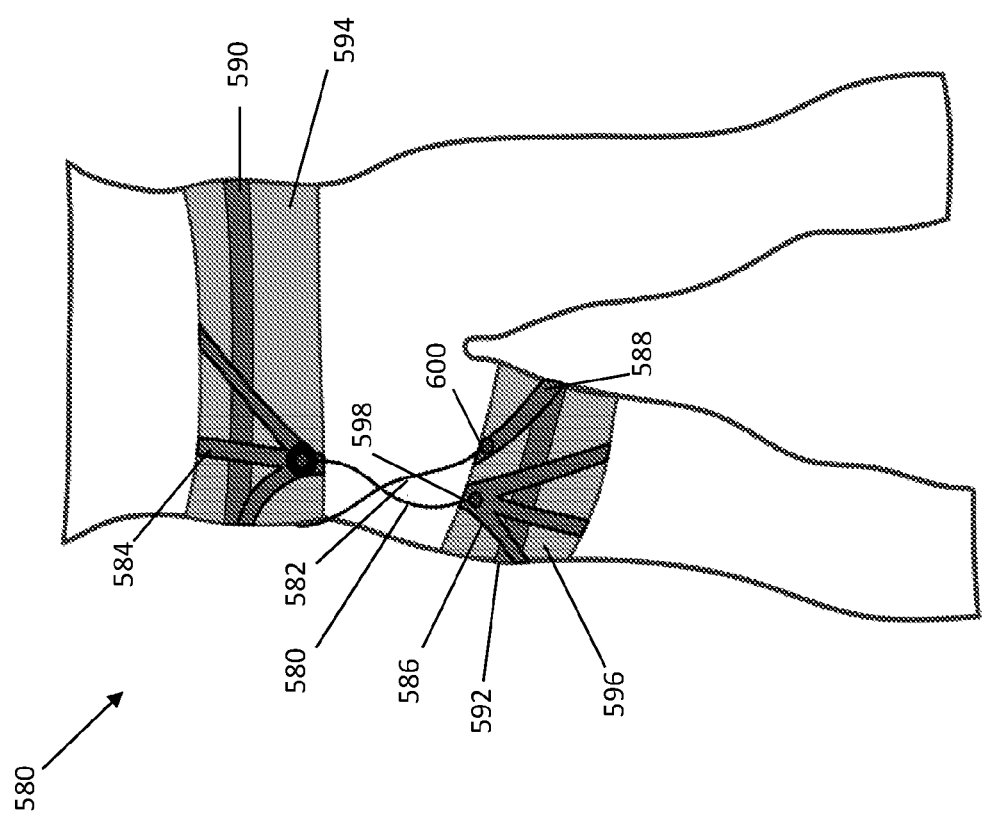
FIG. 31 is an exemplary embodiment of a soft joint brace for protecting a hip joint.

In some embodiments, a plurality of external ligaments can be used to control the hip motion in the sagittal (flexion-extension) and/or coronal (abduction-adduction), as shown in FIG. 31, which illustrates an exemplary embodiment of a soft brace 580 for reducing hip injuries. External ligaments 580, 582 can be routed inside the brace using a guiding system, such as channels (tubes), embedded in the soft brace to keep the external ligaments in proper orientation to protect the joint in a targeted manner. External ligaments can run close to the approximate center of joint rotation and become taut at the moment of undesired motion. Semi-rigid plates 584, 586, 588 can be used to provide stable anchoring for the external ligaments. The semi-rigid plates can be designed in a way to avoid interrupting with upper leg muscles (quadriceps). Compression and friction can be used by compression elements 591, 592 positioned around the waist and thigh to anchor apparel garment 594, 596 and rigid plates to the body. Length adjusting systems can be used to customize brace protection by changing the pre-tension or slack length of the external ligaments. As shown in FIG. 31, an adjustment mechanism is positioned on the semi-rigid plate 584 to allow for adjusting the tension in the external ligaments, which are connected at their other end to the semi-rigid plates 586, 588 with anchor points 598, 600. The actual configuration and number of external ligaments will depend on the injury type (i.e. groin injury). The configuration of the external cables and anchors is an exemplary embodiment of a hip brace, and it is understood that many other configurations can be used that restrict only certain motions while leaving others free. For example, in some embodiments a soft hip brace can also optionally include one or more hinges, such as a flexible hinge, that allows for motion in one plane while preventing motion in another plane. Improved hip stability in trunk stability can also help to reduce the risk of knee injuries such ACL tears. A brace can be used bilaterally as well.

Figure 32:
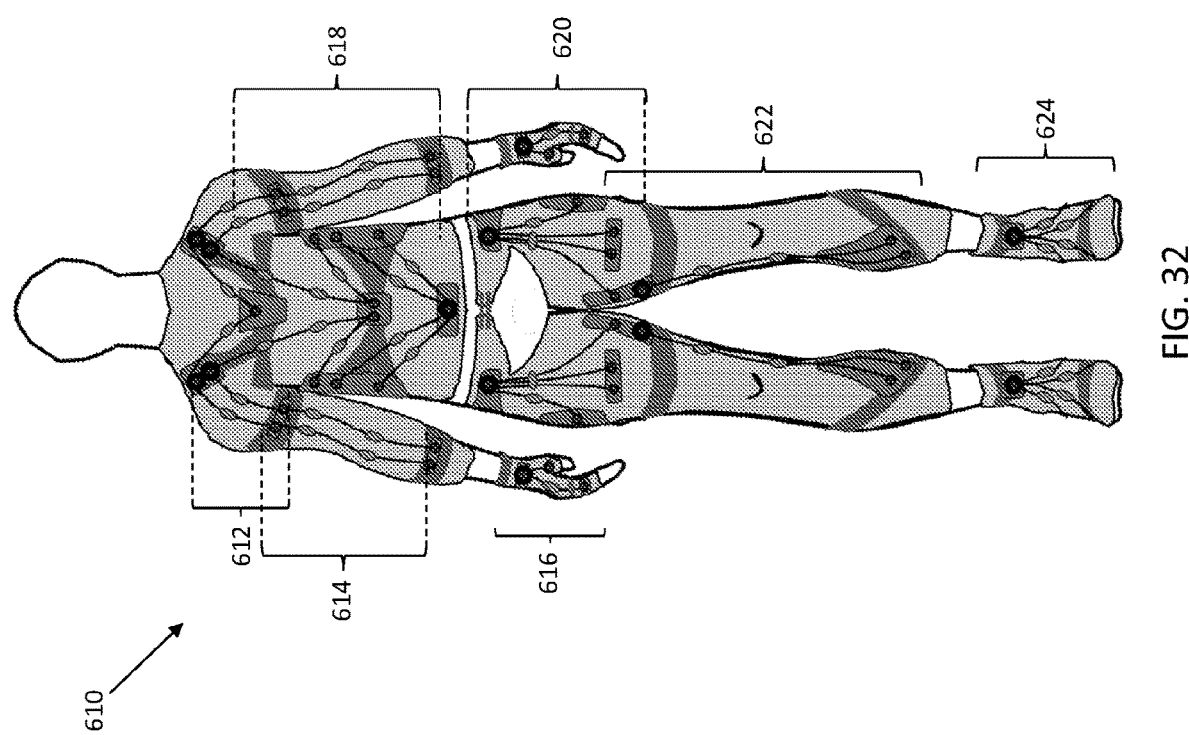
FIG. 32 is an exemplary embodiment of a whole-body soft brace.

In some embodiments, a soft joint brace can be used for whole body protection. In some embodiments, a transparent suit can worn under a uniform (for example, for soldiers) or embedded in a garment (for example, for athletes) and can offers multi joint protection for major joints of the body (i.e. wrist, elbow, shoulder, back, hip, knee and/or ankle) during demanding activities which predispose the individuals to multi joint traumatic injuries (for example, combat situations). The configuration of components for each joint can be any of those described herein. FIG. 32 illustrates an exemplary embodiment of a whole body brace for protection of a plurality of joint and for lowering the risk of individual and/or multi joint injuries. A whole body brace 610 can include components for protecting a plurality of joints. For example, the whole body brace 610 can include a portion that acts as a soft shoulder brace 612, a soft elbow brace 614, a soft wrist and/or hand brace 616, a soft back brace 618, a soft hip brace 620, a soft knee brace 622, and/or a soft ankle brace 624.

In some embodiments, a soft bracing approach can be used that restricts injurious joint motion in a targeted and customizable manner. The soft brace mimics the function of biological ligaments and consists of inextensible tensile elements (external ligament) anchored to the body using a soft, functional apparel. Soft bracing can offer comparable joint protection to rigid bracing without disrupting normal joint function and athletic performance.

Example: Soft Bracing Approach to Lower the Risk of ACL Injuries

Figure 33A:
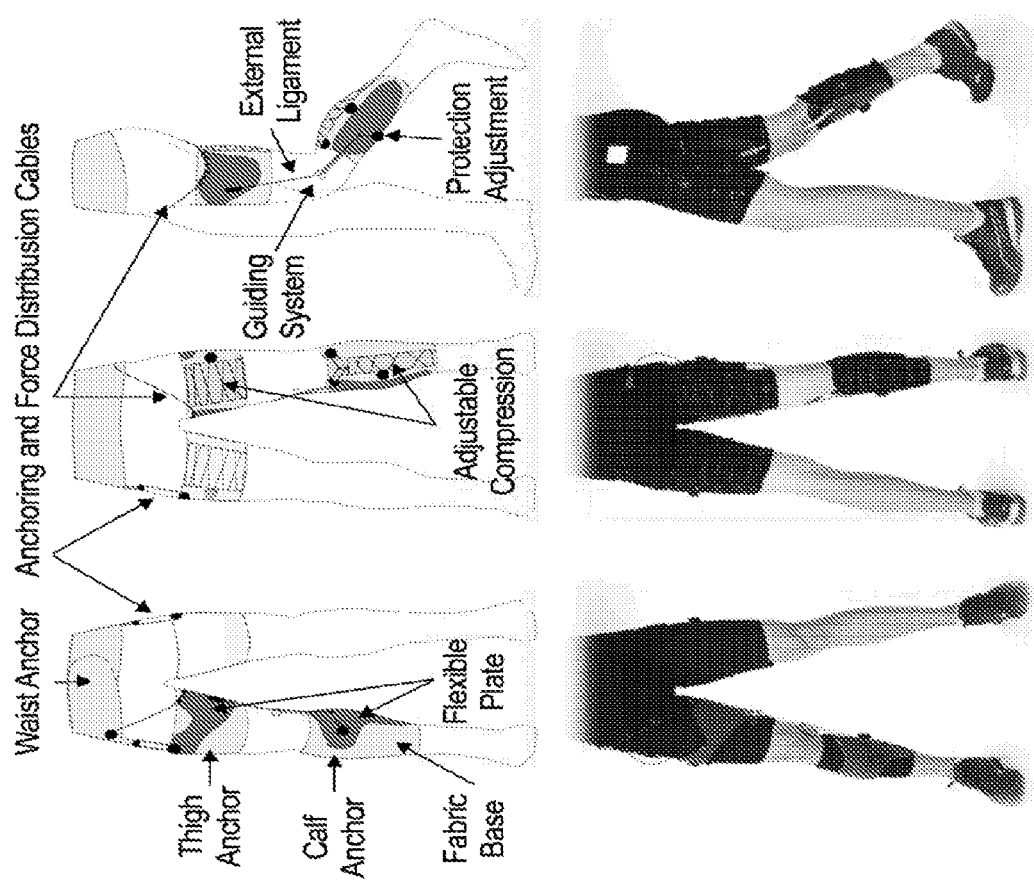
FIGS. 33A, 33B, 33C, and 33D illustrate an embodiment of a soft bracing technique relating to ACL injuries.
Figures 33B, 33C:
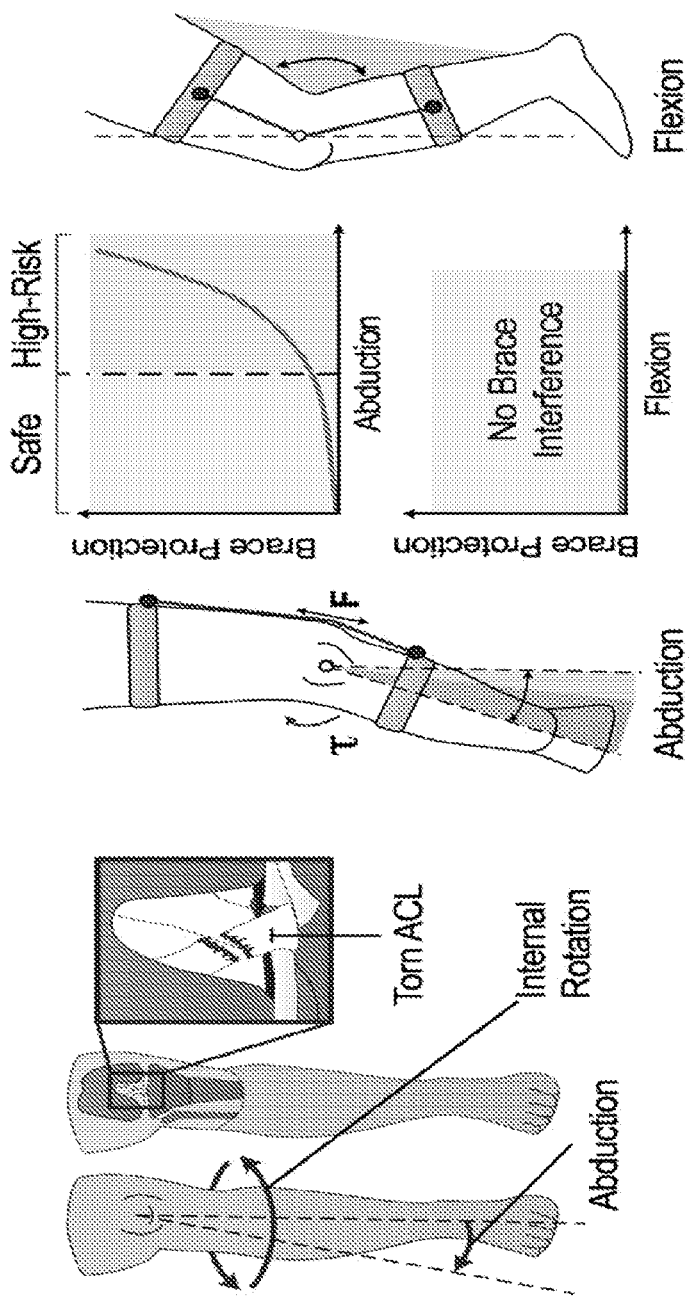

In some embodiments, a soft bracing approach, inspired by the function of the biological ligaments in joints, can be used, which protects a joint, such as the knee, when required (e.g. high-risk movements) without disrupting normal joint function and athletic performance. Rather than constraining the joint, the protective role of the knee's biological ligament is augmented with an external ligament anchored to the body by means of a loadbearing soft garment. For example, advanced functional apparel design techniques can be used to develop a soft, conformable and loadbearing brace that anchors securely, yet comfortably, to the waist, thigh and calf (FIG. 33A). An external ligament (for example, in the form of an inextensible tensile element) can be integrated into the soft brace, following the configuration identified from a series of assessments using an instrumented 3D printed mechanical knee (FIG. 34). When knee abduction, which is the primary contributor to ACL injury mechanism and is illustrated in FIG. 33B, exceeds a predefined safe range, the external ligament becomes taut and restricts further abduction rotation without disrupting knee flexion, as illustrated in FIG. 33C. This approach provides a customizable joint protection through the adjustment of the slack length of the external ligament (FIG. 33D).

To optimize the load distribution and minimize brace drift and discomfort, anchoring components can be connected to each other with force distribution cables and secured onto the body with adjustable compression mechanisms (FIGS. 35A-35C and FIGS. 36A-36D). Flexible thermoplastic plates can be incorporated into the thigh and calf anchors (the flexible plates in FIG. 33A) to provide stable anchoring foundation for the primary loadbearing modules (i.e. external ligament and force distribution cables). In order to minimize unwanted resistance during knee flexion and to ensure consistent protection against knee abduction through range of knee flexion, the external ligament can be routed through the approximate knee center of rotation in the sagittal plane using a guiding system (FIG. 33D).

Figure 33D:
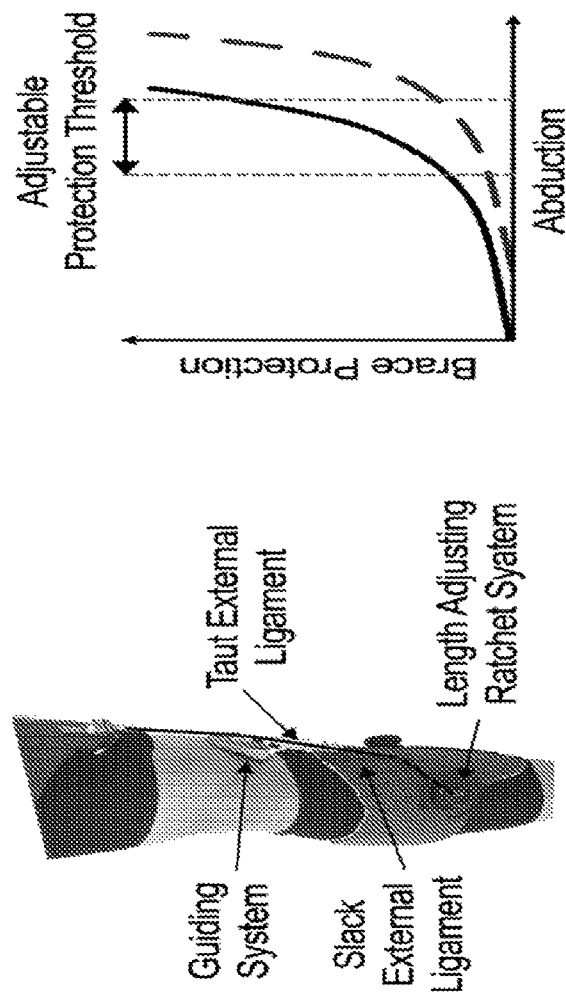

FIGS. 33A, 33B, 33C and 33D illustrate an embodiment of a soft bracing technique for targeted and adjustable protection against ACL injuries. FIG. 33A illustrates an exemplary soft brace design and functional prototype. FIG. 33B illustrates a common mechanism of non-contact ACL injuries (valgus collapse) primarily involves knee abduction with or without internal tibial rotation during shallow knee flexion angles (<30°). FIG. 33C illustrates an exemplary targeted knee protection concept against excessive abduction without interrupting flexion. The lines in both graphs represent the level of protection offered to the knee by the soft brace. FIG. 33D shows that the protection level offered by the brace can be personalized by adjusting the protection threshold through an external ligament slack length adjustment system.

Figure 37A:
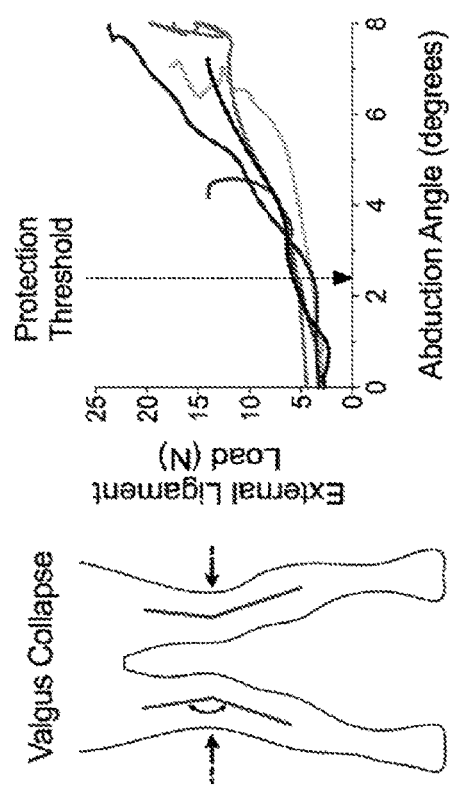
Figure 37B:
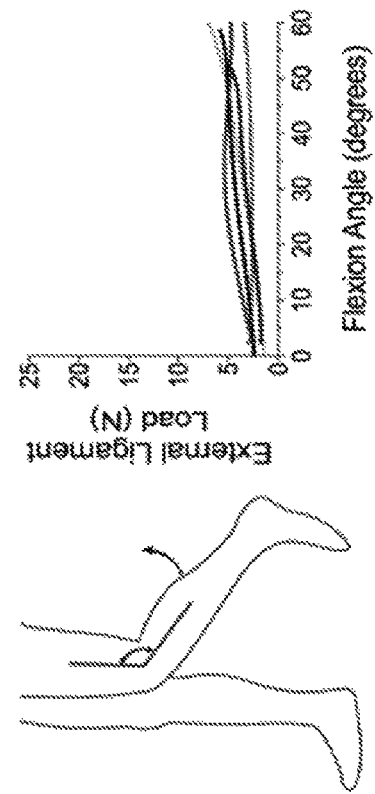

In a test of an exemplary knee brace, the soft knee brace was tested in five healthy male subjects performing valgus collapse (voluntary bilateral knee valgus stress at shallow knee flexion to simulate leg posture during ACL injury) and knee flexion maneuvers. During valgus collapse, the brace demonstrated a non-linear behavior with minimal changes in external ligament tension at low knee abduction angles followed by 2.4 fold increases in external ligament tension ($p=0.005$; Table 3) under increased abduction angles beyond average $2.4 \pm 1.4°$ (protection threshold; FIG. 37A). However, during knee flexion, external ligament tension remained almost unchanged (FIG. 37B), demonstrating minimal restriction during this movement. The external ligament tension pattern was comparable to previously reported strain patterns of native human ACL under knee abduction rotation (FIG. 37C). FIGS. 37A-37E illustrate soft brace prototype function under valgus loading and knee flexion. FIG. 37A illustrates non-linear changes in external ligament tension (measured by a uniaxial loadcell across thigh attachment) in response to increased knee abduction. FIG. 37B illustrates changes in external ligament tension during knee flexion. FIG. 37C illustrates non-linear changes in ACL tension (measured in situ using a miniaturized DVRT strain gage) in human cadaveric knees ($n=19$; mean±SD; reconstructed with permission from Kiapour et al. 2015). Data indicates almost no changes in ACL strain under small abduction angles followed by significant increases in ACL strain under increased abduction angles (* p<0.001, Paired-Sample t-test). FIG. 37D illustrates changes in external ligament tension patterns during valgus collapse in response to increased external ligament pre-tension level. Solid lines represent high pre-tension conditions and dotted lines represent normal pre-tension condition also presented in FIG. 37A. FIG. 37E illustrates changes in peak knee abduction during valgus collapse between normal and high pre-tension conditions (* p=0.005). Each line in FIGS. 37A, 37B, 37D and 37E, represents one subject.

Soft brace performance was also assessed relative to no bracing and rigid bracing (DonJoy Armor ACL FourcePoint) conditions, in restricting knee abduction during a dynamic high-risk task (i.e. single-legged cross drop) and in improving stability (i.e. single-legged standing and Y balance tests). Soft bracing restricted both knee abduction and internal rotations, to the same levels observed under rigid bracing (FIG. 38A, FIG. 38B and Table 2). Peak knee abduction during landing has been validated as a reliable predictor for risk of non-contact ACL injuries. Previous clinical studies have shown subjects with high peak knee abduction, measured in the lab, were at higher risk for tearing their ACL during the game. Several video analysis studies of real injuries have shown increased knee abduction and internal rotation at the time of ACL injury. These findings are supplemented with several reports indicating significant increases in ACL loading caused by knee abduction and internal rotation. Although both rigid and soft braces have been designed to primarily restrict knee abduction, the anatomic coupling between knee abduction and internal rotation could have resulted in observed reductions in peak knee internal rotation. Neither bracing techniques affected peak knee flexion during cross drop, as shown in Table 2. Table 2 shows data relating to peak knee rotations during the stance phase of single-legged cross drop. Each individual data point is the average of 6 trials. All outcome measures were defined as continuous variables. Peak knee flexion and internal rotation were compared between the groups using Repeated Measures ANOVA with a Tukey posthoc correction for multiple comparisons. Peak knee abduction was compared between the groups using non-parametric Friedman test with a Benjamini Hochberg posthoc correction for multiple comparisons.

TABLE 2

|  |  | Subjects | | | | | | | ** F or $\chi^2$ | *** Test of |
|---|---|---|---|---|---|---|---|---|---|---|
|  | Bracing | 1 | 2 | 3 | 4 | 5 | Mean ± SD | * P-Value | Statistic | Normality |
| Peak Knee Flexion (degrees) | No | 69.9 | 59.9 | 59.3 | 44.2 | 57.0 | 56.1 ± 9.9 | $P_{NR}$ = 0.055 | F = 4.1 | P = 0.607 |
|  | Rigid | 71.4 | 64.5 | 51.2 | 49.1 | 64.1 | 60.1 ± 9.5 | $P_{NS}$ = 0.705 |  |  |
|  | Soft | 68.2 | 56.3 | 53.0 | 47.8 | 60.8 | 57.2 ± 7.8 | $P_{RS}$ = 0.178 |  |  |
| Peak Knee Abduction (degrees) | No | 3.0 | 4.2 | 7.8 | 3.9 | 5.9 | 4.9 ± 1.9 | $P_{NR}$ = 0.034 | $\chi^2$ = 7.6 | P = 0.043 |
|  | Rigid | 0.9 | 2.8 | 1.4 | 1.6 | 2.8 | 1.9 ± 0.9 | $P_{NS}$ = 0.040 |  |  |
|  | Soft | 1.0 | 1.2 | 1.4 | 2.9 | 3.4 | 1.9 ± 1.1 | $P_{RS}$ = 0.752 |  |  |
| Peak Knee Internal Rotation (degrees) | No | 10.7 | 19.0 | 15.9 | 12.4 | 14.8 | 14.6 ± 3.2 | $P_{NR}$ = 0.008 | F = 10.4 | P = 0.530 |
|  | Rigid | 9.0 | 9.6 | 5.8 | 6.6 | 6.6 | 7.5 ± 1.6 | $P_{NS}$ = 0.015 |  |  |
|  | Soft | 10.3 | 8.4 | 4.3 | 10.9 | 7.5 | 8.3 ± 2.6 | $P_{RS}$ = 0.892 |  |  |

* Adjusted P value, $P_{NR}$: No Bracing vs. Rigid Bracing, $P_{NS}$: No Bracing vs. Soft Bracing, $P_{RS}$: rigid Bracing vs. Soft Bracing.
** F-Statistic for Repeated Measures ANOVA and $\chi^2$ (Friedman Statistic) for non-parametric Friedman Test.
*** Shapiro-Wilk test, P > 0.05 indicates normal distribution.
SD: Standard Deviation.

A soft bracing approach can offer adjustable protection level to resist excessive knee rotation. By increasing the external ligament pre-tension level, the protection threshold can be adjusted (FIG. 37D and Table 3) and make the brace more protective, restricting maximum knee abduction and internal rotation further (FIG. 37E, FIG. 38C and FIG. 38D). This approach can addresses the physiologic between-subjects variability in intrinsic risk factors (e.g. joint laxity) in addition to the different activity related injury risk and requirements for athletic performance. Further adjustments of type, size and number of external ligaments can address a wider range of joint protection requirements. Table 3 shows data relating to changes in external ligament tension and knee abduction during valgus collapse maneuver.

TABLE 3

|  |  | Subjects | | | | | | * t or z | ** Test of |
|---|---|---|---|---|---|---|---|---|---|
|  |  | 1 | 2 | 3 | 4 | 5 | Mean ± SD | P-Value Statistic | Normality |
| Normal Pre-Tension | Pre-Tension Level (N) | 3 | 4 | 7 | 6 | 6 | 5 ± 2 | 0.005 t = 5.7 | P = 0.320 |
|  | Maximum Tension (N) | 14 | 24 | 16 | 18 | 14 | 17 ± 4 |  |  |

TABLE 3-continued

| | | Subjects | | | | | | | *t or z | **Test of |
|---|---|---|---|---|---|---|---|---|---|---|
| | | 1 | 2 | 3 | 4 | 5 | Mean ± SD | P-Value | Statistic | Normality |
| High Pre-Tension | Pre-Tension Level (N) | 13 | 13 | 9 | 10 | 12 | 11 ± 2 | 0.001 | t = 7.9 | P = 0.142 |
| | Maximum Tension (N) | 24 | 33 | 22 | 26 | 34 | 28 ± 5 | | | |
| Protection Threshold (degrees) | Normal Pre-Tension | 1.0 | 2.5 | 2.4 | 4.5 | 1.4 | 2.4 ± 1.4 | 0.043 | z = 2.0 | P = 0.020 |
| | High Pre-Tension | 0.7 | 1.0 | 0.8 | 0.5 | 0.4 | 0.7 ± 0.2 | | | |
| Peak Knee Abduction (degrees) | Normal Pre-Tension | 7.2 | 8.0 | 8.0 | 7.2 | 4.6 | 7.0 ± 1.4 | 0.006 | t = 5.3 | P = 0.065 |
| | High Pre-Tension | 3.9 | 4.3 | 5.9 | 3.6 | 3.6 | 4.3 ± 1.0 | | | |

* t-Statistic for Paired-Sample t-Test and z-Statistic for Related Samples Wilcoxon Signed Rank Test.
** Shapiro-Wilk test, P > 0.05 indicates normal distribution.
SD: Standard Deviation FIGS. 38A-38F illustrate relative biomechanical efficacy of soft bracing. FIG. 32A and FIG. 32B illustrate peak knee abduction (*p<0.05) and internal rotation (* p<0.020) during single-legged cross drop. FIG. 38C and FIG. 38D illustrate changes in peak knee abduction (* p=0.026) and internal rotation (* p=0.043) during single-legged cross drop caused by increased external ligament pre-tension levels under soft bracing condition (Paired-Sample t-test).

In addition to multi-planar joint protection, a soft bracing approach can result in improved knee stability and overall balance (FIG. 38E, which illustrates body medial-lateral COP sway during single-legged standing balance (* p<0.05), and FIG. 38F, which illustrates Y-balance composite score (* p=0.003) with Mean±SD (n=5/group). Compared to no bracing condition, soft and rigid braces improved stability in the coronal plane as shown by −24% decreases in medial-lateral sway of the body center of pressure (COP) during standing balance (FIG. 38E and Table 4). Table 4 shows data relating to body center of pressure sway during single-legged standing balance. Each individual data point is the average of 6 trials. All outcome measures were defined as continuous variables. Medial-lateral sway was compared between the groups using non-parametric Friedman test with a Benjamini Hochberg post-hoc correction for multiple comparisons. Anterior-posterior sway was compared between the groups using Repeated Measures ANOVA with a Tukey posthoc correction for multiple comparisons. Moreover, soft bracing resulted in improved Y-balance score and reachability in the postero-medial and posterolateral directions (FIG. 38F and Table 5). Table 5 shows data relating to composite balance score and reach distances (normalized to leg length) during Y-balance. Each individual data point is the average of 6 trials. All outcome measures were defined as continuous variables. Composite score and normalized reach distances were compared between the groups using Repeated Measures ANOVA with a Tukey posthoc correction for multiple comparisons. Inferior balance is indicative of poor neuromuscular performance in stabilizing the trunk and lower extremity joints. Large standing balance sway and low Y-balance score have been associated with unsatisfactory knee function and increased risk of ACL injury, including re-injury after surgical treatment. All together, these findings signify the potential of the proposed soft bracing approach to reduce the risk of ACL injuries by augmenting the biomechanical function of human ACL in a targeted and customizable fashion.

TABLE 4

| | | Subjects | | | | | | | **F or $\chi^2$ | ***Test of |
|---|---|---|---|---|---|---|---|---|---|---|
| | Bracing | 1 | 2 | 3 | 4 | 5 | Mean ± SD | * P-Value | Statistic | Normality |
| COP M-L Sway (mm) | No | 54 | 57 | 86 | 51 | 100 | 70 ± 22 | $P_{NR}$ = 0.034 | $\chi^2$ = 7.6 | P = 0.002 |
| | Rigid | 51 | 49 | 57 | 44 | 60 | 52 ± 6 | $P_{NS}$ = 0.040 | | |
| | Soft | 47 | 46 | 57 | 45 | 65 | 52 ± 9 | $P_{RS}$ = 0.752 | | |
| COP A-P Sway (mm) | No | 73 | 116 | 132 | 86 | 99 | 102 ± 23 | $P_{NR}$ = 0.049 | F = 4.8 | P = 0961 |
| | Rigid | 63 | 87 | 112 | 76 | 92 | 86 ± 18 | $P_{NS}$ = 0.907 | | |
| | Soft | 88 | 104 | 110 | 82 | 111 | 99 ± 13 | $P_{RS}$ = 0.093 | | |

* Adjusted P value, $P_{NR}$: No Bracing vs. Rigid Bracing, $P_{NS}$: No Bracing vs. Soft Bracing, $P_{RS}$: rigid Bracing vs. Soft Bracing.
** F-Statistic for Repeated Measures ANOVA and $\chi^2$ (Friedman Statistic) for non-parametric Friedman Test.
*** Shapiro-Wilk test, P > 0.05 indicates normal distribution.
COP: Center of Pressure.
M-L: Medial-Lateral.
A-P: Anterior-Posterior.
SD: Standard Deviation.

TABLE 5

| | Bracing | Subjects 1 | 2 | 3 | 4 | 5 | Mean ± SD | * P-Value | ** F Statistic | *** Test of Normality |
|---|---|---|---|---|---|---|---|---|---|---|
| Composite Score (unitless) | No | 97 | 115 | 97 | 90 | 107 | 101 ± 10 | $P_{NR} = 0.060$ | F = 12.1 | P = 0.126 |
| | Rigid | 99 | 119 | 97 | 95 | 115 | 105 ± 11 | $P_{NS} = 0.003$ | | |
| | Soft | 103 | 118 | 105 | 99 | 115 | 108 ± 8 | $P_{RS} = 0.134$ | | |
| Normalized Anterior Reach Distance (%) | No | 67 | 89 | 78 | 65 | 79 | 75 ± 10 | $P_{NR} = 0.939$ | F = 1.6 | P = 0.510 |
| | Rigid | 67 | 89 | 70 | 73 | 83 | 76 ± 9 | $P_{NS} = 0.275$ | | |
| | Soft | 73 | 87 | 77 | 79 | 84 | 80 ± 6 | $P_{RS} = 0.420$ | | |
| Normalized Posteromedial Reach Distance (%) | No | 105 | 133 | 107 | 103 | 120 | 114 ± 13 | $P_{NR} = 0.025$ | F = 13.4 | P = 0.108 |
| | Rigid | 110 | 138 | 110 | 108 | 129 | 119 ± 14 | $P_{NS} = 0.002$ | | |
| | Soft | 113 | 136 | 121 | 111 | 130 | 122 ± 11 | $P_{RS} = 0.240$ | | |
| Normalized Posterolateral Reach Distance (%) | No | 103 | 100 | 104 | 94 | 108 | 102 ± 5 | $P_{NR} = 0.080$ | F = 13.1 | P = 0.939 |
| | Rigid | 103 | 111 | 107 | 96 | 115 | 107 ± 7 | $P_{NS} = 0.002$ | | |
| | Soft | 107 | 114 | 114 | 99 | 123 | 111 ± 9 | $P_{RS} = 0.075$ | | |

* Adjusted P value, $P_{NR}$: No Bracing vs. Rigid Bracing, $P_{NS}$: No Bracing vs. Soft Bracing, $P_{RS}$: rigid Bracing vs. Soft Bracing.
** F-Statistic for Repeated Measures ANOVA.
*** Shapiro-Wilk test, P > 0.05 indicates normal distribution.
SD: Standard Deviation.

A soft brace can also be used in such a way as to not interfere with normal joint function and athletic performance. Previous studies have indicated that rigid prophylactic knee braces often affect athletic performance and may result in substantial discomfort (e.g. lowered sprint speed, early fatigue and increase energy expenditure. It is possible to minimize the brace interference with joint function, when is not needed (i.e. normal range of motion), to avoid negative effects on agility and athletic performance. This can be achieved by selective engagement of the external ligament only after knee rotation exceeds a predefined threshold (FIGS. 33A-33D and FIGS. 37A-37E). Additionally, a garment-based approach enables the majority of the brace weight to be close to the trunk, which may in turn lead to reduced metabolic cost. These are best evident in decreased knee range of motion (ROM) during walking and increased 3-cone drill time under rigid bracing compared to no changes under soft bracing condition (FIGS. 39A, 39B, 39C and 39D which illustrates relative effect of soft bracing on normal joint function and athletic performance, and Tables 6 and 7). This is supplemented with questionnaire-based measures of less brace-induced slow down, performance drop and fatigue reported under soft bracing compared to rigid bracing technique (Table 6). Table 6 shows data relating to subjective assessment of brace comfort and performance (brace comfort and performance questionnaire). Scores are on a scale of 1 to 10 with 1 being the lowest and 10 being the highest. Higher scores indicate better brace comfort, greater brace-induced performance drop, fatigue, slow down and interruption with normal function, more brace drift, and better joint protection. All outcome measures were defined as ordinal variables. All scores were compared between rigid and soft bracing groups using non-parametric Related Samples Wilcoxon Signed Rank test.

TABLE 6

| | Bracing | Subjects 1 | 2 | 3 | 4 | 5 | Mean ± SD | P-Value | z Statistic |
|---|---|---|---|---|---|---|---|---|---|
| Brace Drift Score (0-10) | Rigid | 5 | 8 | 1 | 4 | 5 | 4.6 ± 2.5 | 0.068 | z = 1.8 |
| | Soft | 2 | 3 | 1 | 2 | 4 | 2.4 ± 1.1 | | |
| Brace Comfort Score (0-10) | Rigid | 3 | 3 | 6 | 7 | 1 | 4.0 ± 2.5 | 0.042 | z = 2.0 |
| | Soft | 8 | 7 | 10 | 10 | 8 | 8.6 ± 1.3 | | |
| Brace Protection Score (0-10) | Rigid | 4 | 4 | 10 | 3 | 4 | 5.0 ± 2.8 | 0.786 | z = 0.3 |
| | Soft | 3 | 5 | 4 | 6 | 6 | 4.8 ± 1.3 | | |
| Brace Normal Function Interruption Score (0-10) | Rigid | 7 | 8 | 1 | 4 | 3 | 4.6 ± 2.9 | 0.068 | z = 1.8 |
| | Soft | 3 | 3 | 1 | 1 | 2 | 2.0 ± 1.0 | | |
| Brace Induced Fatigue Score (0-10) | Rigid | 6 | 7 | 1 | 2 | 3 | 3.8 ± 2.6 | 0.66 | z = 1.8 |
| | Soft | 3 | 2 | 1 | 1 | 1 | 2.0 ± 1.7 | | |
| Brace-Induced Performance Drop Score (0-10) | Rigid | 7 | 8 | 3 | 2 | 3 | 4.6 ± 2.7 | 0.042 | z = 2.0 |
| | Soft | 2 | 2 | 1 | 1 | 2 | 1.8 ± 0.8 | | |
| Brace-Induced Slow Down Score (0-10) | Rigid | 4 | 7 | 7 | 4 | 3 | 5.0 ± 1.9 | 0.042 | z = 2.0 |
| | Soft | 2 | 2 | 1 | 1 | 1 | 1.4 ± 0.6 | | |
| Inclined to take the brace off during game | Rigid | Y | Y | Y | N | Y | — | — | |
| | Soft | N | N | N | N | N | — | | |
| Brace Preference | | Soft | Soft | Soft | Rigid | Soft | — | — | — |

SD: Standard Deviation.
Y: Yes.
N: No.

Figure 35A:
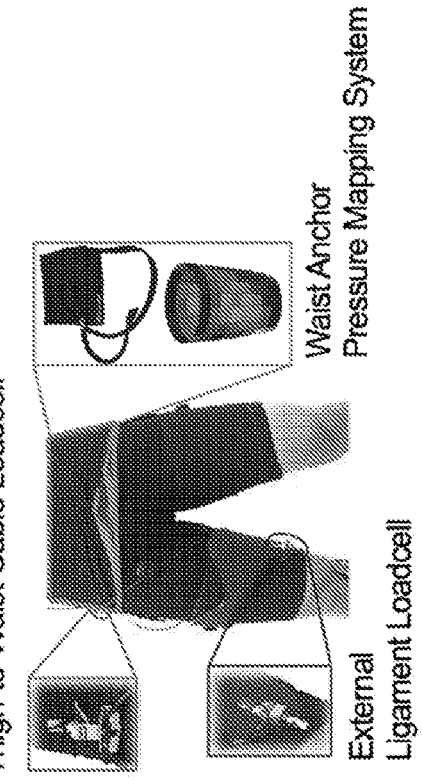
FIGS. 35A, 35B, and 35C illustrate exemplary force distribution across a plurality of anchoring components of an embodiment of a soft joint brace.
Figure 35B:
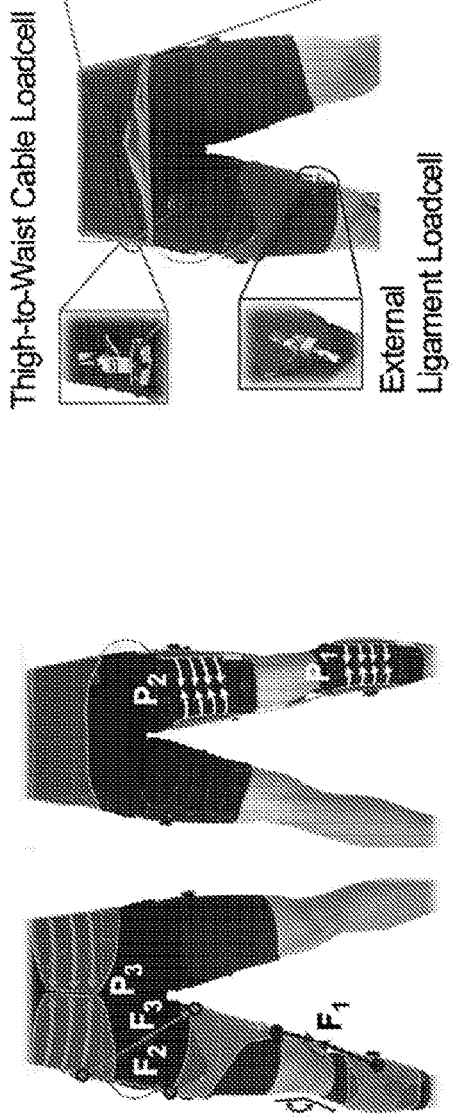
Figure 35C:
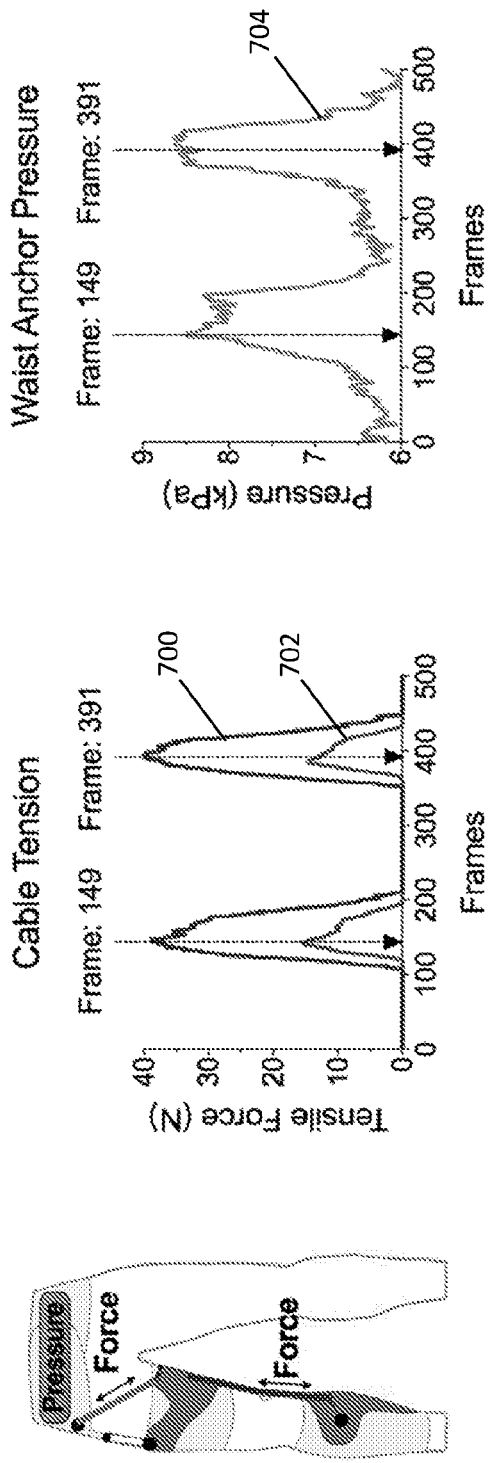

It can also be important to keeping the brace from slipping down to a position in which it loses its protective function. In the soft bracing approach, in some embodiments it is possible, with the functional apparel that anchors to the body by means of friction, through the use of geometrical landmarks and compression, and distribution of the loads across multiple segments spanning the whole leg (FIGS. 35A-35C). The anchoring components can conform to the complex geometry of the upper and lower leg and provide a secure and comfortable brace-to-body interface. In comparison to rigid bracing, a soft bracing technique can better accommodate the dynamic changes in thigh volume during quadriceps contraction and shows less increase in pressure across the thigh-brace interface, as a result of quadriceps contraction (FIGS. 36A-36D). This improved load distribution and anchoring may have contributed to the observed lower downward drift (FIG. 39D illustrates a maximum downward brace drift (* p=0.029). Mean±SD (n=5/group)) and better subjective brace comfort score compared to the rigid bracing condition (Tables 8 and 9).

A bio-inspired soft brace can be used to deliver customizable and targeted protection to the joint without sacrificing performance.

Materials and Methods

Mechanical Testing

Figure 34A:
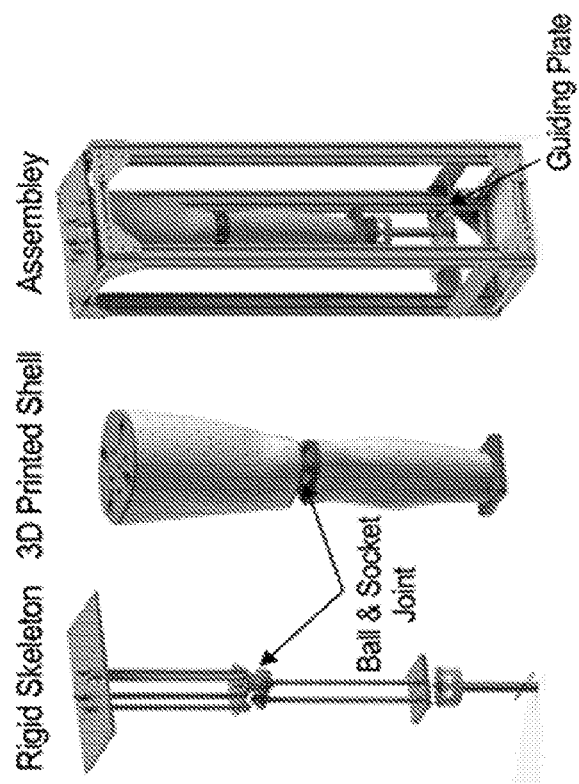

A mechanical test rig was designed to gain qualitative and quantitative understanding of how different external ligament configurations affect knee rotation. The rig was designed such that the thigh would be mechanically fixed and the calf manipulated by the user to simulate the rotation of the knee in different directions. An overview of the test setup is shown in FIGS. 34A, 34B, 34C and 34D, which illustrates a mechanical assessment of a soft bracing approach to offer targeted and adjustable protection against ACL injuries. FIG. 34A illustrates a mechanical test frame and its components used to identify the proper configuration of external ligament module (EL) to protect the knee joint against excessive abduction rotation without disrupting knee flexion-extension (LC: Loadcell, IMU: Inertial Measurement Unit). At the center of the test frame was a rigid skeleton comprised of multiple steel rods and aluminum plates with a ball-and-socket joint simulating the knee joint. An aluminum hex-rod handle was attached at the very bottom of the skeletal system to allow user to rotate the leg in different directions. Encapsulating the skeleton was an anatomically accurate, 3D-printed ABS plastic shell resembling the lower leg anatomy of a $50^{th}$ percentile male. The shell had a number of through-holes across the whole surface, which served as anchor points for the external ligament module. A ten-axis inertial measurement unit (IMU, VN-100 Rugged, VectorNav Technologies, Dallas, TX, USA) was used to measure calf rotation relative to the thigh in all three planes with a resolution of 0.5°. A six-axis loadcell (ATI Gamma US-15-50, ATI Industrial Automation, Apex, NC, USA) was also used to quantify applied torques with a resolution of 0.1 Nm. The IMU was secured to the posterior distal aspect of the calf and the loadcell was fixed to the bottom part of the rigid skeleton right above the load applying handle. The IMU and the loadcell data were synchronized and captured at 1 kHz using LabVIEW (National Instruments, Woburn, MA, USA). Prior to each test, the rig was calibrated to account for the resistance of the ball-and-socket joint and weight of the mechanical leg. A laser cut Plexiglas guiding plate was used to consistently hold the leg in neutral position during calibration. Eurler angles were used to calculate knee rotations from IMU coordinates.

Using this setup, multiple configurations of the external ligament were tested to identify the optimum location of the external ligament to resist knee abduction without interfering with knee flexion. FIG. 34B illustrates design parameters tested using the mechanical test frame shown in FIG. 34A to optimize external ligament configuration. Briefly, the external ligament was fixed to the leg in a specific orientation and location, and then rotated the leg in all three planes. The real time graphs of applied torque vs. knee rotation were used to characterize the effect of external ligament in restricting the knee range of rotation. The orientation and/or the location of the external ligament can be changed and the experiment can be repeated. This set of assessments revealed that vertically oriented ligament across the medial aspect of the knee can provide resistance against knee abduction whereas a more horizontally inclined ligament can resist knee internal rotation. As expected, it was further demonstrated that the external ligament should pass through the approximate center of rotation of the joint to avoid unwanted resistance to knee flexion (occur if the ligament was placed anteriorly) or decreased resistance against knee abduction as knee flexes (occur if the ligament was placed posteriorly). In addition, by changing the slack length of the vertically oriented external ligament, the abduction angle can be adjusted beyond which the ligament begins to restrict knee abduction (adjustable protection; FIGS. 34A-34D). FIG. 34C illustrates a non-linear behavior achieved under optimized configuration of external ligament. Data from the same configuration with two different protective thresholds are shown (solid black line: threshold of 2.6°, dotted black line: threshold of 5.2°). External ligament offered minimal resistance to knee abduction below the protection threshold followed by increased resistance (shown by sharp increases in applied torques to further rotate the knee joint) to additional knee abduction beyond the set threshold. FIG. 34D illustrates that the external ligament remained unloaded and did not resist knee flexion (no changes in applied flexion torque required to flex the knee).

Soft Brace Design and Fabrication

In some embodiments, a soft brace has a unilateral design comprised of functional apparel that securely, yet comfortably, anchors to the body at the waist, thigh and calf (FIG. 33A). The anchoring components are lined with non-slip, breathable material to reduce brace drift relative to the body. These anchors are tightened and secured to the geometrical landmarks of the body by means of Velcro straps and adjustable compression controlled by a network of Dyneema cables and ratchet length adjusting system (BOA Technology Inc., Denver, CO, USA). The thigh and calf anchors are connected by the external ligament module (a high tensile strength cable) in the medial aspect of the leg. Attaching the waist and thigh anchors are a series of Dyneema force distribution cables routed through the lateral and front to back of the proximal thigh. This network of force distribution cables are designed to dissipate the external ligament tension, generated during high-risk maneuvers, across the waist, thigh and calf anchors. All the cables are secured to the anchoring components using BOA ratchet length adjusting components (FIG. 33D). Flexible thermoplastic plates are incorporated in the thigh and calf anchors to provide a stable surface to secure the BOA ratchet dials. Each plate was cut to the shape and heat-formed around the thigh or calf to improve the brace-body interface. A 3D printed guide was secured to the medial aspect of the calf anchor to keep the external ligament in the approximate knee center of rotation (FIG. 33D).

Clinical Evaluations in Human Subjects

Participants and Inclusion/Exclusion Criteria

Five healthy male subjects (26.7±4.8 years old) were tested under a range of functional, biomechanical and performance related tests. Subjects were included if they were: A) 18-50 years old, B) in good general health condition (i.e. no chronic disease), C) being comfortable performing athletic activities to a point at which they become fatigued, and D) participating in any sports, fitness, or recreational (leisure) activities regularly (for at least 3 hours per week) during which physical exertion is moderate, hard or very hard (assessed using a physical activity questionnaire; Supplementary Materials). Subjects were excluded if they: A) had a history of neuromuscular, neurological, visual, vestibular, balance, or gait disorders/pathology, B) had a history of major injuries or pathologies (such as a ligament tear/sprain, arthritis) to either ankle, knee, or hip, C) had a systemic infection at the time of the study, and D) regularly use tobacco or recreational drugs. Subjects were screened by an IRB approved clinical research coordinator. Enrolled subjects provided written informed consent before their participation and after the nature and possible consequences of the studies were explained. Baseline characteristics of all subjects are presented in Table 7.

TABLE 7

| | Age (years) | Weight (Kg) | Height (cm) | Leg Length (cm) | Circumference (cm) Thigh | Circumference (cm) Calf | Rigid Brace Size |
|---|---|---|---|---|---|---|---|
| Subject 1 | 25 | 77 | 177 | 89 | 52 | 37 | L |
| Subject 2 | 29 | 75 | 171 | 87 | 52 | 38 | XL |
| Subject 3 | 27 | 73 | 180 | 98 | 53 | 41 | L |
| Subject 4 | 27 | 86 | 184 | 95 | 55 | 41 | XL |
| Subject 5 | 28 | 83 | 194 | 91 | 42 | 40 | L |

L: Large.
XL: X-Large.

Bracing

All enrolled subjects were tested by a single functional soft brace prototype, designed to fit the right knee of a male subject with a thigh circumference of 43-53 cm and a calf circumference of 35-40 cm (10th to 75th percentile of males 20 years old and above). Owing to its multi-body design, the proposed soft brace can accommodate a large range of heights and leg lengths. For rigid bracing condition, a commonly used prophylactic knee brace for prevention of knee ligamentous injuries (i.e. ACL) was used (DonJoy Armor ACL FourcePoint, DJO Global, Vista, CA, USA). A DonJoy representative measured each of the study participants with a Custom Contour Measuring Instrument (CCMI Mark III) and determined that a large brace (thigh, 21-23.5 inches; calf, 16-18 inches) would best accommodate all the subjects. However, two of the subjects (subjects 2 and 4) preferred an x-large Armor brace due to poor fit and discomfort. An experienced functional apparel designer (R.G.) donned the braces on participants. Upon donning the soft brace, the external ligament was pre-tensioned to 5 N prior to testing to ensure consistency across all the subjects.

Assessment of Soft Brace Function

In order to assess overall functionality of the developed prototype, we collected data for knee kinematics and tension forces across the external ligament in all subjects during valgus collapse and open chain knee flexion maneuvers. External ligament tension was measured by a uniaxial loadcell (LSB 200, FUTEK Advanced Sensor Technology, Irvine, CA, USA) incorporated across the ligament attachment to the thigh anchor only for experimental evaluation purposes of this study. Knee kinematics was quantified using reflective markers and infrared motion capture system (Vicon, Oxford Metrics, Oxford, UK). For valgus collapse, subjects were instructed to stand with their feet internally rotated and shoulder width apart from each other. They were then asked to try to have their knees bent towards each other, as close as possible, while keeping their knees at minimum flexion. This is the most common lower leg posture reported during non-contact ACL injuries. Subjects were allowed to practice until they felt comfortable performing this task. Subjects were also asked to perform 3 cycles of open chain knee flexion, self-selected range of rotation, with their right braced knee. Finally, each subject repeated another 3 cycles of valgus collapse after doubling the external ligament pre-tension level. Knee rotation versus external ligament tension data for the second cycle of each task were used to assess the brace efficacy in restricting excessive knee abduction without interfering with knee flexion (FIGS. 37A-37E and Table 3).

Assessment of Force Distribution Across Soft Brace Components

Figure 36B:
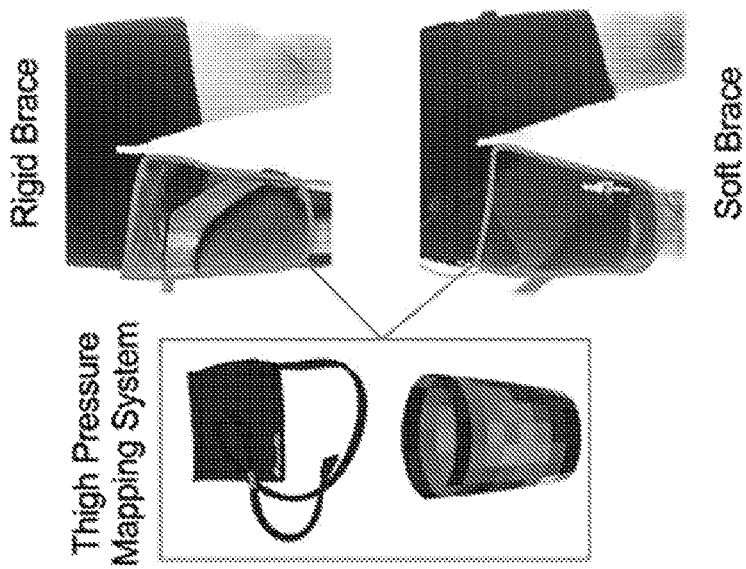
FIGS. 36A, 36B, 36C, and 36D illustrate exemplary brace interference with muscle contraction.
Figure 36A:
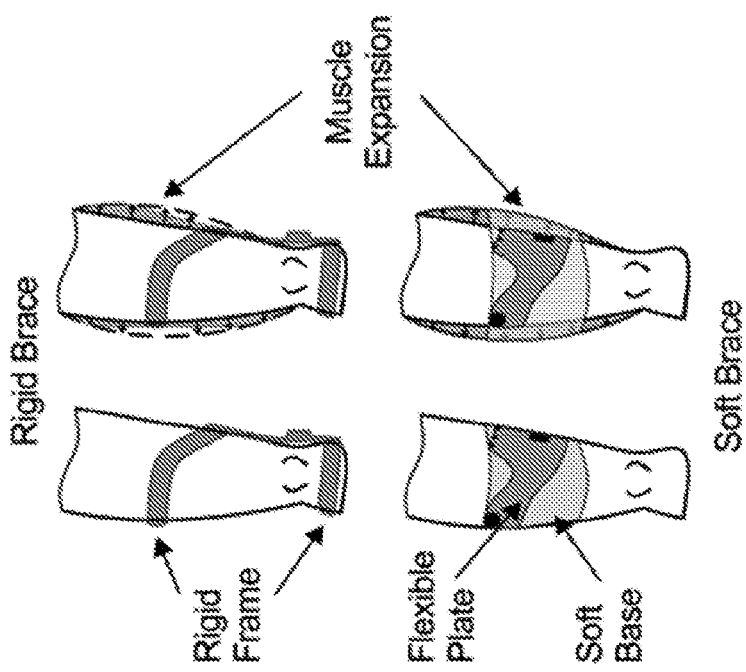
Figures 36C, 36D:
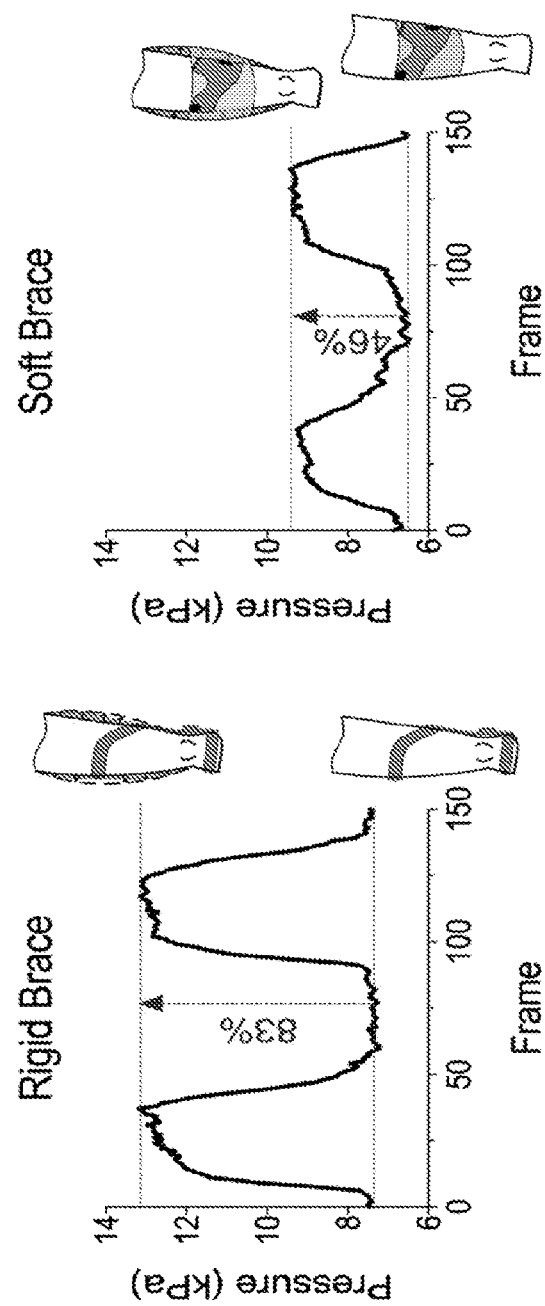

To illustrate the distribution of forces across different components of the developed prototype, a single subject was asked to perform multiple cycles of valgus collapse maneuver to increase the external ligament tension (FIGS. 35A, 35B and 36C). FIGS. 35A, 35B and 35C illustrate force distribution across multiple anchoring components of the soft brace. FIG. 35A illustrates that a tension generated along the external ligament (F1) dissipates across the conformable calf (P1), thigh (P2) and waist (P3) anchors through a network of force distribution cables connecting these anchors (i.e. F2 and F3). FIG. 35B shows measurements of tension across the external ligament and the force distribution cable connecting the thigh anchor to the waist anchor using two uniaxial loadcells incorporated in the cable attachments on thigh and waist anchors, respectively. Measurements of the average pressure under the waist anchor using a thin pressure mapping sensor placed around the waist under the anchor. Tensile forces were measured across the external ligament and along thigh-to-waist force distribution cable using two uniaxial LSB 200 loadcells, incorporated in the cable attachments on thigh and waist anchors, respectively (FIG. 35B). In addition, a thin flexible pressure sensor (SensorEdge Inc., Parsippany, NJ, USA) was used to measure pressure changes under the waist anchor in reaction to changes in external ligament tension under valgus loading (FIG. 35B). As shown in FIG. 35C, simultaneous increases in tensile forces were observed across the external ligament and the thigh-to-waist force distribution cable as well as in waist anchor pressure under valgus loading. This shows that external ligament, protecting the knee, engages every component of the garment and transfers forces all the way to the waist. FIG. 35C illustrates changes in external ligament tension (line 700), thigh-to-waist cable tension (line 702) and waist anchor pressure (line 704) during two cycles of knee valgus collapse performed by one subject.

Assessment of Brace Interference with Quadriceps Contraction

To evaluate how developed soft brace responds to change in thigh shape sue to quadriceps contraction, a single subject performed multiple cycles of voluntary quadriceps contraction under soft and rigid bracing conditions. A SensorEdge thin flexible pressure sensor was wrapped around the thigh under the brace to quantify the pressure changes across brace-thigh interface. As shown in FIGS. 36A, 36B, 36C and 36D, quadriceps contraction resulted in 83% increase in average thigh-rigid brace interface pressure, which was almost double the 46% increases observed under soft bracing condition. This suggests that the proposed soft bracing approach offer a more compatible interface with body, which may in turn lead to more effective anchoring with minimized drift and better comfort. FIGS. 36A, 36B, 36C and 36D illustrate brace interference with quadriceps contraction. FIG. 36A illustrates expansion of the quadriceps muscles during activation (contraction). FIG. 36B illustrates measurements of the average pressure at the interface of the thigh and the brace (rigid and soft) using a thin flexible pressure mapping sensor placed around the thigh under the thigh anchor. FIG. 36C and FIG. 36D illustrate changes in average thigh pressure during two cycles of maximum voluntary quadriceps contraction performed by one subject under rigid (FIG. 36C) and soft (FIG. 36D) bracing conditions. Under rigid bracing, quadriceps contraction resulted in 83% increase in average thigh pressure, which was almost double the 46% increases observed under soft bracing condition.

Assessment of Brace Efficacy and Transparency

Figures 40A, 40B:
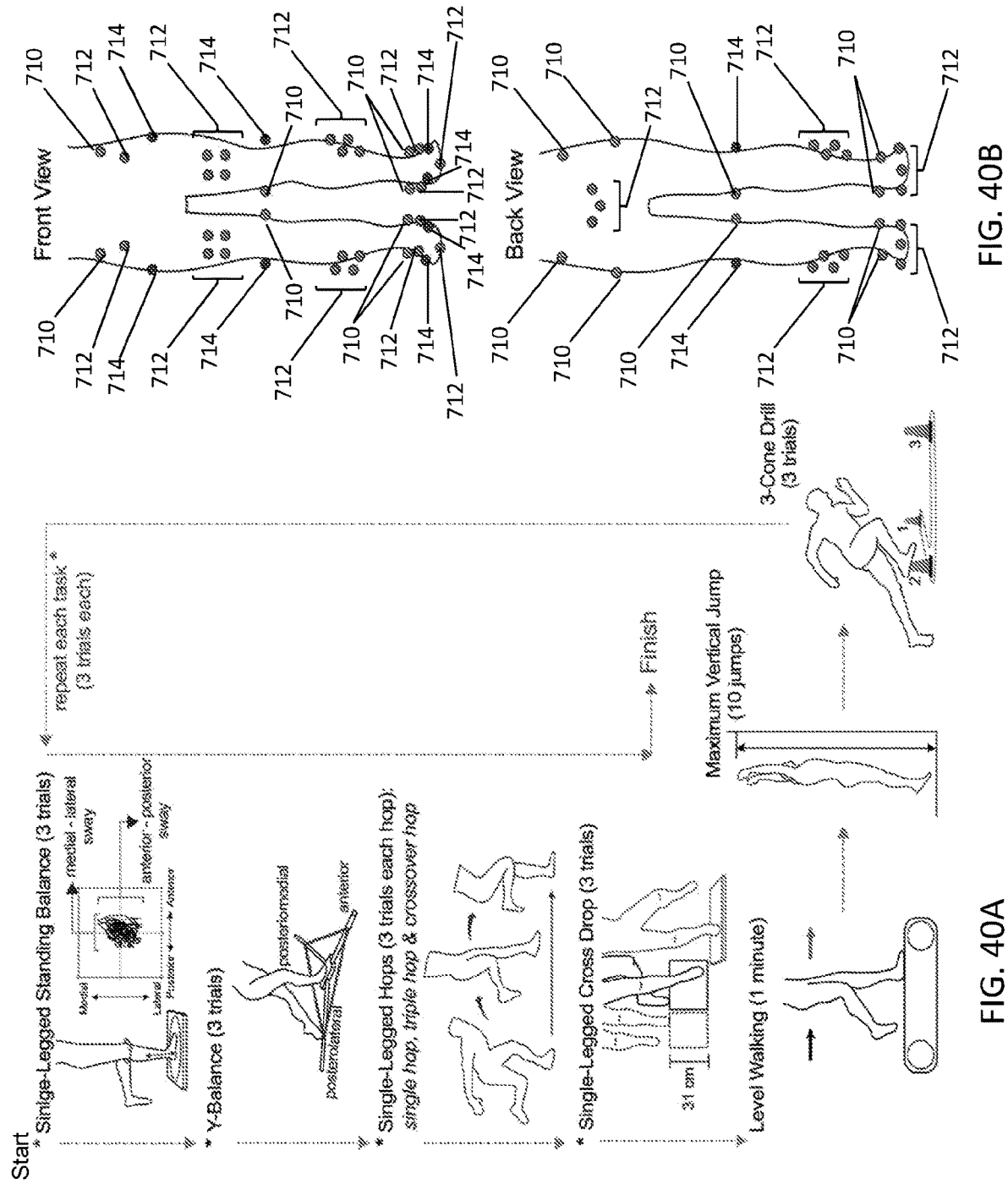
FIG. 40A and FIG. 40B illustrate clinical evaluation of bracing effects on knee biomechanics.

To evaluate the performance of the proposed soft bracing in comparison to commonly used rigid prophylactic knee bracing technique, we tested each subject under a wide range of biomechanical and functional tests relevant to knee function and ACL injury risk. We also, investigated the brace fit and drift as well as its effect on athletic performance and agility. Each subject was tested under three bracing conditions: 1) no bracing, 2) rigid bracing and 3) soft bracing following the same protocol (FIG. 40A and FIG. 40B). Subjects were only tested under one bracing condition in each session and the average time between sessions for each subject was nine days. The study was not blinded or randomized. Prior to each test, subjects were shown how to conduct each task by a member of the research team. Subjects were allowed to practice until they fill comfortable preforming each task. FIG. 40A and FIG. 40B illustrate an exemplary clinical evaluation of bracing effect on knee biomechanics and function as well as overall performance in human subjects. FIG. 40A illustrates an experimental design for each bracing condition (no bracing, rigid bracing and soft bracing). An * indicates tasks that were repeated for another 3 trials after the 3-cone drill. Dotted arrows show the testing sequence from the beginning of each session (Start) to the end (Finish). Subjects performed an addition single-legged cross drop with over-tensioned external ligament at the end of the soft bracing session. FIG. 40B illustrates a configuration of the reflective markers used to quantify lower extremity kinematics. Markers 710 were used to define body segments. Markers 712 were used to track segmental kinematics. Markers 714 were used in both segment definition and tracking segmental kinematics.

Primary endpoints related to brace efficacy in protecting the knee joint were peak knee abduction during cross drop, COP medial-lateral sway during standing balance and Y-balance composite score. Primary endpoints related to brace transparency to knee function and athletic performance were peak knee flexion during cross drop, knee range of rotation during level walking, normalize hop distance, 3-cone drill time and maximum vertical jump height. Peak knee internal rotation during cross drop, brace downward drift along with questionnaire-based subjective assessment of brace comfort and performance were also evaluated as secondary endpoints. All endpoints were selected prior to data collection. All subjects completed all the tests within each session for all three conditions. One of the subjects (subject 2) could not finish the rigid bracing session due to unbearable discomfort related to poor brace fit. His rigid bracing session was repeated in another day with a larger brace. Data from his unfinished session was not used in the final analysis. The study was approved by the Harvard Longwood Medical Area Institutional Review Board, and all methods were carried out in accordance with the approved study protocol. Subjects completed multiple trials or cycles of the following tasks in a motion capture lab during each bracing session (FIG. 40A and FIG. 40B).

Single-Legged Standing Balance:

Subjects were asked to maintain balance on their right leg while standing on a force plate (OR6-6, AMTI, Watertown, MA, USA) with closed eyes for as long as they could, up to 30 seconds. Each subject performed six trials under each bracing condition. Average trial duration was 25±7 s. Force plate COP trajectory data was used to extract the maximum displacement in anterior, posterior, medial and lateral directions. COP sway was defined as distanced between the respective maximums in anterior-posterior and medial-lateral directions (FIGS. 38A-38F and Table 4).

Y-Balance:

Subjects were asked to stand on both legs at the center of a Y shape, taped to the floor (the center was defined as the intersection of anterior, posteromedial and posterolateral lines; FIGS. 40A-40B). While maintain balance on their right leg, subjects were asked to use their left leg to reach the maximum anterior distance possible without putting any weight on their left leg and then return to double-legged standing position. Subjects repeated the same task along posteromedial and posterolateral directions. Each subject performed 6 trials for each direction under each bracing condition. Reach distance in each direction was measured using a standard tape measure. The composite score for each trial was calculated using following equation. The Y-balance composite score and reach distances are presented in FIGS. 38A-38F and Table 5.

$$\text{Composite Score} = \frac{\text{Sum of reach distances in all three directions} \times 100}{\text{Leg length} \times 3}$$

Single-Legged Hop:

Subjects performed a single hop, triple consecutive hops, and triple consecutive hops each time crossing a straight line marked on the floor to reach the maximum forward distance they could using their right leg. These are the tests routinely used in clinics and laboratories to assess knee performance related to ACL function and injury risk. Each subject performed 6 trials of each hop under each bracing condition. Hop distance was measured using a standard tape measure and then normalized to subjects' leg length (Table 8). Table 8 shows single-legged hop distances normalized to leg length. Each individual data point is the average of 6 trials. All outcome measures were defined as continuous variables. Normalized single hop distance was compared between the groups using Repeated Measures ANOVA with a Tukey posthoc correction for multiple comparisons. Normalized triple and crossover hops were compared between the groups using non-parametric Friedman test with a Benjamini Hochberg posthoc correction for multiple comparisons.

TABLE 8

| | Bracing | \multicolumn{5}{c}{Subjects} | Mean ± SD | * P-Value | ** F or $\chi^2$ Statistic | *** Test of Normality |
|---|---|---|---|---|---|---|---|---|---|---|
| | | 1 | 2 | 3 | 4 | 5 | | | | |
| Normalized Single Hop Distance (%) | No | 174 | 216 | 220 | 137 | 256 | 201 ± 46 | 243 | F = 2.1 | P = 0.431 |
| | Rigid | 199 | 216 | 217 | 150 | 269 | 210 ± 43 | $P_{NS}$ = 0.244 | | |
| | Soft | 197 | 230 | 228 | 149 | 247 | 210 ± 39 | $P_{RS}$ > 0.999 | | |
| Normalized Triple Hop Distance (%) | No | 625 | 658 | 637 | 404 | 577 | 580 ± 103 | $P_{NR}$ = 0.514 | $\chi^2$ = 1.2 | P = 0.029 |
| | Rigid | 593 | 728 | 638 | 437 | 731 | 625 ± 121 | $P_{NS}$ = 0.514 | | |
| | Soft | 620 | 744 | 665 | 390 | 722 | 628 ± 141 | $P_{RS}$ > 0.999 | | |
| Normalized Crossover Hop Distance (%) | No | 508 | 635 | 582 | 331 | 627 | 536 ± 126 | $P_{NR}$ > 0.999 | $\chi^2$ = 1.2 | P = 0.049 |
| | Rigid | 491 | 708 | 561 | 325 | 676 | 552 ± 154 | $P_{NS}$ = 0.514 | | |
| | Soft | 531 | 695 | 627 | 277 | 679 | 562 ± 172 | $P_{RS}$ = 0.514 | | |

* Adjusted P value, $P_{NR}$: No Bracing vs. Rigid Bracing, $P_{NS}$: No Bracing vs. Soft Bracing, $P_{RS}$: rigid Bracing vs. Soft Bracing.
** F-Statistic for Repeated Measures ANOVA and $\chi^2$ (Friedman Statistic) for non-parametric Friedman Test.
*** Shapiro-Wilk test, P > 0.05 indicates normal distribution.
SD: Standard Deviation.

Single-Legged Cross Drop:

Subjects were instructed to stand on their left leg on top of a 31 cm high step and then hop forward and medially off the box and land on their right foot. This is a relevant task to study the biomechanics of ACL injury in the laboratory setting. Each subject performed 6 cross drops under each bracing condition (FIGS. 40A-40B). Subjects performed an additional cross drop with over-tensioned external ligament under soft bracing condition. Peak knee rotations, during the stance phase of landing, were calculated for each trial (FIGS. 38A-38F and Table 2).

Level Walking:

Subjects were asked to walk for 1 minute on an instrumented treadmill (Bertec, Columbus, OH, USA) at a self-selected speed. This was done to assess the effect of bracing on knee function during normal (low risk) activities, where no joint protection is required. Average walking speed was 1.3±0.1 ms 1. Knee range of motion in each anatomic plane was calculated as maximum-minimum rotation (e.g. flexion-extension) for 20 complete gait cycles under each bracing condition (FIG. 39A and FIG. 39B which illustrates range of knee abduction (* p<0.04) and internal rotation (* p=0.034) during level walking, and Table 9). Table 9 shows data relating to knee range of motion during level walking. Each individual data point is the average of 20 gait cycles. All outcome measures were defined as continuous variables. Knee flexion and abduction range of motion were compared between the groups using Repeated Measures ANOVA with a Tukey posthoc correction for multiple comparisons. Knee internal rotation range of motion was compared between the groups using non-parametric Friedman test with a Benjamini Hochberg posthoc correction for multiple comparisons.

TABLE 9

| | Bracing | \multicolumn{5}{c}{Subjects} | Mean ± SD | * P-Value | ** F or $\chi^2$ Statistic | *** Test of Normality |
|---|---|---|---|---|---|---|---|---|---|---|
| | | 1 | 2 | 3 | 4 | 5 | | | | |
| Knee Flexion ROM (degrees) | No | 68.5 | 65.3 | 63.3 | 71.5 | 59.6 | 65.6 ± 4.6 | $P_{NR}$ = 0.133 | F = 3.3 | P = 0.722 |
| | Rigid | 199 | 216 | 217 | 150 | 269 | 64.0 ± 2.7 | $P_{NS}$ = 0.117 | | |
| | Soft | 197 | 230 | 228 | 149 | 247 | 63.9 ± 4.2 | $P_{RS}$ = 0.995 | | |
| Knee Abduction ROM (degrees) | No | 9.8 | 9.1 | 9.9 | 9.7 | 9.6 | 9.6 ± 0.3 | $P_{NR}$ = 0.033 | F = 9.7 | P = 0.688 |
| | Rigid | 7.0 | 5.1 | 5.8 | 7.4 | 6.7 | 6.4 ± 0.9 | $P_{NS}$ = 0.551 | | |
| | Soft | 4.6 | 13.8 | 10.6 | 11.0 | 10.5 | 10.7 ± 2.2 | $P_{RS}$ = 0.007 | | |
| Knee Internal Rotation ROM (degrees) | No | 15.9 | 16.9 | 28.5 | 22.9 | 14.6 | 19.8 ± 5.8 | $P_{NR}$ = 0.034 | $\chi^2$ = 6.4 | P = 0.029 |
| | Rigid | 12.4 | 13.1 | 18.4 | 17.2 | 13.3 | 14.9 ± 2.7 | $P_{NS}$ = 0.206 | | |
| | Soft | 15.3 | 14.6 | 18.3 | 19.3 | 16.3 | 16.8 ± 2.0 | $P_{RS}$ = 0.206 | | |

* Adjusted P value, $P_{NR}$: No Bracing vs. Rigid Bracing, $P_{NS}$: No Bracing vs. Soft Bracing, $P_{RS}$: rigid Bracing vs. Soft Bracing.
** F-Statistic for Repeated Measures ANOVA and $\chi^2$ (Friedman Statistic) for non-parametric Friedman Test.
*** Shapiro-Wilk test, P > 0.05 indicates normal distribution.
ROM: Range of Motion.
SD: Standard Deviation.

Maximum Vertical Jump:

Subjects were asked to perform 10 consecutive vertical jumps, against a wall, aimed to reach the maximum height possible (FIGS. 40A-40B). Subjects marked their maximum height on the wall using a marker. Maximum jump height was measured using a standard tape measure and then normalized to subjects' height (Table 10). Table 10 shows data relating to maximum vertical jump height (normalized to height) and 3-cone drill time. Each individual data point is the average of 6 trials. All outcome measures were defined as continuous variables. Normalized height and drill time were compared between the groups using Repeated Measures ANOVA with a Tukey posthoc correction for multiple comparisons.

TABLE 10

| | Bracing | Subjects 1 | 2 | 3 | 4 | 5 | Mean ± SD | * P-Value | ** F or $\chi^2$ Statistic | *** Test of Normality |
|---|---|---|---|---|---|---|---|---|---|---|
| Normalized Maximum Vertical Jump Height (%) | No | 150 | 152 | 153 | 143 | 150 | 150 ± 4 | $P_{NR}$ = 0.959 | F = 1.1 | P = 0.416 |
| | Rigid | 148 | 148 | 153 | 145 | 144 | 149 ± 3 | $P_{NS}$ = 0.534 | | |
| | Soft | 150 | 152 | 157 | 144 | 152 | 151 ± 5 | $P_{RS}$ = 0.391 | | |
| 3-cone Drill Time (ms) | No | 10843 | 10247 | 9027 | 10720 | 9307 | 10029 ± 824 | $P_{NS}$ = 0.023 | F = 8.7 | P = 0.613 |
| | Rigid | 10950 | 11007 | 10267 | 11117 | 9987 | 10665 ± 50 | $P_{NS}$ = 0.911 | | |
| | Soft | 10427 | 9833 | 9450 | 10280 | 9763 | 9951 ± 398 | $P_{RS}$ = 0.013 | | |

* Adjusted P value, $P_{NR}$: No Bracing vs. Rigid Bracing, $P_{NS}$: No Bracing vs. Soft Bracing, $P_{RS}$: rigid Bracing vs. Soft Bracing.
** F-Statistic for Repeated Measures ANOVA.
*** Shapiro-Wilk test, P > 0.05 indicates normal distribution.
ms: Milliseconds.
SD: Standard Deviation.

3-Cone Drill:

Subjects ran across three cones, 5 yards apart from each other in an L-shaped configuration (FIGS. 40A-40B), as fast as possible and the time to complete the drill was measured. Subjects started from the first cone and ran to the second cone and back to first cone. They then ran to the third cone by passing around the second cone (#2) and back to the first cone (FIGS. 40A-40B). Each subject completed 3 drills per bracing condition. Drill time was quantified using a digital chronometer (FIG. 39C, which illustrates 3-cone drill time (* p<0.03), and Table 10).

Assessment of Brace Drift:

To assess the brace drift, corresponding marks were made directly on the participants' skin and on the brace both proximally and distally right after donning the brace and prior to testing. Throughout the session, measurements were taken to document brace drift relative to the initial location. The measurements were done by an experienced functional apparel designer (R.G) using standard tape measure (FIGS. 39A-39D and Table 11). Table 11 shows data relating to brace downward drift and donning time. All outcome measures were defined as continuous variables. Brace drift was compared between groups using a Composite score and normalized reach distances were compared between the rigid and soft bracing groups using Paired-Sample t-test. Brace donning time was compared between the rigid and soft bracing groups using non-parametric Related Samples Wilcoxon Signed Rank test.

TABLE 11

| | Bracing | Subjects 1 | 2 | 3 | 4 | 5 | Mean ± SD | * P-Value | ** F or $\chi^2$ Statistic | *** Test of Normality |
|---|---|---|---|---|---|---|---|---|---|---|
| Brace Drift (mm) | Rigid | 15 | 20 | 15 | 30 | 10 | 18 ± 8 | 0.029 | t = 3.4 | P = 0.056 |
| | Soft | 10 | 10 | 8 | 10 | 5 | 9 ± 2 | | | |
| Donning Time (minutes) | Rigid | 3 | 3 | 5 | 5 | 2 | 3.6 ± 1.3 | 0.042 | z = 2.0 | P = 0.015 |
| | Soft | 10 | 10 | 9 | 10 | 10 | 9.8 ± 0.5 | | | |

* t-Statistic for Paired-Sample t-Test and z-Statistic for Related Samples Wilcoxon Signed Rank Test.
** Shapiro-Wilk test, P > 0.05 indicates normal distribution.
SD: Standard Deviation.

Subjective Assessment of Brace Comfort and Performance:

Upon completion of all tests during each rigid or soft bracing sessions conditions, the subjects were asked to fill a questionnaire focused on subject's perception of brace performance and effect on athletic function and fatigue. Questionnaires were solely filled by the subjects in a private room without any input from the examiners and investigators to minimize potential bias. Out of 5, 4 subjects expressed their willingness to take the rigid brace off if the game was on the line, whereas only 1 subject expressed the same filling under the soft bracing condition (this subject was also willing to take off the rigid brace during the game). 4 out 5 subjects preferred soft bracing over rigid bracing during athletic activities (Table 6).

Data Acquisition and Treatment

Kinematics data were collected using a 10-camera 3D Vicon motion capture system along with 53 reflective markers (FIGS. 40A-40B) at 120 Hz and filtered using a zero-lag, 4th order, low-pass, Butterworth filter with cut-off frequency of 6 Hz. Loadcells and force plate data were acquired at 2160 Hz and filtered using a zero-lag, 4th order, low-pass, Butterworth filter with cut-off frequency of 15 Hz. Waist and thigh pressure data were collected at 400 Hz. Data from all the sensors and cameras were synchronized. The analyses and filtering were performed using Visual 3D (C-Motion, Rockville, MD, USA) and custom written macros in Matlab (Mathworks, Natick, MA, USA).

Statistical Analysis

Data from all trials or cycles per bracing condition were averaged for each subject and these values were used for final analysis (Tables 2-9 and 11). Data normality was assessed using histograms and confirmed by Shapiro-Wilk's test in SPSS (IBM Corp., Armink, NY, USA). Normally distributed data were compared using Paired-Sample t-test or Repeated Measures Analysis of Variance (ANOVA) with a Tukey posthoc correction for multiple comparisons (Prism, GraphPad Software Inc., La Jolla, CA, USA). Not normally distributed data and ordinal outcomes were compared between the groups using non-parametric Related Samples Wilcoxon Signed Rank test (SPSS) or non-parametric Friedman test with a Benjamini Hochberg posthoc correction for multiple comparisons (Prism). P values are two-sided and the statistical significance was assessed at alpha=0.05 for all the comparisons.

All patents, patent applications, and published references cited herein are hereby incorporated by reference in their entirety. It will be appreciated that several of the above-disclosed and other features and functions, or alternatives thereof, may be desirably combined into many other different systems or application. Various alternatives, modifications, variations, or improvements therein may be subsequently made by those skilled in the art.

The invention claimed is:

1. A soft brace comprising:
one or more tensile elements configured to limit excessive movement of a knee joint;
  wherein a placement of the one or more tensile elements and a tension of each of the one or more tensile elements provides resistance against excessive movement of the knee joint,
  wherein at least one of the one or more tensile elements is configured to extend from a position proximal the knee joint to a position distal the knee joint around at least one of a medial aspect or a lateral aspect of the knee joint to provide resistance against knee rotation in at least one of a frontal plane or a transverse plane;
a plurality of soft tissue anchors configured to be positioned on a body around the knee joint, the one or more anchors being configured to anchor one or more of the one or more tensile elements to the body to provide force distribution relative to the knee joint; and
at least one anchor support cable directly connected to:
  at least two soft tissue anchors of the plurality of soft tissue anchors, and
  the at least one of the one or more tensile elements,
  wherein the at least one anchor support cable is configured to restrict the at least one of the one or more tensile elements from deviating from an approximate center of rotation of the knee joint;
wherein, as configured to limit excessive movement of the knee joint, the one or more tensile elements do not generate tension during normal movement of the knee joint.

2. The soft brace of claim 1, wherein the one or more tensile elements provides customizable protection to the knee joint by providing customizable resistance against motion of the knee joint; have a length at rest and a length in motion such that the one or more tensile elements provide tension during motion.

3. The soft brace of claim 1, further comprising an adjustment mechanism configured to customize an amount of resistance against motion imposed on the knee joint.

4. The soft brace of claim 3, wherein the adjustment mechanism customizes the amount of resistance manually such that a length of the one or more tensile elements is configured to be adjusted to customize the amount or resistance against motion or automatically using at least one of motors, sensors, and actuators such that the length of the one or more tensile elements is configured to be adjusted to customize the amount or resistance against motion.

5. The soft brace of claim 3, wherein a tension level of the one or more tensile elements is gradually and continuously controlled using a passive mechanical system or in at least one of the one or more tensile elements is adjusted to provide a predefined resistance against a motion of the knee joint.

6. The soft brace of claim 1, further comprising a guiding system configured to route the one or more tensile elements across the brace to maintain an orientation of the one or more tensile elements during a range of motion of the knee joint or configured to route at least one of the one or more tensile elements through the approximate center of rotation of at least one of the knee joint.

7. The soft brace of claim 1, wherein the brace is configured to provide targeted joint protection such that the brace is configured to protect against an excessive range of motion in one or more degrees of freedom.

8. The soft brace of claim 1, wherein at least a portion of the plurality of soft tissue anchors include semi-rigid non-textile components or are in the form of compression mechanisms.

9. The soft brace of claim 1, further comprising one or more sensors to provide feedback on the tension of the one or more tensile elements.

10. The soft brace of claim 1, further comprising dynamic control in the form of one or more sensors configured to measure activity of the knee joint to provide feedback in real time regarding at least one of the load and motions of the knee joint.

11. The soft brace of claim 10, further comprising one or more motors configured to control tension in the one or more tensile elements based on feedback information from the one or more sensors.

12. The soft brace of claim 1, further comprising one or more remote joint anchors positioned remote from the knee joint, the one or more remote joint anchors configured to couple one or more of the one or more tensile elements to a remote joint to provide force distribution relative to the knee joint.

13. The soft brace of claim 1, wherein at least one of the one or more tensile elements is routed through an approximate center of rotation of at least one of the knee joint.

14. The soft brace of claim 1, further comprising one or more flexible hinges that are configured to bend to provide resistance against motion of the knee joint.

15. The soft brace of claim 1, wherein the one or more tensile elements are configured to be slack during normal movement of knee joint.

16. The soft brace of claim 1, wherein the one or more tensile elements are configured to resist knee abduction and internal rotation without affecting knee flexion.

* * * * *